United States Patent
Hood et al.

(10) Patent No.: US 9,783,817 B2
(45) Date of Patent: Oct. 10, 2017

(54) METHODS OF EXPRESSING AND DETECTING ACTIVITY OF EXPANSIN IN PLANT CELLS

(71) Applicant: Arkansas State University, State University, AR (US)

(72) Inventors: Elizabeth E. Hood, Jonesboro, AR (US); Sangwoong Yoon, Gainesville, FL (US)

(73) Assignee: Arkansas State University, State University, AR (US)

(*) Notice: Subject to any disclaimer, the term of this patent is extended or adjusted under 35 U.S.C. 154(b) by 0 days.

(21) Appl. No.: 14/196,412

(22) Filed: Mar. 4, 2014

(65) Prior Publication Data

US 2014/0325698 A1 Oct. 30, 2014

Related U.S. Application Data

(60) Provisional application No. 61/771,965, filed on Mar. 4, 2013.

(51) Int. Cl.
*C12N 15/29* (2006.01)
*C12N 15/82* (2006.01)

(52) U.S. Cl.
CPC ..... *C12N 15/8257* (2013.01); *C12N 15/8242* (2013.01)

(58) Field of Classification Search
None
See application file for complete search history.

(56) References Cited

U.S. PATENT DOCUMENTS

| | | | |
|---|---|---|---|
| 4,683,195 A | 7/1987 | Mullis et al. | 435/6.11 |
| 4,683,202 A | 7/1987 | Mullis | 435/91.2 |
| 4,684,611 A | 8/1987 | Schilperoort et al. | 435/172.3 |
| 4,965,188 A | 10/1990 | Mullis et al. | 435/6.12 |
| 5,015,580 A | 5/1991 | Christou et al. | 435/172.3 |
| 5,268,463 A | 12/1993 | Jefferson | 536/23.7 |
| 5,322,938 A | 6/1994 | McPherson et al. | 536/24.1 |
| 5,352,605 A | 10/1994 | Fraley et al. | 435/418 |
| 5,360,726 A | 11/1994 | Raikhel | 435/172.3 |
| 5,380,831 A | 1/1995 | Adang et al. | 536/23.71 |
| 5,436,391 A | 7/1995 | Fujimoto et al. | 800/205 |
| 5,550,318 A | 8/1996 | Rice et al. | 800/205 |
| 5,584,807 A | 12/1996 | McCabe | 604/71 |
| 5,591,616 A | 1/1997 | Hiei et al. | 435/172.3 |
| 5,599,670 A | 2/1997 | Jefferson | 435/172.3 |
| 5,618,682 A | 4/1997 | Scheirer | 435/8 |
| 5,674,713 A | 10/1997 | McElroy et al. | 435/69.7 |
| 5,717,084 A | 2/1998 | Herrera-Estrella et al. | 536/23.4 |
| 5,728,925 A | 3/1998 | Herrera-Estrella et al. | 800/205 |
| 5,889,174 A | 3/1999 | Warren et al. | 536/23.71 |
| 5,976,796 A | 11/1999 | Szalay et al. | 435/6.11 |
| 6,074,859 A | 6/2000 | Hirokawa et al. | 435/189 |
| 6,255,466 B1* | 7/2001 | Cosgrove et al. | 536/23.1 |
| 6,326,470 B1 | 12/2001 | Cosgrove | 530/370 |
| 6,420,630 B1 | 7/2002 | Wilson et al. | 800/294 |
| 6,919,494 B2 | 7/2005 | Wilson et al. | 800/294 |
| 7,071,384 B2* | 7/2006 | Howard et al. | 800/298 |
| 7,112,723 B2 | 9/2006 | Streatfield et al. | 800/287 |
| 7,169,595 B2* | 1/2007 | Lanahan et al. | 435/196 |
| 7,169,967 B2 | 1/2007 | Streatfield et al. | 800/287 |
| 7,550,579 B2 | 6/2009 | Abbitt et al. | 536/24.1 |

FOREIGN PATENT DOCUMENTS

| | | |
|---|---|---|
| EP | 0342926 A2 | 11/1989 |
| WO | WO/85/01856 | 5/1985 |
| WO | WO/91/19806 | 12/1991 |
| WO | WO/94/17810 | 8/1994 |
| WO | WO/94/23744 | 10/1994 |
| WO | WO/95/14098 | 5/1995 |
| WO | WO/98/39461 | 9/1998 |
| WO | WO/00/12733 | 3/2000 |

OTHER PUBLICATIONS

Kriz (Biochemical Genetics, vol. 27, Nos. 3/4, 1989, p. 239-251).*
Altschul, S. (1993) "A protein alignment scoring system sensitive at all evolutionary distances," *Journal of Molecular Evolution* 36(3), 290-300.
Altschul, S. F. et al. (1990) "Basic local alignment search tool," *Journal of Molecular Biology* 215(3), 403-410.
An, G. et al. (1989) "Functional analysis of the 3' control region of the potato wound-inducible proteinase inhibitor II gene," *Plant Cell* 1(1), 115-122.
Anderson, M. L. M. et al. (1985) "Quantitative Filter Hybridization," in *Nucleic Acid Hybridisation: A Practical Approach* (Hames, B. D., et al., Eds.), pp. 73-111, Oxford University Press, USA.
Anzai, H. et al. (1989) "Transgenic tobacco resistant to a bacterial disease by the detoxification of a pathogenic toxin," *Molecular and General Genetics MGG* 219(3), 492-494.
Armstrong, C. et al. (1991) "Development and availability of germplasm with high type II culture formation response," *Maize Genet Coop Newsletter* 13, 92-93.
Armstrong, C. L. et al. (1985) "Establishment and maintenance of friable, embryogenic maize callus and the involvement of L-proline," *Planta* 164(2), 207-214.
Ballas, N. et al. (1989) "Efficient functioning of plant promoters and poly(A) sites in Xenopus oocytes," *Nucleic Acids Research* 17(19), 7891-7903.

(Continued)

*Primary Examiner* — Anne Kubelik
*Assistant Examiner* — Charles Logsdon
(74) *Attorney, Agent, or Firm* — Medlen & Carroll, LLP

(57) ABSTRACT

A method of expressing heterologous expansin in a plant cell is provided where a nucleic acid molecule encoding expansin is introduced into the plant cell and in an embodiment is operably linked to a promoter preferentially expressing in the seed tissue of the plant, and in another embodiment is linked to a promoter preferentially expressing in the embryo tissue of the seed. An embodiment provides the nucleic acid molecule is operably linked to a second nucleic acid molecule that directs expression to the endoplasmic reticulum, vacuole or cell wall. Plants and plant parts expressing expansin are provided. An assay for detection of expansin activity is also provided.

3 Claims, 17 Drawing Sheets

(56) References Cited

OTHER PUBLICATIONS

Becker, T. W. et al. (1992) "Thecab-m7 gene: a light-inducible, mesophyll-specific gene of maize," *Plant Molecular Biology* 20(1), 49-60.

Belanger, F. C. et al. (1991) "Molecular basis for allelic polymorphism of the maize Globulin-1 gene," *Genetics* 129(3), 863-872.

Bolte, S. et al. (2004) "The N-myristoylated Rab-GTPase m-Rabmc is involved in post-Golgi trafficking events to the lytic vacuole in plant cells," *Journal of Cell Science* 117(6), 943-954.

Broglie, R. et al. (1984) "Light-regulated expression of a pea ribulose-1,5-bisphosphate carboxylase small subunit gene in transformed plant cells," *Science* 224(4651), 838-843.

Bustos, M. M. et al. (1989) "Regulation of beta-glucuronidase expression in transgenic tobacco plants by an A/T-rich, cis-acting sequence found upstream of a French bean beta-phaseolin gene," *Plant Cell and Environment* 1(9), 839-853.

Caddick, M. X. et al. (1998) "An ethanol inducible gene switch for plants used to manipulate carbon metabolism," *Nature Biotechnology* 16(2), 177-180.

Campbell, W. H. et al. (1990) "Codon Usage in Higher Plants, Green Algae, and Cyanobacteria," *Plant Physiology* 92(1), 1-11.

Casas, A. M. et al. (1993) "Transgenic sorghum plants via microprojectile bombardment," *Proceedings of the National Academy of Sciences* 90(23), 11212-11216.

Chamberlin, M. et al. (1970) "New RNA Polymerase from *Escherichia coli* infected with Bacteriophage T7," *Nature* 228(5268), 227-231.

Chandler, V. L. et al. (1989) "Two regulatory genes of the maize anthocyanin pathway are homologous: isolation of B utilizing R genomic sequences," *Plant Cell* 1(12), 1175-1183.

Cho, H.-T. et al. (2002) "Regulation of Root Hair Initiation and Expansin Gene Expression in Arabidopsis," *Plant Cell* 14(12), 3237-3253.

Cho, H. T. et al. (1997) "Expression of expansin genes is correlated with growth in deepwater rice," *Plant Cell* 9(9), 1661-1671.

Chopra, S. et al. (1996) "Alleles of the maize P gene with distinct tissue specificities encode Myb-homologous proteins with C-terminal replacements," *Plant Cell* 8(7), 1149-1158.

Corpet, F. (1988) "Multiple sequence alignment with hierarchical clustering," *Nucleic Acids Research* 16(22), 10881-10890.

Cosgrove, D. (1989) "Characterization of long-term extension of isolated cell walls from growing cucumber hypocotyls," *Planta* 177(1), 121-130.

Cosgrove, D. J. (1999) "Enzymes and Other Agents That Enhance Cell Wall Extensibility," *Annual Review of Plant Physiology and Plant Molecular Biology* 50(1), 391-417.

Cosgrove, D. J. (2000) "Loosening of plant cell walls by expansins," *Nature* 407(6802), 321-326.

Cosgrove, D. J. (2005) "Growth of the plant cell wall," *Nature Reviews Molecular Cell Biology* 6(11), 850-861.

Cosgrove, D. J. et al. (2002) "The Growing World of Expansins," *Plant and Cell Physiology* 43(12), 1436-1444.

Cranage, M. P. et al. (1986) "Identification of the human cytomegalovirus glycoprotein B gene and induction of neutralizing antibodies via its expression in recombinant vaccinia virus," *EMBO Journal* 5(11), 3057-3063.

Creissen, G. et al. (1992) "Molecular characterization of glutathione reductase cDNAs from pea (*Pisum sativum* L.)," *The Plant Journal* 2(1), 129-131.

Crossway, A. et al. (1986) "Integration of foreign DNA following microinjection of tobacco mesophyll protoplasts," *Molecular Genetics and Genomics* 202, 179-185.

De Wet, J. R. et al. (1987) "Firefly luciferase gene: structure and expression in mammalian cells," *Molecular and Cellular Biology* 7(2), 725-737.

Dellaporta. (1988) in *Chromosome Structure and Function* (Appels, et al., Eds.), pp. 263-282, Kluwer Academic Publishers.

Depicker, A. et al. (1982) "Nopaline synthase: transcript mapping and DNA sequence," *Journal of Molecular and Applied Genetics* 1(6), 561-573. (Abstract Only).

Dietrich, C. et al. (2002) "Red fluorescent protein DsRed from *Discosoma* sp. as a reporter protein in higher plants," *BioTechniques* 32(2), 288-290, 292-283. (Abstract Only).

Downes, B. et al. (1998) "Cytokinin regulates the expression of a soybean β-expansin gene by a post-transcriptional mechanism," *Plant Molecular Biology* 37(3), 437-444.

Fobert, P. R. et al. (1994) "T-DNA tagging of a seed coat-specific cryptic promoter in tobacco," *The Plant Journal* 6(4), 567-577.

Fontes, E. B. et al. (1991) "Characterization of an immunoglobulin binding protein homolog in the maize floury-2 endosperm mutant," *Plant Cell and Environment* 3(5), 483-496.

Fraley, R. T. et al. (1983) "Expression of bacterial genes in plant cells," *Proceedings of the National Academy of Sciences* 80(15), 4803-4807.

Fromm, M. et al. (1990) "Inheritance and expression of chimeric genes in the progeny of transgenic maize plants," *Bio/Technology* 8(9), 833-839.

Fromm, M. et al. (1985) "Expression of genes transferred into monocot and dicot plant cells by electroporation," *Proceedings of the National Academy of Sciences* 82(17), 5824-5828.

Garbarino, J. E. et al. (1994) "Isolation of a ubiquitin-ribosomal protein gene (ubi3) from potato and expression of its promoter in transgenic plants," *Plant Molecular Biology* 24(1), 119-127.

Gordon-Kamm, W. et al. (1990) "Transformation of Maize Cells and Regeneration of Fertile Transgenic Plants," *Plant Cell* 2(7), 603-618.

Gould, S. J. et al. (1989) "A conserved tripeptide sorts proteins to peroxisomes," *Journal of Cell Biology* 108(5), 1657-1664.

Graham, F. L. et al. (1973) "A new technique for the assay of infectivity of human adenovirus 5 DNA," *Virology* 52(2), 456-467.

Grdzelishvili, V. Z. et al. (2000) "Mapping of the Tobacco mosaic virus movement protein and coat protein subgenomic RNA promoters in vivo," *Virology* 275(1), 177-192.

Grotewold, E. et al. (1991) "Alternatively spliced products of the maize P gene encode proteins with homology to the DNA-binding domain of myb-like transcription factors," *Proceedings of the National Academy of Sciences* 88(11), 4587-4591.

Grotewold, E. et al. (1994) "The myb-homologous P gene controls phlobaphene pigmentation in maize floral organs by directly activating a flavonoid biosynthetic gene subset," *Cell* 76(3), 543-553.

Guerineau, F. et al. (1991) "Effect of deletions in the cauliflower mosaic virus polyadenylation sequence on the choice of the polyadenylation sites in tobacco protoplasts," *Molecular and General Genetics MGG* 226(1), 141-144.

Guilley, H. et al. (1982) "Transcription of cauliflower mosaic virus DNA: detection of promoter sequences, and characterization of transcripts," *Cell* 30(3), 763-773.

Gurley, W. B. et al. (1986) "Upstream sequences required for efficient expression of a soybean heat shock gene," *Molecular and Cellular Biology* 6(2), 559-565.

Hein, J. (1994) "TreeAlign," in *Computer Analysis of Sequence Data*, pp. 349-364, Springer New York.

Henikoff, S. et al. (1992) "Amino acid substitution matrices from protein blocks," *Proceedings of the National Academy of Sciences* 89(22), 10915-10919.

Henikoff, S. et al. (1993) "Performance evaluation of amino acid substitution matrices," *Proteins* 17(1), 49-61.

Hiei, Y. et al. (1994) "Efficient transformation of rice (*Oryza sativa* L.) mediated by Agrobacterium and sequence analysis of the boundaries of the T-DNA," *The Plant Journal* 6(2), 271-282.

Higgins, D. G. et al. (1988) "CLUSTAL: a package for performing multiple sequence alignment on a microcomputer," *Gene* 73(1), 237-244.

Holwerda, B. C. et al. (1992) "Proaleurain vacuolar targeting is mediated by short contiguous peptide interactions," *Plant Cell* 4(3), 307-318.

Hood, E. E. et al. (2003) "Criteria for high-level expression of a fungal laccase gene in transgenic maize," *Plant Biotechnology Journal* 1(2), 129-140.

(56) References Cited

OTHER PUBLICATIONS

Hood, E. E. et al. (2012) "Manipulating corn germplasm to increase recombinant protein accumulation," *Plant Biotechnology Journal* 10(1), 20-30.
Hood, E. E. et al. (1986) "The hypervirulence of Agrobacterium tumefaciens A281 is encoded in a region of pTiBo542 outside of T-DNA," *Journal of Bacteriology* 168(3), 1291-1301.
Hood, E. E. et al. (2007) "Subcellular targeting is a key condition for high-level accumulation of cellulase protein in transgenic maize seed," *Plant Biotechnology Journal* 5(6), 709-719.
Hood, E. E. et al. (1997) "Commercial production of avidin from transgenic maize: characterization of transformant, production, processing, extraction and purification," *Molecular Breeding* 3, 291-306.
Huang, X. et al. (1992) "Parallelization of a local similarity algorithm," *Computer Applications in the Biosciences* 8(2), 155-165. (Abstract Only).
Ikuta, N. et al. (1990) "The [alpha]-Amylase Gene as a Marker for Gene Cloning: Direct Screening of Recombinant Clones," *Nature Biotechnology* 8(3), 241-242.
Ishida, Y. et al. (1996) "High efficiency transformation of maize (*Zea mays* L.) mediated by Agrobacterium tumefaciens," *Nature Biotechnology* 14(6), 745-750.
Jefferson, R. A. et al. (1987) "Gus fusions: beta-glucuronidase as a sensitive and versatile gene fusion marker in higher plants," *EMBO Journal* 6(13), 3901-3907.
Joshi, C. P. (1987) "Putative polyadenylation signals in nuclear genes of higher plants: a compilation and analysis," *Nucleic Acids Research* 15(23), 9627-9640.
Kacian, D. L. et al. (1972) "A Replicating RNA Molecule Suitable for a Detailed Analysis of Extracellular Evolution and Replication," *Proceedings of the National Academy of Sciences of the United States of America* 69(10), 3038-3042.
Kalderon, D. et al. (1984) "A short amino acid sequence able to specify nuclear location," *Cell* 39(3), 499-509.
Kao, C. Y. et al. (1996) "Localization and interaction of the cis-acting elements for abscisic acid, VIVIPAROUS1, and light activation of the C1 gene of maize," *Plant Cell* 8(7), 1171-1179.
Karlin, S. et al. (1993) "Applications and statistics for multiple high-scoring segments in molecular sequences," *Proceedings of the National Academy of Sciences* 90(12), 5873-5877.
Kato, N. et al. (2002) "Spectral Profiling for the Simultaneous Observation of Four Distinct Fluorescent Proteins and Detection of Protein-Protein Interaction via Fluorescence Resonance Energy Transfer in Tobacco Leaf Nuclei," *Plant Physiology* 129(3), 931-942.
Katz, E. et al. (1983) "Cloning and Expression of the Tyrosinase Gene from Streptomyces antibioticus in Streptomyces . lividans," *Journal of General Microbiology* 129(9), 2703-2714.
Kay, M. A. et al. (1997) "Gene therapy," *Proceedings of the National Academy of Sciences* 94(24), 12744-12746.
Kende, H. et al. (2004) "Nomenclature for members of the expansin superfamily of genes and proteins," *Plant Molecular Biology* 55(3), 311-314.
Klein, T. M. et al. (1992) "Transformation of microbes, plants and animals by particle bombardment," *Nature Biotechnology* 10(3), 286-291.
Knox, C. P. et al. (1987) "Structure and organization of two divergent α-amylase genes from barley," *Plant Molecular Biology* 9(1), 3-17.
Kozak, M. (1986) "Point mutations define a sequence flanking the AUG initiator codon that modulates translation by eukaryotic ribosomes," *Cell* 44(2), 283-292.
Kozak, M. (1987) "An analysis of 5'-noncoding sequences from 699 vertebrate messenger RNAs," *Nucleic Acids Research* 15(20), 8125-8148.
Kusnadi, A. R. et al. (1997) "Production of recombinant proteins in transgenic plants: Practical considerations," *Biotechnology and Bioengineering* 56(5), 473-484.

Lerner, D. R. et al. (1989) "Cloning and Characterization of Root-Specific Barley Lectin," *Plant Physiology* 91(1), 124-129.
Li, H. M. et al. (1992) "Information for targeting to the chloroplastic inner envelope membrane is contained in the mature region of the maize Bt1-encoded protein," *Journal of Biological Chemistry* 267(26), 18999-19004.
MacDonald, M. H. et al. (1991) "Characterization of the polyadenylation signal from the T-DNA-encoded octopine synthase gene," *Nucleic Acids Research* 19(20), 5575-5581.
Maiti, I. B. et al. (1997) "Promoter/leader deletion analysis and plant expression vectors with the figwort mosaic virus (FMV) full length transcript (FLt) promoter containing single or double enhancer domains," *Transgenic Research* 6(2), 143-156.
Maniatis, T. et al. (1987) "Regulation of inducible and tissue-specific gene expression," *Science* 236(4806), 1237-1245.
Mathur, J. et al. (1998) "PEG-Mediated Protoplast Transformation with Naked DNA," in *Arabidopsis Protocols* (Martinez-Zapater, J., et al., Eds.), pp. 267-276, Humana Press.
Matsuoka, K. et al. (1991) "Propeptide of a precursor to a plant vacuolar protein required for vacuolar targeting," *Proceedings of the National Academy of Sciences* 88(3), 834-838.
McQueen-Mason, S. et al. (1992) "Two endogenous proteins that induce cell wall extension in plants," *Plant Cell* 4(11), 1425-1433.
McQueen-Mason, S. J. et al. (1995) "Expansin mode of action on cell walls. Analysis of wall hydrolysis, stress relaxation, and binding," *Plant Physiology* 107(1), 87-100.
Medrano, G. et al. (2009) "Rapid system for evaluating bioproduction capacity of complex pharmaceutical proteins in plants," in *Recombinant Proteins From Plants. Recombinant Proteins From Plants: Methods and Protocols*, pp. 51-67, Humana Press, Totowa, NJ. (Abstract Only).
Meinkoth, J. et al. (1984) "Hybridization of nucleic acids immobilized on solid supports," *Analytical Biochemistry* 138(2), 267-284.
Miki, B. et al. (2004) "Selectable marker genes in transgenic plants: applications, alternatives and biosafety," *Journal of Biotechnology* 107(3), 193-232.
Mogen, B. et al. (1990) "Upstream sequences other than AAUAAA are required for efficient messenger RNA 3'-end formation in plants," *Plant Cell* 2(12), 1261-1272.
Moloney, M. M. et al. (1989) "High efficiency transformation of Brassica napus using Agrobacterium vectors," *Plant Cell Reports* 8(4), 238-242.
Morrison, D. A. et al. (1997) "Effects of nucleotide sequence alignment on phylogeny estimation: a case study of 18S rDNAs of apicomplexa," *Molecular Biology and Evolution* 14(4), 428-441.
Muhitch, M. J. et al. (2002) "Isolation of a Promoter Sequence From the Glutamine Synthetase$_{1-2}$ Gene Capable of Conferring Tissue-Specific Gene Expression in Transgenic Maize," *Plant Science* 163(4), 865-872.
Mullis, K. B. et al. (1987) "[21] Specific synthesis of DNA in vitro via a polymerase-catalyzed chain reaction," in *Methods in Enzymology* (Ray, W., Ed.), pp. 335-350, Academic Press. (Abstract Only).
Munro, S. et al. (1987) "A C-terminal signal prevents secretion of luminal ER proteins," *Cell* 48(5), 899-907.
Munroe, D. et al. (1990) "Tales of poly(A): a review," *Gene* 91(2), 151-158.
Murray, E. E. et al. (1989) "Codon usage in plant genes," *Nucleic Acids Research* 17(2), 477-498.
Nakamura, K. et al. (1993) "Protein targeting to the vacuole in plant cells," *Plant Physiology* 101(1), 1-5.
Nash, J. et al. (1990) "Bronze-2 gene of maize: reconstruction of a wild-type allele and analysis of transcription and splicing," *Plant Cell* 2(11), 1039-1049.
Needleman, S. B. et al. (1970) "A general method applicable to the search for similarities in the amino acid sequence of two proteins," *Journal of Molecular Biology* 48(3), 443-453.
Odell, J. T. et al. (1985) "Identification of DNA sequences required for activity of the cauliflower mosaic virus 35S promoter," *Nature* 313(6005), 810-812.
Opsahl-Sorteberg, H.-G. et al. (2004) "Identification of a 49-bp fragment of the HvLTP2 promoter directing aleurone cell specific expression," *Gene* 341(0), 49-58.

(56) References Cited

OTHER PUBLICATIONS

Pearson, W. R. (1994) "Using the FASTA Program to Search Protein and DNA Sequence Databases," in *Computer Analysis of Sequence Data* (Griffin, A. M., et al., Eds.), pp. 307-331, Humana Press.
Pearson, W. R. et al. (1988) "Improved tools for biological sequence comparison," *Proceedings of the National Academy of Sciences* 85(8), 2444-2448.
Proudfoot, N. (1991) "Poly(A) signals," *Cell* 64(4), 671-674.
Ralston, E. J. et al. (1988) "Sequence of three bronze alleles of maize and correlation with the genetic fine structure," *Genetics* 119(1), 185-197.
Rochange, S. F. et al. (2001) "Impaired growth in transgenic plants over-expressing an expansin isoform," *Plant Molecular Biology* 46(5), 581-589.
Rogers, J. C. (1985) "Two barley alpha-amylase gene families are regulated differently in aleurone cells," *Journal of Biological Chemistry* 260(6), 3731-3738.
Saalbach, G. et al. (1991) "Different legumin protein domains act as vacuolar targeting signals," *Plant Cell* 3(7), 695-708.
Sambrook, J. et al. (1989) in *Molecular Cloning: A Laboratory Manual* (Sambrook, J., et al., Eds.) 2nd ed., pp. 16.07-16.08, Cold Spring Harbor Laboratory Press, New York.
Sambrook, J. et al. (1989) "Transfer and Fixation of Denatured RNA to Membranes," in *Molecular Cloning: A Laboratory Manual* (Sambrook, J., et al., Eds.) 2nd ed., pp. 7.39-7.52, Cold Spring Harbor Laboratory Press, New York.
Sambrook, J. et al. (1989) "Synthesis of Single-stranded RNA Proves by In Vitro Transcription," in *Molecular Cloning: A Laboratory Manual* (Sambrook, J., et al., Eds.) 2nd ed., pp. 9.31-9.58, Cold Spring Harbor Laboratory Press, New York.
Sanfaçon, H. et al. (1991) "A dissection of the cauliflower mosaic virus polyadenylation signal," *Genes & Development* 5(1), 141-149.
Sathitsuksanoh, N. et al. (2009) "Saccharification of a Potential Bioenergy Crop, *Phragmites australis* (Common Reed), by Lignocellulose Fractionation Followed by Enzymatic Hydrolysis at Decreased Cellulase Loadings," *Industrial & Engineering Chemistry Research* 48, 6441-6447.
Scheffler, B. et al. (1994) "Molecular analysis of C1 alleles in *Zea mays* defines regions involved in the expression of this regulatory gene," *Molecular and General Genetics MGG* 242(1), 40-48.
Shannon, J. C. et al. (1998) "Brittle-1, an Adenylate Translocator, Facilitates Transfer of Extraplastidial Synthesized ADP-Glucose into Amyloplasts of Maize Endosperms," *Plant Physiology* 117(4), 1235-1252.
Shaw, C. H. et al. (1984) "A functional map of the nopaline synthase promoter," *Nucleic Acids Research* 12(20), 7831-7846.
Shcherban, T. Y. et al. (1995) "Molecular cloning and sequence analysis of expansins—a highly conserved, multigene family of proteins that mediate cell wall extension in plants," *Proceedings of the National Academy of Sciences* 92(20), 9245-9249.
Sheen, J. et al. (1995) "Green-fluorescent protein as a new vital marker in plant cells," *The Plant Journal* 8(5), 777-784.
Shinshi, H. et al. (1990) "Structure of a tobacco endochitinase gene: evidence that different chitinase genes can arise by transposition of sequences encoding a cysteine-rich domain," *Plant Molecular Biology* 14(3), 357-368.
Sidorenko, L. et al. (1999) "Characterization of the regulatory elements of the maize P-rr gene by transient expression assays," *Plant Molecular Biology* 39(1), 11-19.
Smith, T. F. et al. (1981) "Comparison of biosequences," *Advances in Applied Mathematics* 2(4), 482-489.
Sonnhammer, E. L. L. et al. (1998) "Pfam: Multiple sequence alignments and HMM-profiles of protein domains," *Nucleic Acids Research* 26(1), 320-322.

Stiefel, V. et al. (1990) "Expression of a maize cell wall hydroxyproline-rich glycoprotein gene in early leaf and root vascular differentiation," *Plant Cell* 2(8), 785-793.
Streatfield, S. J. (2002) "Development of an Edible Subunit Vaccine in Corn against Enterotoxigenic Strains of *Escherichia coli*," *In Vitro Cellular and Development Biology—Plant* 38, 11-17.
Streatfield, S. J. (2007) "Approaches to achieve high-level heterologous protein production in plants," *Plant Biotechnology Journal* 5(1), 2-15.
Streatfield, S. J. et al. (2001) "Plant-based vaccines: unique advantages," *Vaccine* 19(17-19), 2742-2748.
Sullivan, T. et al. (1995) "The maize brittle1 gene encodes amyloplast membrane polypeptides," *Planta* 196(3), 477-484.
Sullivan, T. D. et al. (1991) "Analysis of maize brittle-1 alleles and a defective Suppressor-mutator-induced mutable allele," *Plant Cell* 3(12), 1337-1348.
Sun, Y. et al. (2005) "Brassinosteroid Regulates Fiber Development on Cultured Cotton Ovules," *Plant and Cell Physiology* 46(8), 1384-1391.
Sutcliffe, J. G. (1978) "Nucleotide sequence of the ampicillin resistance gene of *Escherichia coli* plasmid pBR322," *Proceedings of the National Academy of Sciences of the United States of America* 75(8), 3737-3741.
Taylor, L. P. et al. (1990) "Genetic regulation and photocontrol of anthocyanin accumulation in maize seedlings," *Plant Cell* 2(2), 115-127.
Teeri, T. H. et al. (1989) "Gene fusions to lacZ reveal new expression patterns of chimeric genes in transgenic plants," *EMBO Journal* 8(2), 343-350.
Uchimiya, H. (1993) "Bialaphos Treatment of Transgenic Rice Plants Expressing a bar Gene Prevents Infection by the Sheath Blight Pathogen (Rhizoctonia solani)," *Bio/Technology* 11(7), 835-836.
Velten, J. et al. (1985) "Selection-expression plasmid vectors for use in genetic transformation of higher plants," *Nucleic Acids Research* 13(19), 6981-6998.
Voss, S. D. et al. (1986) "The role of enhancers in the regulation of cell-type-specific transcriptional control," *Trends in Biochemical Sciences* 11(7), 287-289.
Wan, Y. et al. (1994) "Generation of Large Numbers of Independently Transformed Fertile Barley Plants," *Plant Physiology* 104(1), 37-48.
Weising, K. et al. (1988) "Foreign genes in plants: transfer, structure, expression, and applications," *Annual Review of Genetics* 22(1), 421-477.
White, J. et al. (1990) "A cassette containing the bar gene of Streptomyces hygroscopicus: a selectable marker for plant transformation," *Nucleic Acids Research* 18(4), 1062.
Wienand, U. et al. (1986) "Molecular cloning of the c2 locus of *Zea mays*, the gene coding for chalcone synthase," *Molecular and General Genetics MGG* 203(2), 202-207.
Woodard, S. L. et al. (2003) "Maize (*Zea mays*)-derived bovine trypsin: characterization of the first large-scale, commercial protein product from transgenic plants," *Biotechnology and Applied Biochemistry* 38(Pt 2), 123-130.
Wu, D. Y. et al. (1989) "The ligation amplification reaction (LAR)—Amplification of specific DNA sequences using sequential rounds of template-dependent ligation," *Genomics* 4(4), 560-569.
Zhang, J. et al. (1997) "PowerBLAST: A New Network BLAST Application for Interactive or Automated Sequence Analysis and Annotation," *Genome Research* 7(6), 649-656.
Zukowski, M. M. et al. (1983) "Chromogenic identification of genetic regulatory signals in Bacillus subtilis based on expression of a cloned Pseudomonas gene," *Proceedings of the National Academy of Sciences* 80(4), 1101-1105.

\* cited by examiner (A)

(B)

(C)

A

B

| No. | Sample description |
|---|---|
| 1. | Crude extract – Homogenation buffer |
| 2. | Crude extract – Extraction buffer |
| 3. | Supernatant after 60% ammonium sulfate precipitation |
| 4. | Re-suspended 60% ammonium sulfate pellet |
| 5. | Native corn extract |

| Protein concentration (ug) | Activity |
|---|---|
| 20 (Denatured) | 0 |
| 5 | 5.09 |
| 10 | 7.88 |
| 20 | 9.84 |
| 40 | 11.87 |

FIGURE 15

- Bamboo Expansin cDNA (SEQ ID NO: 1) with 3' Histidine tag shown in bold (SEQ ID NO: 2) (without signal sequence). Note the last 9 nucleotides are not a part of the his tag but represent the stop codon (TAA) plus a Sac I restriction endonuclease cloning site.

TCTAGAGCGCCGCGAGCCCTCGGGCAGTGGCAGTCCGGGCACGCCACGTTCTACGGCGGTGGCGACGCCTCCGGCAC
AATGGGAGGCGCGTGCGGTTACGGGAACCTGTACAGCCAGGGGTACGGCACGAGCACGGCGGCGCTGAGCACGGCGC
TGTTCAACAACGGGCTGAGCTGCGGGTCGTGCTACGAGCTGCGGTGCTCGGGCGACCCCAAGTGGTGCCTCCCCGGC
GCCATCACGGTGACGGCCACCAACTTCTGCCCGCCCAACTACGCGCTCCCCAACAACGACGGCGGCTGGTGCAACCC
CCCGCTCCAGCACTTCGACCTCGCCGAGCCCGCCTTCCTCCACATCGCTCAGTACCGCGCCGGCATCGTCCCCGTCT
CCTTCCGCAGGGTGGCGTGCGTGAAGAAGGGCGGGGTCCGGTTCACGGTGAACGGGCACTCGTACTTCAACCTGGTG
CTGGTGACCAACGTGGGCGGGGCGGGGGACGTGCACGCGGTGGCGATCAAGGGGTCGCGCACGGGGTGGCAGCCCAT
GGCGCGCAACTGGGGCCAGAACTGGCAGAGCAACGCCTACCTCAACGGCCAGGCGCTGTCCTTCCGCGTCACCGCCA
GCGACGGCCGCGCGCTCACCTCCGCCAACGTCGCGCCCGTGGGGTGGCAGTTCGGCCAGACCTTCGAGGGCGCCCAG
TTCCACCATCACCATCACCAT TAAGAGCTC

FIGURE 16

- Bamboo Expansin genomic DNA (without signal sequence) (SEQ ID NO: 3)

atggcgtcctcctcttcctccatcctcctgttcctcgcttctcttctcctcgccGCGCCGCGAGCCCTCGGGCAGTGG
CAGTCCGGGCACGCCACGTTCTACGGCGGCGGCGACGCCTCCGGCACAATGGGTACGTGCACAGAACATCAATTTTCA
TTCCGTTCTTGAAACTTCAAGTCACTAGTATACCTTGATGGATTAATTCGAGCGTGCACGCGCGGCGTTTGTGTGTGC
GTACGTGCAGGAGGCGCGTGCGGGTACGGGAACCTGTACAGCCAGGGGTACGGCCCGAGCACGGCGGCGCTGAGCACG
GCGCTGTTCAACAACGGGCTGAGCTGCGGGTCGTGCTACGAGCTGCGGTGCTCGGGCGACCCCAAGTGGTGCTTCCCC
GGCGCCATCACGGTGACGGCCACCAACTTCTGCCCGCCCAACTACGCGCTCCCCAACAACGACGGCGGCTGGTGCAAC
CCCCGCTCCAGCACTTCGACCTCGCCGAGCCCGCCTTCCTGCACATCGCCCAGTACCGCGCCGGCATCGTCCCCGTC
TCGTTCCGCAGGCACGTCCCCTCATTCGGTTTCTTTTCTTTACTCCAACCGTATGTAACTCGTTGTTACCACTGTGTC
ACTGTAGCGAAGGCGACAGTATACTACTAGTAACTACTCGTAGACAGTAACGTCACATATAGCTACAATTTCTTCAAA
TGCTGCGTGTTGCTCGAATGCAGGGTGGCGTGCGTGAAGAAGGGCGGGATCCGGTTCACGGTGAACGGGCACTCGTAC
TTCAACCTGGTGCTGGTGACCAACGTGGGCGGCGCCGGGGACGTGCACGCGGTGGCGATCAGGGGGTCGCGCACGGGG
TGGCAGCCCATGTCGCGCAACTGGGGCCAGAACTGGCAGAGCAACGCCTACCTCAACGGCCAGGCGCTCTCCTTCCGC
GTCACCGCCAGCGACGGCCGCGCCCTCACCTGCGCCAACGTCGCGCCCGCGGGTGGCAGTTCGGCCAGACCTTCGAG
GGCGCCCAGTTCTAA

FIGURE 17

Cucumber expansin gene (SEQ ID NO: 4)

```
  1 GAATAATTAA CAAACATTGC CACTAATTAA TCTCATTTAT TAAACACATT TCTTTTTCGC
 61 TAATCTCCCC TTTCTTCCCC CTCTTCTCTT CTAAACCCAC AAAACAAACC CCACTTTTCT
121 TCACAAACTA TTTTCAAATA TAAACCCATT CTTATGGCTT TTTCTTACTC ACCCTTCTCC
181 TCTCTCTTTC TTCTTCCTTT CTTCTTTGTC TTCACCTTCG CTGACTACGG TGGCTGGCAG
241 AGCGGCCACG CCACCTTTTA TGGTGGTGGT GACGCATCTG GCACCATGGG TGGAGCTTGT
301 GGGTATGGGA ATTTATACAG CCAAGGGTAT GGCACGAACA CGGTGGCGCT GAGCACTGCG
361 CTATTTAACA ATGGATTAAG TTGTGGTGCT TGCTTCGAAA TGACTTGTAC AAACGACCCT
421 AAATGGTGCC TTCCGGGAAC TATTAGGGTC ACTGCCACCA ACTTTTGCCC TCCTAACTTT
481 GCTCTCCCTA ACAACAATGG TGGATGGTGC AACCCTCCTC TCCAACACTT CGACATGGCT
541 GAGCCTGCCT TCCTTCAAAT CGCTCAATAC CGAGCTGGTA TCGTCCCCGT CTCCTTTCGT
601 AGGGTACCAT GTATGAAGAA AGGTGGAGTG AGGTTTACAA TCAATGGCCA CTCATACTTC
661 AACCTCGTTT TGATCACAAA CGTCGGTGGC GCAGGCGACG TCCACTCTGT GTCGATAAAG
721 GGGTCTCGAA CTGGATGGCA ATCCATGTCT AGAAATTGGG GCCAAAACTG GCAAAGCAAC
781 AACTATCTCA ATGGCCAAGG CCTTTCCTTT CAAGTCACTC TTAGTGATGG TCGCACTCTC
841 ACTGCCTATA ATCTCGTTCC TTCCAATTGG CAATTTGGCC AAACCTATGA AGGCCCTCAA
901 TTCTAAACCA TATCAGCCAC ACTGCTATGA CTACTACTAC TTCACAAAAC AAAACACACA
961 AAACAAACAA ACAACAACAA AACGCGAACG AC
```

FIGURE 18

Phyllostachys edulis cDNA clone: bphyem105j06, full insert sequence
GenBank: FP094161.1 [SEQ ID NO: 9]

```
   1 acattcgcgc ttctgtcaag taaaccgcct cagcacagag ctccaatggc gtcctcctct
  61 tcctccatcc tcctgttcct cgcttctctt ctcctcgccg cgccgcgagc cctcgggcag
 121 tggcagtccg ggcacgccac gttctacggc ggcggcgacg cctccggcac aatgggaggc
 181 gcgtgcgggt acgggaacct gtacagccag gggtacggcc cgagcacggc ggcgctgagc
 241 acggcgctgt caacaacgg gctgagctgc gggtcgtgct acgagctgcg gtgctcgggc
 301 gaccccaagt ggtgcttccc cggcgccatc acggtgacgg ccaccaactt ctgccgccc
 361 aactacgcgc tccccaacaa cgacggcggc tggtgcaacc cccgctcca gcacttcgac
 421 ctcgccgagc ccgccttcct gcacatcgcc cagtaccgcg ccggcatcgt cccgtctcg
 481 ttccgcaggg tggcgtgcgt gaagaagggc gggatccggt tcacggtgaa cgggcactcg
 541 tacttcaacc tggtgctggt gaccaacgtg ggcggcgccg gggacgtgca cgcggtggcg
 601 atcagggggt cgcgcacggg gtggcagccc atgtcgcgca actgggcca gaactggcag
 661 agcaacgcct acctcaacgg ccaggcgctc tccttccgcg tcaccgccag cgacggccgc
 721 gccctcacct gcgccaacgt cgcgccccgcg gggtggcagt tcggccagac cttcgagggc
 781 gcccagttct gatcacgacc cgaccgccag gattgacccg tccagctcct ttgattaatt
 841 tagagcttta tgtttagcca agatgagatt cccttttta atctcgagtt tcatcggtgt
 901 tgatttattc atctggtcca gccctgatgc tgaggttgct cctggaagaa aacaaggatg
 961 ggcacccgcg tgtcggaggc tgggacgtat ctgaatgttt gctgctcagt tctgttacct
1021 gagatttgta taggatatat aatactagta ctagagaagt gcggtagtgg tagagagtct
1081 cttgagagag aggcaaagag acttgtatgt atgaatgaaa ttgttcgttt gctttgtc
```

METHODS OF EXPRESSING AND DETECTING ACTIVITY OF EXPANSIN IN PLANT CELLS

CROSS-REFERENCE TO RELATED APPLICATIONS

The present application claims the benefit of U.S. Provisional Patent Application No. 61/771,965, filed on. Mar. 4, 2013, which is incorporated herein by reference.

STATEMENT OF GOVERNMENTAL SUPPORT

This invention was made with Government support under contract (DE FG36 GO88025) awarded by The US Department of Energy. The government has certain rights in the invention.

A Sequence Listing has been submitted in an ASCII text file 17753NEWprj_ST25.txt, created on Jul. 2, 2014, consisting of 18 KB, the entire content of which is herein incorporated by reference.

FIELD OF THE INVENTION

This invention is in the field of plant biology and agriculture and relates to novel production of the plant protein expansin. The present invention further provides methods of producing transgenic plants which produce the expansin protein or related proteins in various stages of transgenic plant development.

BACKGROUND OF THE INVENTION

Expansin refers to a family of closely related nonenzymatic proteins found in the plant cell wall, with important roles in plant cell growth, fruit softening, abscission, emergence of root hairs, pollen tube invasion of the stigma and style, meristem function, and other developmental processes where cell wall loosening occurs [1]. Expansins were originally discovered as mediators of acid growth, which refers to the widespread characteristic of growing plant cell walls to expand faster at low (acidic) pH than at neutral pH [2]. Expansins are thus linked to auxin action. They are also linked to cell enlargement and cell wall changes induced by other plant hormones such as gibberellins [3], cytokinin [4], ethylene[5], and brassinosteroids [6].

SUMMARY OF THE INVENTION

This invention is described in preferred embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the following description, numerous specific details are recited to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

In one embodiment, the invention relates to a method of producing expansin as set forth herein. In one embodiment, the invention relates to a method of producing expansin comprising introducing into a plant cell a vector comprising a nucleic acid molecule encoding expansin operably linked to a regulatory region preferentially expressing said expansin in plant seed cells. In one embodiment, said regulatory region preferentially expresses said expansin in plant embryo cells. In one embodiment, the method further comprises a second nucleic acid molecule that targets expression of said expansin to a plant cell part selected from endoplamic reticulum, vacuole and cell wall of said cell. In one embodiment, said second nucleic acid molecule targets expression of said expansin to endoplasmic reticulum. In one embodiment, said plant cell is a maize plant cell. In one embodiment, said expansin produced comprises at least 0.015% of dry weight of seed. In one embodiment, said expansin produced comprises at least 0.5% total soluble protein In one embodiment, the method further comprises producing a plant from said plant cell wherein said plant growth is not inhibited compared to a plant not expressing said expansin and wherein said plant produces seed comprising said expansin. In one embodiment, said expansin is expressed in said plant seed at a level of at least two times higher than a plant not comprising said nucleic acid molecule encoding expansin. In one embodiment, said expansin is expressed in said plant seed at a level of up to at least ten times higher than a plant not comprising said nucleic acid molecule encoding expansin.

In one embodiment, the invention relates to a method of producing expansin in a plant comprising introducing into a plant cell a vector comprising a nucleic acid molecule encoding expansin operably linked to a regulatory region preferentially expressing said expansin in plant seed cells and a second nucleic acid molecule targeting expression of said expansin to endoplasmic reticulum.

In one embodiment, the invention relates to a plant comprising a vector comprising a nucleic acid molecule encoding expansin operably linked to a regulatory region preferentially expressing said expansin in seed of said plant. In one embodiment, said regulatory region preferentially expresses said expansin in plant embryo cells. In one embodiment, said plant further comprises a second nucleic acid molecule that targets expression of said expansin to a plant cell part selected from endoplamic reticulum, vacuole and cell wall of said cell. In one embodiment, said second nucleic acid molecule targets expression of said expansin to endoplasmic reticulum. In one embodiment, said plant cell is a maize plant cell. In one embodiment, the plant further comprises producing a plant from said plant cell wherein said plant growth is not inhibited compared to a plant not expressing said expansin and wherein said plant produces seed comprising said expansin. In one embodiment, said expansin is expressed in said plant seed at a level of at least two times higher than a plant not comprising said nucleic acid molecule encoding expansin. In one embodiment, said expansin is expressed in said plant seed at a level of at least ten times higher than a plant not comprising said nucleic acid molecule encoding expansin. In one embodiment, the invention comprises the seed of the plant hereto described. In one embodiment, the invention comprises the embryo of said seed.

In one embodiment, the invention relates to a method of determining the expansin activity of a composition, said method comprising (i) contacting a first composition comprising expansin produced from plant tissue comprising heterologous expansin with at least one cellulase and cellulose, (ii) measuring the amount of glucose produced by said first composition, (iii) contacting a second composition comprising expansin produced from plant tissue which does not comprise heterologous expansin with at least one cellulase and cellulose, (iv) measuring the amount of glucose produced by the second composition, (v) comparing the glucose produced by the first composition with the glucose produced by the second composition, and (vi) determining if the glucose produced by the first composition is increased compared to the second composition. In one embodiment, said glucose is measured by a glucose oxidase assay In one embodiment, the method further comprises extracting any of said expansin in plant tissue in a buffer comprising a NaCl concentration from 0 to no more than 300 mM.

Other objects, advantages, and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

DEFINITIONS

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The term "plant" is used in it broadest sense. It includes, but is not limited to, any species of woody, ornamental or decorative, crop or cereal, fruit or vegetable plant, and photosynthetic green algae (for example, *Chlamydomonas reinhardtii*). It also refers to a plurality of plant cells which are largely differentiated into a structure that is present at any stage of a plant's development. Such structures include, but are not limited to, a fruit, shoot, stem, leaf, flower petal, etc. The term "plant tissue" includes differentiated and undifferentiated tissues of plants including those present in roots, shoots, leaves, pollen, seeds and tumors, as well as cells in culture (for example, single cells, protoplasts, embryos, callus, etc.). Plant tissue may be in planta, in organ culture, tissue culture, or cell culture. The term "plant part" as used herein refers to a plant structure or a plant tissue. The term "seed" as used herein includes all tissues which result from the development of a fertilized plant egg; thus, it includes a matured ovule containing an embryo and stored nutrients, as well as the integument or integuments differentiated as the protective seed coat, or testa. The nutrients in seed tissues may be stored in the endosperm or in the body of the embryo, notably in the cotyledons, or both.

The term "crop" or "crop plant" is used in its broadest sense. The term includes, but is not limited to, any species of plant or algae edible by humans or used as a feed for animals or used, or consumed by humans, or any plant or algae used in industry or commerce. By a "crop plant" is intended any plant that is cultivated for the purpose of producing plant material that is sought after by man for either oral consumption, or for utilization in an industrial, pharmaceutical, or commercial process. The invention may be applied to any of a variety of plants, including, but not limited to maize, wheat, rice, barley, soybean, cotton, sorghum, beans in general, rape/canola, alfalfa, flax, sunflower, safflower, millet, rye, sugarcane, sugar beet, cocoa, tea, *Brassica*, cotton, coffee, sweet potato, flax, peanut, clover; vegetables such as lettuce, tomato, cucurbits, cassava, potato, carrot, radish, pea, lentils, cabbage, cauliflower, broccoli, Brussels sprouts, peppers, and pineapple, conifers and other trees, tree fruits such as citrus, apples, pears, peaches, apricots, walnuts, avocado, banana, and coconut; and flowers such as orchids, carnations and roses.

The term plant cell "compartments or organelles" is used in its broadest sense. The term includes but is not limited to, the endoplasmic reticulum, Golgi apparatus, trans Golgi network, plastids, sarcoplasmic reticulum, glyoxysomes, mitochondrial, chloroplast, and nuclear membranes, and the like.

The terms "protein" and "polypeptide" refer to compounds comprising amino acids joined via peptide bonds and are used interchangeably. A "protein" or "polypeptide" encoded by a gene is not limited to the amino acid sequence encoded by the gene, but includes post-translational modifications of the protein.

Where the term "amino acid sequence" is recited herein to refer to an amino acid sequence of a protein molecule, "amino acid sequence" and like terms, such as "polypeptide" or "protein" are not meant to limit the amino acid sequence to the complete, native amino acid sequence associated with the recited protein molecule. Furthermore, an "amino acid sequence" can be deduced from the nucleic acid sequence encoding the protein.

The term "portion" or "fragment" when used in reference to a protein (as in "a portion of a given protein") refers to fragments of that protein. The fragments may range in size from four amino acid residues to the entire amino acid sequence minus one amino acid.

The term "chimera" when used in reference to a polypeptide refers to the expression product of two or more coding sequences obtained from different genes, that have been cloned together and that, after translation, act as a single polypeptide sequence. Chimeric polypeptides are also referred to as "hybrid" polypeptides. The coding sequences include those obtained from the same or from different species of organisms.

The term "fusion" when used in reference to a polypeptide refers to a chimeric protein containing a protein of interest joined to an exogenous protein fragment (the fusion partner). The fusion partner may serve various functions, including enhancement of solubility of the polypeptide of interest, as well as providing an "affinity tag" to allow purification of the recombinant fusion polypeptide from a host cell or from a supernatant or from both. If desired, the fusion partner may be removed from the protein of interest after or during purification.

The term "homolog" or "homologous" when used in reference to a polypeptide refers to a high degree of sequence identity between two polypeptides, or to a high degree of similarity between the three-dimensional structure or to a high degree of similarity between the active site and the mechanism of action. In a preferred embodiment, a homolog has a greater than 60% sequence identity, and more preferably greater than 75% sequence identity, and still more preferably greater than 90% sequence identity, with a reference sequence.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (for example, 99 percent sequence identity). Preferably, residue positions which are not identical differ by conservative amino acid substitutions.

The terms "variant" and "mutant" when used in reference to a nucleic acid sequence means sequences that are at least 90% identical. Preferred variants have less than 10%, and preferably less than 5%, and still more preferably less than 2% changes (whether substitutions, deletions, and so on).

The nucleic acid molecules of this invention are typically DNA molecules, and include cDNA, genomic DNA, synthetic forms, and mixed polymers, both sense and antisense strands, and may be chemically or biochemically modified, or may contain non-natural or derivatised nucleotide bases as will be appreciated by those skilled in the art. Such modifications include labels, methylation, intercalators, alkylators and modified linkages.

The term "gene" refers to a nucleic acid (for example, DNA or RNA) sequence that comprises coding sequences necessary for the production of an RNA, or a polypeptide or its precursor. A functional polypeptide can be encoded by a full length coding sequence or by any portion of the coding sequence as long as the desired activity or functional properties (for example, enzymatic activity, ligand binding, signal transduction, etc.) of the polypeptide are retained. The term "portion" when used in reference to a gene refers to fragments of that gene. The fragments may range in size from a few nucleotides to the entire gene sequence minus one nucleotide. Thus, "a nucleotide comprising at least a portion of a gene" may comprise fragments of the gene or the entire gene.

The term "gene" also encompasses the coding regions of a structural gene and includes sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences which are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers which control or influence the transcription of the gene. The 3' flanking region may contain sequences which direct the termination of transcription, posttranscriptional cleavage and polyadenylation.

The term "expression cassette" means a part of a vector DNA used for cloning and transformation. In each successful transformation, the expression cassette directs the cell's machinery to make RNA and protein. Some expression cassettes are designed for modular cloning of protein-encoding sequences so that the same cassette can easily be altered to make different proteins. An expression cassette is composed of one or more genes and the sequences controlling their expression. Three components comprise an expression cassette: a promoter sequence, an open reading frame, and a 3' untranslated region that, in eukaryotes, usually contains a polyadenylation site. Different expression cassettes can be transformed into different organisms including bacteria, yeast, plants, and mammalian cells as long as the correct regulatory sequences are used.

The phrase "expression corresponds with the embryonic stage of plant development" means that the production of RNA transcripts and/or subsequently related proteins under control of the preceeding promoter is significantly produced during the embryonic stage of plant development.

The phrase "embryonic stage of plant development" refers to a process that produces a plant embryo from a fertilized ovule by asymmetric cell division and the differentiation of undifferentiated cells into tissues and organs. It occurs during seed development, when the single-celled zygote undergoes a programmed pattern of cell division resulting in a mature embryo.

The term "heterologous" when used in reference to a gene refers to a gene that is not in its natural environment (in other words, has been altered by the hand of man). For example, a heterologous gene includes a gene from one species introduced into another species. A heterologous gene also includes a gene native to an organism that has been altered in some way (for example, mutated, added in multiple copies, linked to a non-native promoter or enhancer sequence, etc.). Heterologous genes may comprise plant gene sequences that comprise cDNA forms of a plant gene; the cDNA sequences may be expressed in either a sense (to produce mRNA) or anti-sense orientation (to produce an anti-sense RNA transcript that is complementary to the mRNA transcript). Heterologous genes are distinguished from endogenous plant genes in that the heterologous gene sequences are typically joined to nucleotide sequences comprising regulatory elements such as promoters that are not found naturally associated with the gene for the protein encoded by the heterologous gene or with plant gene sequences in the chromosome, or are associated with portions of the chromosome not found in nature (for example, genes expressed in loci where the gene is not normally expressed).

The term "oligonucleotide" refers to a molecule comprising two or more deoxyribonucleotides or ribonucleotides, preferably more than three, and usually more than ten. The exact size will depend on many factors, which in turn depends on the ultimate function or use of the oligonucleotide. The oligonucleotide may be generated in any manner, including chemical synthesis, DNA replication, reverse transcription, or a combination thereof.

The term "nucleotide sequence of interest" or "nucleic acid sequence of interest" refers to any nucleotide sequence (for example, RNA or DNA), the manipulation of which may be deemed desirable for any reason (for example, treat disease, confer improved qualities, etc.), by one of ordinary skill in the art. Such nucleotide sequences include, but are not limited to, coding sequences of structural genes (for example, reporter genes, selection marker genes, oncogenes, drug resistance genes, growth factors, etc.), and non-coding regulatory sequences which do not encode an mRNA or protein product (for example, promoter sequence, polyadenylation sequence, termination sequence, enhancer sequence, etc.).

The term "structural" when used in reference to a gene or to a nucleotide or nucleic acid sequence refers to a gene or a nucleotide or nucleic acid sequence whose ultimate expression product is a protein (such as an enzyme or a structural protein), an rRNA, an sRNA, a tRNA, etc.

The term "fragment" or "portion" when used in reference to an oligonucleotide sequence or a nucleic acid sequence refers to a length of the sequence which is less than the entire length as it occurs naturally (for example, as a DNA, RNA, or cDNA molecule). The fragments may range in size from a few nucleotides to the entire nucleic acid sequence minus one nucleotide. Thus, "a nucleotide comprising at least a portion of a gene" may comprise fragments of the gene or the entire gene.

The term "an oligonucleotide having a nucleotide sequence encoding a gene" or "a nucleic acid sequence encoding" a specified gene product refers to a nucleic acid sequence comprising the coding region of a gene or in other words the nucleic acid sequence which encodes a gene product. The coding region may be present in either a cDNA, genomic DNA or RNA form. When present in a DNA form, the oligonucleotide may be single-stranded (in other words, the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

The term "recombinant" when made in reference to a nucleic acid molecule refers to a nucleic acid molecule which comprises segments of nucleic acid joined together by means of molecular biological techniques. The term "recombinant" when made in reference to a protein or a polypeptide refers to a protein molecule which is expressed using a recombinant nucleic acid molecule.

The terms "complementary" and "complementarity" refer to polynucleotides (in other words, a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids.

The term "homology" when used in relation to nucleic acids refers to a degree of complementarity. There may be partial homology or complete homology (in other words, identity). "Sequence identity" refers to a measure of relatedness between two or more nucleic acids or proteins, and is given as a percentage with reference to the total comparison length. The identity calculation takes into account those nucleotide or amino acid residues that are identical and in the same relative positions in their respective larger sequences. Calculations of identity may be performed by algorithms contained within computer programs such as "GAP" (Genetics Computer Group, Madison, Wis.) and "ALIGN" (DNAStar, Madison, Wis.). A partially complementary sequence is one that at least partially inhibits (or competes with) a completely complementary sequence from hybridizing to a target nucleic acid and is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (in other words, the hybridization) of a sequence which is completely homologous to a target under conditions of low stringency. This is not to say that conditions of low stringency are such that non-specific binding is permitted; low stringency conditions require that the binding of two sequences to one another be a specific (in other words, selective) interaction. The absence of non-specific binding may be tested by the use of a second target which lacks even a partial degree of complementarity (for example, less than about 30% identity); in the absence of non-specific binding the probe will not hybridize to the second non-complementary target.

The following terms are used to describe the sequence relationships between two or more polynucleotides: "reference sequence", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA sequence given in a sequence listing or may comprise a complete gene sequence. Generally, a reference sequence is at least 20 nucleotides in length, frequently at least 25 nucleotides in length, and often at least 50 nucleotides in length. Since two polynucleotides may each (1) comprise a sequence (in other words, a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window", as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window may comprise additions or deletions (in other words, gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (Smith and Waterman, Adv. Appl. Math 2: 482 (1981) [7]) by the homology alignment algorithm of Needleman and Wunsch (Needleman and Wunsch, J. Mol. Biol. 48:443 (1970) [8]), by the search for similarity method of Pearson and Lipman (Pearson and Lipman, Proc. Natl. Acad. Sci. (U.S.A.) 85:2444 (1988) [9]), by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (in other words, resulting in the highest percentage of homology over the comparison window) generated by the various methods is selected. The term "sequence identity" means that two polynucleotide sequences are identical (in other words, on a nucleotide-by-nucleotide basis) over the window of comparison. The term "percentage of sequence identity" is calculated by comparing two optimally aligned sequences over the window of comparison, determining the number of positions at which the identical nucleic acid base (for example, A, T, C, G, U, or I) occurs in both sequences to yield the number of matched positions, dividing the number of matched positions by the total number of positions in the window of comparison (in other words, the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of the full-length sequences of the compositions claimed in the present invention.

The term "substantially homologous" when used in reference to a double-stranded nucleic acid sequence such as a cDNA or genomic clone refers to any probe that can hybridize to either or both strands of the double-stranded nucleic acid sequence under conditions of low to high stringency as described below.

The term "substantially homologous" when used in reference to a single-stranded nucleic acid sequence refers to any probe that can hybridize (in other words, it is the complement of) the single-stranded nucleic acid sequence under conditions of low to high stringency as described below.

The term "hybridization" refers to the pairing of complementary nucleic acids. Hybridization and the strength of hybridization (in other words, the strength of the association between the nucleic acids) is impacted by such factors as the degree of complementary between the nucleic acids, stringency of the conditions involved, the Tm of the formed hybrid, and the G:C ratio within the nucleic acids. A single molecule that contains pairing of complementary nucleic acids within its structure is said to be "self-hybridized."

The term "Tm" refers to the "melting temperature" of a nucleic acid. The melting temperature is the temperature at which a population of double-stranded nucleic acid molecules becomes half dissociated into single strands. The equation for calculating the Tm of nucleic acids is well known in the art. As indicated by standard references, a simple estimate of the $T_m$ value may be calculated by the equation: $T_m=81.5+0.41$ (% G+C), when a nucleic acid is in aqueous solution at 1 M NaCl (See for example, Anderson and Young, Quantitative Filter Hybridization, in Nucleic Acid Hybridization (1985) [10]). Other references include more sophisticated computations that take structural as well as sequence characteristics into account for the calculation of $T_m$.

The term "stringency" refers to the conditions of temperature, ionic strength, and the presence of other compounds such as organic solvents, under which nucleic acid hybridizations are conducted. With "high stringency" conditions, nucleic acid base pairing will occur only between nucleic acid fragments that have a high frequency of complementary base sequences. Thus, conditions of "low" stringency are often required with nucleic acids that are derived from organisms that are genetically diverse, as the frequency of complementary sequences is usually less.

"Low stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.1% SDS, 5×Denhardt's reagent (50×Denhardt's contains per 500 ml: 5 g Ficoll (Type 400, Pharmacia), 5 g BSA (Fraction V; Sigma)) and 100 µg/ml denatured salmon sperm DNA followed by washing in a solution comprising 5×SSPE, 0.1% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.5% SDS, 5×Denhardt's reagent and 100 µg/ml denatured salmon sperm DNA followed by washing in a solution comprising 1.0×SSPE, 1.0% SDS at 42° C. when a probe of about 500 nucleotides in length is employed.

"High stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.5% SDS, 5×Denhardt's reagent and 100 µg/ml denatured salmon sperm DNA followed by washing in a solution comprising 0.1× SSPE, 1.0% SDS at 42° C. when a probe of about 500 nucleotides in length is employed.

It is well known that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (for example, the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (for example, increasing the temperature of the hybridization and/or wash steps, the use of formamide in the hybridization solution, etc.).

"Amplification" is a special case of nucleic acid replication involving template specificity. It is to be contrasted with non-specific template replication (in other words, replication that is template-dependent but not dependent on a specific template). Template specificity is here distinguished from fidelity of replication (in other words, synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Q-replicase, MDV-1 RNA is the specific template for the replicase (Kacian et al., Proc. Natl. Acad. Sci. USA, 69:3038 (1972) [11]). Other nucleic acid will not be replicated by this amplification enzyme. Similarly, in the case of T7 RNA polymerase, this amplification enzyme has a stringent specificity for its own promoters (Chamberlin et al., Nature, 228:227 (1970) [12]). In the case of T4 DNA ligase, the enzyme will not ligate the two oligonucleotides or polynucleotides, where there is a mismatch between the oligonucleotide or polynucleotide substrate and the template at the ligation junction (Wu and Wallace, Genomics, 4:560 (1989) [13]). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.), PCR Technology, Stockton Press (1989) [14]).

The term "amplifiable nucleic acid" refers to nucleic acids that may be amplified by any amplification method. It is contemplated that "amplifiable nucleic acid" will usually comprise "sample template."

The term "sample template" refers to nucleic acid originating from a sample that is analyzed for the presence of "target" (defined below). In contrast, "background template" is used in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

The term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (in other words, in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

The term "probe" refers to an oligonucleotide (in other words, a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular gene sequences. It is contemplated that any probe used in the present invention will be labelled with any "reporter molecule," so that is detectable in any detection system, including, but not limited to enzyme (for example, ELISA, as well as enzyme-based histochemical assays), fluorescent, radioactive, and luminescent systems. It is not intended that the present invention be limited to any particular detection system or label.

The term "target," when used in reference to the polymerase chain reaction, refers to the region of nucleic acid bounded by the primers used for polymerase chain reaction. Thus, the "target" is sought to be sorted out from other nucleic acid sequences. A "segment" is defined as a region of nucleic acid within the target sequence.

The term "polymerase chain reaction" ("PCR") refers to the method of K. B. Mullis U.S. Pat. Nos. 4,683,195, 4,683,202, and 4,965,188, that describe a method for increasing the concentration of a segment of a target sequence in a mixture of genomic DNA without cloning or purification [15-17]. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (in other words, denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

With PCR, it is possible to amplify a single copy of a specific target sequence in genomic DNA to a level detectable by several different methodologies (for example, hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications.

The terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

The term "amplification reagents" refers to those reagents (deoxyribonucleotide triphosphates, buffer, etc.), needed for amplification except for primers, nucleic acid template, and the amplification enzyme. Typically, amplification reagents along with other reaction components are placed and contained in a reaction vessel (test tube, microwell, etc.).

The term "reverse-transcriptase" or "RT-PCR" refers to a type of PCR where the starting material is mRNA. The starting mRNA is enzymatically converted to complementary DNA or "cDNA" using a reverse transcriptase enzyme. The cDNA is then used as a "template" for a "PCR" reaction.

The term "gene expression" refers to the process of converting genetic information encoded in a gene into RNA (for example, mRNA, rRNA, tRNA, or snRNA) through "transcription" of the gene (in other words, via the enzymatic action of an RNA polymerase), and into protein, through "translation" of mRNA. Gene expression can be regulated at many stages in the process. "Up-regulation" or "activation" refers to regulation that increases the production of gene expression products (in other words, RNA or protein), while "down-regulation" or "repression" refers to regulation that decrease production. Molecules (for example, transcription factors) that are involved in up-regulation or down-regulation are often called "activators" and "repressors," respectively.

The terms "in operable combination", "in operable order" and "operably linked" refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "regulatory element" refers to a genetic element which controls some aspect of the expression of nucleic acid sequences. For example, a promoter is a regulatory element which facilitates the initiation of transcription of an operably linked coding region. Other regulatory elements are splicing signals, polyadenylation signals, termination signals, etc. By "promoter" is meant a regulatory region of DNA capable of regulating the transcription of a sequence linked thereto. It usually comprises a TATA box capable of directing RNA polymerase II to initiate RNA synthesis at the appropriate transcription initiation site for a particular coding sequence. The promoter is the minimal sequence sufficient to direct transcription in a desired manner. The term "regulatory region" is also used to refer to the sequence capable of initiating transcription in a desired manner. By "seed preferred" is intended favored expression in the seed of the plant, and "embryo preferred" indicates favored expression in the embryo of the seed of the plant.

Transcriptional control signals in eukaryotes comprise "promoter" and "enhancer" elements. Promoters and enhancers consist of short arrays of DNA sequences that interact specifically with cellular proteins involved in transcription (Maniatis, et al., Science 236:1237, 1987 [18]). Promoter and enhancer elements have been isolated from a variety of eukaryotic sources including genes in yeast, insect, mammalian and plant cells. Promoter and enhancer elements have also been isolated from viruses and analogous control elements, such as promoters, are also found in prokaryotes. The selection of a particular promoter and enhancer depends on the cell type used to express the protein of interest. Some eukaryotic promoters and enhancers have a broad host range while others are functional in a limited subset of cell types (for review, see Voss, et al., Trends Biochem. Sci., 11:287, 1986 [19]; and Maniatis, et al., supra 1987 [18]).

The terms "promoter element," "promoter," or "promoter sequence" refer to a DNA sequence that is located at the 5' end (in other words precedes) of the coding region of a DNA polymer. The location of most promoters known in nature precedes the transcribed region. The promoter functions as a switch, activating the expression of a gene. If the gene is activated, it is said to be transcribed, or participating in transcription. Transcription involves the synthesis of mRNA from the gene. The promoter, therefore, serves as a transcriptional regulatory element and also provides a site for initiation of transcription of the gene into mRNA.

The term "regulatory region" refers to a gene's 5' transcribed but untranslated regions, located immediately downstream from the promoter and ending just prior to the translational start of the gene.

The term "promoter region" refers to the region immediately upstream of the coding region of a DNA polymer, and is typically between about 500 bp and 4 kb in length, and is preferably about 1 to 1.5 kb in length. A promoter region controls or regulates transcription of a gene to which it is operably linked, either naturally or by recombinant nucleic acid technology. A promoter region may include smaller sequences which are effective to control or regulate transcription. One skilled in the art can determine such smaller sequences by creating fragments of decreasing size from a promoter region, and operably linking such fragments to a reporter gene, and determining expression of such constructs in transgenic tissue, as described further herein.

Promoters may be tissue specific or cell specific. The term "tissue specific" as it applies to a promoter refers to a promoter that is capable of directing selective expression of a nucleotide sequence of interest to a specific type of tissue (for example, seeds) in the relative absence of expression of the same nucleotide sequence of interest in a different type of tissue (for example, leaves). Tissue specificity of a promoter may be evaluated by, for example, operably linking a reporter gene to the promoter sequence to generate a reporter construct, introducing the reporter construct into the genome of a plant such that the reporter construct is integrated into every tissue of the resulting transgenic plant, and detecting the expression of the reporter gene (for example, detecting mRNA, protein, or the activity of a protein encoded by the reporter gene) in different tissues of the transgenic plant. The detection of a greater level of expression of the reporter gene in one or more tissues relative to the level of expression of the reporter gene in other tissues shows that the promoter is specific for the tissues in which greater levels of expression are detected. The term "cell type specific" as applied to a promoter refers to a promoter which is capable of directing selective expression of a nucleotide sequence of interest in a specific type of cell in the relative absence of expression of the same nucleotide sequence of interest in a different type of cell within the same tissue. The term "cell type specific" when applied to a promoter also means a promoter capable of promoting selective expression of a nucleotide sequence of interest in a region within a single tissue. Cell type specificity of a promoter may be assessed using methods well known in the art, for example, immunohistochemical staining Briefly, tissue sections are embedded in paraffin, and paraffin sections are reacted with a primary antibody which is specific for the polypeptide product encoded by the nucleotide sequence of interest whose expression is controlled by the promoter. A labeled (for example, peroxidase conjugated) secondary antibody which is specific for the primary antibody is allowed to bind to the sectioned tissue and specific binding detected (for example, with avidin/biotin) by microscopy.

A promoter is "effective" as a tissue specific or cell type promoter when expression in the presence of the promoter is greater in the tissue or cell type than expression in the presence of the promoter in other tissues or cell types. Preferably, the greater level of expression is at least about two-fold greater; more preferably, it is at least about four-fold greater; and most preferably, it is at least about ten-fold greater. An effective promoter may comprise all of the promoter region, or a modification or fragment of a promoter region, or a motif of a promoter region.

A "seed-specific promoter" is a promoter which controls or regulates expression of a gene to which it is operably linked in a seed or seed tissue; such expression may occur in developing seed tissue only, at differing times or levels, or in mature seed tissue, or in both. Preferably, expression of the gene in seed tissue is greater than in non-seed tissue when under control of a seed-specific promoter. Preferably, the greater level of expression is at least about two-fold greater; more preferably, it is at least about four-fold greater; and most preferably, it is at least about ten-fold greater.

The term "preferential expression" or "preferentially expressed" refers to expression at a higher level in the particular plant tissue than in other plant tissue. Examples of these types of promoters include seed preferred expression such as that provided by the phaseolin promoter (Bustos et al. 1989 [20]), and the maize globulin-1 gene. A gene which is preferentially expressed in seeds or seed tissue is expressed at a higher level than it is in non-seed tissue. Preferably, expression of the gene in seed tissue is greater than in non-seed tissue. Preferably, the greater level of expression is at least about two-fold greater; more preferably, it is at least about four-fold greater; and most preferably, it is at least about ten-fold greater.

Promoters may be constitutive or inducible. The term "constitutive" when made in reference to a promoter means that the promoter is capable of directing transcription of an operably linked nucleic acid sequence in the absence of a stimulus (for example, heat shock, chemicals, light, etc.). Typically, constitutive promoters are capable of directing expression of a transgene in substantially any cell and any tissue. Exemplary constitutive plant promoters include, but are not limited to SD Cauliflower Mosaic Virus (CaMV SD; see for example, U.S. Pat. No. 5,352,605 [21], incorporated herein by reference), mannopine synthase, octopine synthase (ocs), superpromoter (see for example, WO 95/14098 [22]), and ubi3 (see for example, Garbarino and Belknap, Plant Mol. Biol. 24:119-127 (1994) [23]) promoters. Such promoters have been used successfully to direct the expression of heterologous nucleic acid sequences in transformed plant tissue.

In contrast, an "inducible" promoter is one which is capable of directing a level of transcription of an operably linked nucleic acid sequence in the presence of a stimulus (for example, heat shock, chemicals, light, etc.) which is different from the level of transcription of the operably linked nucleic acid sequence in the absence of the stimulus.

The enhancer and/or promoter may be "endogenous" or "exogenous" or "heterologous." An "endogenous" enhancer or promoter is one that is naturally linked with a given gene in the genome. An "exogenous" or "heterologous" enhancer or promoter is one that is placed in juxtaposition to a gene by means of genetic manipulation (in other words, molecular biological techniques) such that transcription of the gene is directed by the linked enhancer or promoter. For example, an endogenous promoter in operable combination with a first gene can be isolated, removed, and placed in operable combination with a second gene, thereby making it a "heterologous promoter" in operable combination with the second gene. A variety of such combinations are contemplated (for example, the first and second genes can be from the same species, or from different species).

The term "naturally linked" or "naturally located" when used in reference to the relative positions of nucleic acid sequences means that the nucleic acid sequences exist in nature in the relative positions.

The presence of "splicing signals" on an expression vector often results in higher levels of expression of the recombinant transcript in eukaryotic host cells. Splicing signals mediate the removal of introns from the primary RNA transcript and consist of a splice donor and acceptor site (Sambrook, et al., *Molecular Cloning: A Laboratory Manual,* 2nd ed., Cold Spring Harbor Laboratory Press, New York (1989) pp. 16.7-16.8 [24]). A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly(A) site" or "poly(A) sequence" as used herein denotes a DNA sequence which directs both the termination and polyadenylation of the nascent RNA transcript. Efficient polyadenylation of the recombinant transcript is desirable, as transcripts lacking a poly(A) tail are unstable and are rapidly degraded. The poly(A) signal utilized in an expression vector may be "heterologous" or "endogenous." An endogenous poly(A) signal is one that is found naturally at the 3' end of the coding region of a given gene in the genome. A heterologous poly(A) signal is one which has been isolated from one gene and positioned 3' to another gene. A commonly used heterologous poly(A) signal is the SV40 poly (A) signal. The SV40 poly(A) signal is contained on a 237 bp BamHI/BclI restriction fragment and directs both termination and polyadenylation (Sambrook, supra, at 16.6-16.7 [24]).

The term "termination signal" or "termination sequence" refers to a 3' non-translated DNA sequence which functions in plant cells to cause the addition of polyadenylated ribonucleotides to the 3' end of an mRNA sequence transcribed from a gene; the gene may be an endogenous or native gene, or it may be a heterologous gene. The termination sequence may be endogenous or heterologous to the gene.

The term "vector" refers to nucleic acid molecules that transfer DNA segment(s) from one cell to another. The term "vehicle" is sometimes used interchangeably with "vector."

The terms "expression vector" or "expression cassette" refer to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The term "transfection" refers to the introduction of foreign DNA into cells. Transfection may be accomplished by a variety of means known to the art including calcium phosphate-DNA co-precipitation, DEAE-dextran-mediated transfection, polybrene-mediated transfection, glass beads, electroporation, microinjection, liposome fusion, lipofection, protoplast fusion, viral infection, biolistics (in other words, particle bombardment) and the like.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of Graham and van der Eb (Graham and van der Eb, Virol., 52:456 (1973) [25]), has been modified by several groups to optimize conditions for particular types of cells. The art is well aware of these numerous modifications.

The terms "infecting" and "infection" when used with a bacterium refer to co-incubation of a target biological sample, (for example, cell, tissue, etc.) with the bacterium under conditions such that nucleic acid sequences contained within the bacterium are introduced into one or more cells of the target biological sample.

The term "*Agrobacterium*" refers to a soil-borne, Gram-negative, rod-shaped phytopathogenic bacterium which causes crown gall. The term "*Agrobacterium*" includes, but is not limited to, the strains *Agrobacterium tumefaciens*, (which typically causes crown gall in infected plants), and *Agrobacterium rhizogens* (which causes hairy root disease in infected host plants). Infection of a plant cell with *Agrobacterium* generally results in the production of opines (for example, nopaline, agropine, octopine etc.) by the infected cell. Thus, *Agrobacterium* strains which cause production of nopaline (for example, strain LBA4301, C58, A208, GV3101) are referred to as "nopaline-type" Agrobacteria; *Agrobacterium* strains which cause production of octopine (for example, strain LBA4404, Ach5, B6) are referred to as "octopine-type" Agrobacteria; and *Agrobacterium* strains which cause production of agropine (for example, strain EHA105, EHA101, A281) are referred to as "agropine-type" Agrobacteria.

The terms "bombarding, "bombardment," and "biolistic bombardment" refer to the process of accelerating particles towards a target biological sample (for example, cell, tissue, etc.) to effect wounding of the cell membrane of a cell in the target biological sample and/or entry of the particles into the target biological sample. Methods for biolistic bombardment are known in the art (for example, U.S. Pat. No. 5,584,807 [26], the contents of which are incorporated herein by reference), and are commercially available (for example, the helium gas-driven microprojectile accelerator (PDS-1000/He, BioRad).

The term "microwounding" when made in reference to plant tissue refers to the introduction of microscopic wounds in that tissue. Microwounding may be achieved by, for example, particle bombardment as described herein.

The term "transgene" refers to a foreign gene that is placed into an organism by the process of transfection. The term "foreign gene" refers to any nucleic acid (for example, gene sequence) that is introduced into the genome of an organism by experimental manipulations and may include gene sequences found in that organism so long as the introduced gene does not reside in the same location as does the naturally-occurring gene.

The term "transgenic" when used in reference to a plant or fruit or seed (in other words, a "transgenic plant" or "transgenic fruit" or a "transgenic seed") refers to a plant or fruit or seed that contains at least one heterologous or foreign gene in one or more of its cells. The term "transgenic plant material" refers broadly to a plant, a plant structure, a plant tissue, a plant seed or a plant cell that contains at least one heterologous gene in one or more of its cells.

The term "host cell" refers to any cell capable of replicating and/or transcribing and/or translating a heterologous gene. Thus, a "host cell" refers to any eukaryotic or prokaryotic cell (for example, bacterial cells such as *E. coli*, yeast cells, mammalian cells, avian cells, amphibian cells, plant cells, fish cells, and insect cells), whether located in vitro or in vivo. For example, host cells may be located in a transgenic animal.

The terms "transformants" or "transformed cells" include the primary transformed cell and cultures derived from that cell without regard to the number of transfers. All progeny may not be precisely identical in DNA content, due to deliberate or inadvertent mutations. Mutant progeny that have the same functionality as screened for in the originally transformed cell are included in the definition of transformants.

The term "selectable marker" refers to a gene which encodes an enzyme having an activity that confers resistance to an antibiotic or drug upon the cell in which the selectable marker is expressed, or which confers expression of a trait which can be detected (for example, luminescence or fluorescence). Selectable markers may be "positive" or "negative." Examples of positive selectable markers include the neomycin phosphotransferase (NPTII) gene which confers resistance to G418 and to kanamycin, and the bacterial hygromycin phosphotransferase gene (hyg), which confers resistance to the antibiotic hygromycin. Negative selectable markers encode an enzymatic activity whose expression is cytotoxic to the cell when grown in an appropriate selective medium. For example, the HSV-tk gene is commonly used as a negative selectable marker. Expression of the HSV-tk gene in cells grown in the presence of gancyclovir or acyclovir is cytotoxic; thus, growth of cells in selective medium containing gancyclovir or acyclovir selects against cells capable of expressing a functional HSV TK enzyme.

The term "reporter gene" refers to a gene encoding a protein that may be assayed. Examples of reporter genes include, but are not limited to, luciferase (See for example, deWet et al., Mol. Cell. Biol. 7:725 (1987) [27] and U.S. Pat. No. 6,074,859 [28]; U.S. Pat. No. 5,976,796 [29]; U.S. Pat. No. 5,674,713 [30]; and U.S. Pat. No. 5,618,682 [31]; all of which are incorporated herein by reference), green fluorescent protein (for example, GenBank Accession Number U43284 [SEQ ID NO: 12]; a number of GFP variants are commercially available from CLONTECH Laboratories, Palo Alto, Calif.), chloramphenicol acetyltransferase, β-galactosidase, alkaline phosphatase, and horse radish peroxidase.

The term "wild-type" when made in reference to a nucleic acid sequence refers to a nucleic acid sequence which has the characteristics of the sequence isolated from a naturally occurring source. The term "wild-type" when made in reference to a gene product refers to a gene product which has the characteristics of a gene product isolated from a naturally occurring source. The term "naturally-occurring" as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring. A wild-type gene is that which is most frequently observed in a population and is thus arbitrarily designated the "normal" or "wild-type" form of the gene. In contrast, the term "modified" or "mutant" when made in reference to a nucleic acid sequence (such as a regulatory sequence or a sequence encoding a gene) or to a gene product refers, respectively, to a nucleic acid sequence or to a gene product which displays modifications in sequence and/or functional properties (in other words, altered characteristics) when compared to the wild-type gene or gene product. Modifications include additions or deletions of the units making up the nucleic acid sequence or gene product (a unit is, for example, a nucleotide), or substitutions of at least one of the units. It is noted that naturally-occurring mutants can be isolated; these are identified by the fact that they have altered characteristics when compared to the wild-type nucleic acid sequence or gene product.

The term "antisense" refers to a deoxyribonucleotide sequence whose sequence of deoxyribonucleotide residues is in reverse 5' to 3' orientation in relation to the sequence of deoxyribonucleotide residues in a sense strand of a DNA duplex. A "sense strand" of a DNA duplex refers to a strand in a DNA duplex which is transcribed by a cell in its natural state into a "sense mRNA." Thus an "antisense" sequence is a sequence having the same sequence as the non-coding strand in a DNA duplex. The term "antisense RNA" refers to a RNA transcript that is complementary to all or part of a target primary transcript or mRNA and that blocks the expression of a target gene by interfering with the processing, transport and/or translation of its primary transcript or mRNA. The complementarity of an antisense RNA may be with any part of the specific gene transcript, in other words, at the 5' non-coding sequence, 3' non-coding sequence, introns, or the coding sequence. In addition, as used herein, antisense RNA may contain regions of ribozyme sequences that increase the efficacy of antisense RNA to block gene expression. "Ribozyme" refers to a catalytic RNA and includes sequence-specific endoribonucleases. "Antisense inhibition" refers to the production of antisense RNA transcripts capable of preventing the expression of the target protein.

The term "overexpression" refers to the production of a gene product in transgenic organisms that exceeds levels of production in normal or non-transformed organisms. The term "cosuppression" refers to the expression of a foreign gene which has substantial homology to an endogenous gene resulting in the suppression of expression of both the foreign and the endogenous gene. As used herein, the term "altered levels" refers to the production of gene product(s) in transgenic organisms in amounts or proportions that differ from that of normal or non-transformed organisms.

The terms "Southern blot analysis" and "Southern blot" and "Southern" refer to the analysis of DNA on agarose or acrylamide gels in which DNA is separated or fragmented according to size followed by transfer of the DNA from the gel to a solid support, such as nitrocellulose or a nylon membrane. The immobilized DNA is then exposed to a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (Sambrook et al. (1989) *Molecular Cloning: A Laboratory Manual* (Cold Spring Harbor Press, NY), pp 9.31-9.58 [32]).

The term "Northern blot analysis" and "Northern blot" and "Northern" refer to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (J. Sambrook, et al. (1989) supra, pp 7.39-7.52 [33]).

The terms "Western blot analysis" and "Western blot" and "Western" refers to the analysis of protein(s) (or polypeptides) immobilized onto a support such as nitrocellulose or a membrane. A mixture comprising at least one protein is first separated on an acrylamide gel, and the separated proteins are then transferred from the gel to a solid support, such as nitrocellulose or a nylon membrane. The immobilized proteins are exposed to at least one antibody with reactivity against at least one antigen of interest. The bound antibodies may be detected by various methods, including the use of radiolabelled antibodies.

The term "antigenic determinant" refers to that portion of an antigen that makes contact with a particular antibody (in other words, an epitope). When a protein or fragment of a protein is used to immunize a host animal, numerous regions of the protein may induce the production of antibodies that bind specifically to a given region or three-dimensional structure on the protein; these regions or structures are referred to as antigenic determinants. An antigenic determinant may compete with the intact antigen (in other words, the "immunogen" used to elicit the immune response) for binding to an antibody.

The term "isolated" when used in relation to a nucleic acid, as in "an isolated oligonucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids, such as DNA and RNA, are found in the state they exist in nature. For example, a given DNA sequence (for example, a gene) is found on the host cell chromosome in proximity to neighboring genes; RNA sequences, such as a specific mRNA sequence encoding a specific protein, are found in the cell as a mixture with numerous other mRNAs which encode a multitude of proteins. However, isolated nucleic acid encoding a particular protein includes, by way of example, such nucleic acid in cells ordinarily expressing the protein, where the nucleic acid is in a chromosomal location different from that of natural cells, or is otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide will contain at a minimum the sense or coding strand (in other words, the oligonucleotide may single-stranded), but may contain both the sense and anti-sense strands (in other words, the oligonucleotide may be double-stranded).

The term "purified" refers to molecules, either nucleic or amino acid sequences that are removed from their natural environment, isolated or separated. An "isolated nucleic acid sequence" is therefore a purified nucleic acid sequence. "Substantially purified" molecules are at least 60% free, preferably at least 75% free, and more preferably at least 90% free from other components with which they are naturally associated. As used herein, the term "purified" or "to purify" also refer to the removal of contaminants from a sample. The removal of contaminating proteins results in an increase in the percent of polypeptide of interest in the sample. In another example, recombinant polypeptides are expressed in plant, bacterial, yeast, or mammalian host cells and the polypeptides are purified by the removal of host cell proteins; the percent of recombinant polypeptides is thereby increased in the sample.

The term "sample" is used in its broadest sense. In one sense, it can refer to a plant cell or tissue. In another sense, it is meant to include a specimen or culture obtained from any source, as well as biological and environmental samples. Biological samples may be obtained from plants or animals (including humans) and encompass fluids, solids, tissues, and gases. Environmental samples include environmental material such as surface matter, soil, water, and industrial samples. These examples are not to be construed as limiting the sample types applicable to the present invention.

ABBREVIATIONS

DAP: Days after pollination; qRT-PCR: Quantitative real time polymerase chain reaction; ABA: Abscisic Acid; GA: Gibberllic Acid; GSNAP: Genomic short-read nucleotide alignment program; FC: Fold-changes; GO: Gene Ontology; RPKM: Reads per kilobase of exon per million mapped reads; TCA: Tricaboxylic Acid Cycle; TAG: Triacylglycerol; LTP: Lipid transfer proteins; LEA: Late embryogenesis abundant; glb2: Globulin 2 gene; SNP: Single nucleotide polymorphism

DESCRIPTION OF THE FIGURES

The accompanying figures, which are incorporated into and form a part of the specification, illustrate several embodiments of the present invention and, together with the description, serve to explain the principles of the invention. The figures are only for the purpose of illustrating a preferred embodiment of the invention and are not to be construed as limiting the invention.

(FIG. 3A) shows cell wall-localized T1 expansin seeds analyzed from 30 lines selected at random from 10 independent transgenic events. (FIG. 3B) shows endoplasmic reticulum (ER)-localized T1 expansin seeds analyzed from 30 lines selected at random from 22 ITEs. (FIG. 3C) shows vacuole-localized T1 expansin seeds analyzed from 30 lines selected at random from 12 ITEs. Expansin activity was calculated as described herein

(FIG. 5A) Single seed assay results of BCG01010.

(FIG. 8A) Various amounts of crude fungal cellulase were used to release glucose from Sigmacell microcrystalline cellulose.

FIG. 15 shows the Bamboo Expansin cDNA (SEQ ID NO: 1) with 3' Histidine tag shown in bold (SEQ ID NO: 2) (without signal sequence). Note the last 9 nucleotides are not a part of the his tag but represent the stop codon (TAA) plus a Sac I restriction endonuclease cloning site.

FIG. 16 shows the Bamboo Expansin genomic DNA (without signal sequence) (SEQ ID NO: 3).

FIG. 17 shows the Cucumber expansin gene (SEQ ID NO: 4).

FIG. 18 shows a *Phyllostachys edulis* cDNA clone: bphyem105j06, full insert sequence, GenBank: FP094161.1 [SEQ ID NO: 9].

DESCRIPTION OF THE INVENTION

Figure 1:
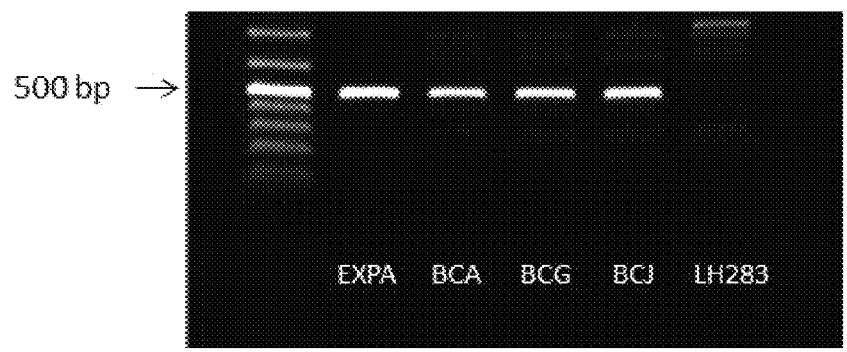
FIG. 1 shows the presence of the expansin gene in transgenic corn lines was confirmed using PCR. One ITE from each vector was screened. EXPA, synthesized cucumber expansin gene in E. coli; BCA, DNA from transgenic line leaf (cell wall); BCG, DNA from transgenic line leaf (ER); BCJ, DNA from transgenic line leaf (vacuole); LH283, DNA from native corn leaf.

Expansin has the impact of reducing the high tension within plant cells, determined to be equivalent to 100 to 1000 atmospheres of tensile stress, as noted in the review by Daniel Cosgrove "Growth of the Plant Cell Wall" Nature Vol. 6 pp 850-861 (November 2005) [34]. This pH-dependent wall loosening protein was named expansin due to its impact on molecular modification of the cell wall that results in relaxation of wall stress and resulting enlargement of the cell wall.

When referring to expansin is meant to include the family of expansin proteins having expansin activity to allow cell wall components to "slip so that fibers can lengthen." See, e.g. Cosgrove et al., U.S. Pat. No. 6,326,470 [35], incorporated herein by reference in its entirety. Expansins disrupt non-covalent binding of wall polysaccharides to one another. They cause wall stress relaxation and extension. This family contrasts with other growth related proteins, and works within seconds of addition to expand cell walls, where endoglucanase requires prolonged exposure before expansion of cell walls. Endoglucanase digestion weakens the cell wall but expansin does not. Expansins promote wall stress relaxation.

The family of proteins has two domains, an N-terminal domain and a C-terminal domain. The N-terminal domain is about 15 kDa and reported to have some similarity to the catalytic domain of the family-45 endoglucanases. The C-terminal domain is about 10 kDa and related to grass pollen allergens. See Cosgrove 2005 [34] at page 855 and citing Cosgrove, "Relaxation in a high-stress environment; the molecular bases of extensible cell walls and cell enlargement" Plant Cell 9:1031-1041 (1997) [36] and Shcherban, "Molecular cloning and sequence analysis of expansins—a highly conserved, multigene family of proteins that mediate cell wall extension in plants" Proc. Natl. Acad. Sci. USA 92:9245-9249 (1995) [37]. Cosgrove reports the polypeptides are salt soluble with a molecular weight of about 29 to 30 kDa as measured by SDS-PAGE. The superfamily consists of four families, two of which extend walls, EXPA, (alpha-expansin) and EXPB (beta-expansin). See Cosgrove (2005) p. 856 [34] and Kende et al. "Nomenclature for members of the expansin superfamily of genes and proteins" Plant Mol. Biol. 55:311-314 (2004) [38]. The EXLA and EXLB subfamily function is unknown.

There has been interest in the ability of expansins to enhance and have a synergistic effect on the ability of cellulases to hydrolyze cellulose tissue. This has many uses, in the production of ethanol or other biofuels, as further described herein, in paper recycling, paper production, and in any variety of uses where enhancement of the breakdown of cellulose is desired.

Attempts have been made for over twenty years to express expansin in a heterologous system with no success or with very little expressed in a living plant system. For example, where heterologous expansin was expressed in tomato such that high levels of expansin activity were extractable from cell walls, growth of the plant was adversely affected. See Rochange et al. "Impaired growth in transgenic plants over-expressing an expansin isoform" *Plant Mol. Biol.* 46:581-589 (2001) [39]. The adverse impact included stunted plants with shorter leaves and internodes, seedlings with shorter and wider hypocotyls compared to wild-type seedlings, and shorter and wider cortical and epidermal cells reflecting change in growth polarity. Expression of the protein at higher levels, in excess of that produced in wild-type plants, presents particular challenges given its strong physiological impact on plant tissue. As noted, excessive transgenic expansin activity can disturb growth in vegetative and fruit tissue and if present in too large quantities disrupt wall organization Cosgrove 2005 [34] at p 587.

The inventors have surprisingly found success in obtaining high expression levels of expansin in plant seeds, and in an embodiment, in corn seed, without harming the host. Instead, the inventors were able to produce a plant that did not exhibit stunted growth, and was capable of producing seed which expressed the expansin at high levels. The plants produced were not stunted, and growth was not observed to be adversely impacted. The plant growth was not adversely inhibited, that is, the plants were not stunted and growth of the plant was not reduced such that the plant was unable to produce higher levels of expansin than wild-type plants, and was able to produce 1 times, two times, three times, four times five times, six times and more expansin than wild-type plants. The plants were capable of producing seed which comprised high levels of expansin, that is, levels in excess of wild-type plants not comprising the heterologous nucleic acid molecule encoding expansin, and at levels which were previously found to adversely impact plants, levels of a six-fold increase in activity over wild-type plants were obtained. A new assay was further developed to determine expansin expression in the plant cells and improved methods of extraction and/or sample preparation allow for even further improved recovery of expansin, as described in more detail below. With the assay, expansin activity is expressed as a ratio of glucose released from cellulose by expansin combined with cellulase compared to glucose released by cellulase alone. Expansin activity using the assay was at least up to 0.50 times, 1.50, 2.50, 3.50, 4.50, 5.50, 6.0 times increased activity compared to wild-type plants not comprising the nucleic acid molecule encoding expansin, and amounts in-between. As described herein, with selection of highest expressing individual and/or pools of seeds, expression levels are expected to increase further, at least five and six fold and up to at least 10-fold more increase over T1 seed where breeding and selection are employed to select higher producing plants and seed.

A preferred embodiment provides that heterologous expansin is preferentially expressed to the seed of the plant, and in a further embodiment, is expressed to the embryo or germ of the plant. Expression levels and accumulation of expansin in the seed or embryo is expected to be at least one time higher, at least two times higher, at least three times higher, at least four times higher, at least five times higher, at least six times higher, at least seven times higher, at least eight times higher, at least nine times higher and at least ten times higher and more and amounts in-between, as compared to a seed or embryo not comprising the nucleic acid molecule expressing expansin. Such amounts are also likewise increased as compared to cucumber hypocotyls which is one such tissue available for donating an expansin expressing nucleic acid molecule. Despite the relatively small size of the seed or germ compared to the remainder of plant tissue, high levels of expression were obtained on a dry weight basis, which is at least 0.015% of dry weight of seed, or at least 0.5% total soluble protein. As discussed below, by using grain to recover germ, enzyme concentration can be yet further increased by at least 10 fold, increasing the amount of expansin produced to at least 1.0% total soluble protein (TSP), at least 5% TSP, at least 10% TSP and amounts in-between and higher. The expression on a dry weight basis is increased to at least 0.1% dry weight of seed, at least 1% dry weight of seed and amounts in-between and higher.

In one embodiment, the heterologous expansin expression is directed to the vacuole, cell wall or endoplasmic reticulum. An embodiment provides the expression is directed to the endoplasmic reticulum.

An embodiment further provides that the heterologous expansin is expressed in a monocotyledonous plant. A further embodiment provides that the plant is corn. Without wishing to be bound by any theory, it is believed that monocotyledonous plants, and particularly corn, surprisingly allow expansin expression without causing such adverse impact to the plant that the plant cannot grow sufficiently and/or cannot provide higher levels of expression of expansin.

The expansin activity assay described here determines synergistic activity of the addition of the expansin to cellulase with cellulose. A glucose oxidase assay is used to detect glucose released from cellulose as a result of the expansin added to cellulase. This activity may be compared to endogenous protein extract.

The expansin protein from transgenic seed, in an embodiment, is fractionated and enriched. By way of example, without intending to be limiting, in an embodiment measurements are conducted of the amount of glucose produced compared to a control, with only cellulose provided; cellulose plus cellulase (such as commercially available cellulase); transgenic expansin without cellulase; expansin with cellulose and cellulase; and may also include controls of expansin transgenic corn extract; native or wild-type corn extract. Expansin activity may be expressed as a ratio of glucose released from cellulose with expansin added to a cellulase.

In one embodiment of the invention, recovery of expansin protein activity from plant tissue is considerably improved by reducing salt concentration to prevent inhibition of activity of cellulase and glucose oxidase. In one embodiment, NaCl concentration for the extraction buffer ranged from 0 (no NaCl) up to no more than 300 mM. In a preferred embodiment, the concentration is 150 mM or less and in another embodiment is 0.

The amount of sample extract in an embodiment is about at least 5 to at least 50 μg and in another embodiment is 20 μg of extracted protein.

An embodiment provides for an incubation time of no more than two hours, in another embodiment no more than one hour and in a preferred embodiment is no more than 0.5 hours.

Yet another embodiment provides the NaCl concentration is 0 to no more than 300 mM, the amount of sample extract is 20 μg and incubation time is 0.5 hours.

It is anticipated the process of producing expansin may be used with monocotyledonous or dicotyledonous plants. Examples of monocotyledonous plants are plants which belong to the genus of *Avena* (oat), *Triticum* (wheat), *Secale* (rye), *Hordeum* (barley), *Oryza* (rice), *Panicum, Pennisetum, Setaria, Sorghum* (millet), *Zea* (maize). Dicotyledonous useful plants are, inter alia, leguminous plants, such as legumes and especially alfalfa and soybean, as well as non-legumes rape, tomato, sugar beet, and potato.

By a "crop plant" is intended any plant that is cultivated for the purpose of producing plant material that is sought after by man for either oral consumption, or for utilization in an industrial, pharmaceutical, or commercial process. The invention may be applied to any of a variety of plants, including, but not limited to maize, wheat, rice, barley, soybean, cotton, sorghum, beans in general, rape/canola, alfalfa, flax, sunflower, safflower, millet, rye, sugarcane, sugar beet, cocoa, tea, *Brassica*, cotton, coffee, sweet potato, flax, peanut, clover; vegetables such as lettuce, tomato, cucurbits, cassava, potato, carrot, radish, pea, lentils, cabbage, cauliflower, broccoli, Brussels sprouts, peppers, and pineapple, conifers and other trees, tree fruits such as citrus, apples, pears, peaches, apricots, walnuts, avocado, banana, and coconut; and flowers such as orchids, carnations and roses.

The enzymes used in saccharification processes currently encompass enzymes that can be employed to degrade plant cell wall polysaccharides into fermentable sugars. Such enzymes are known in the art and include, but are not limited to, enzymes that can catalyze the degradation of cellulose, hemicellulose, and/or pectin. In particular, the methods of the invention are drawn to cellulose-degrading enzymes. By "cellulose-degrading enzyme" is intended any enzyme that can be utilized to promote the degradation of cellulose into fermentable sugars including, but not limited to, cellulases and glucosidases. By way of example, without limitation, the enzymes classified in Enzyme Classification as 3.2.1.x are included within the scope of the process. An example of the many enzymes which may be employed in the invention is presented in Table 1, a list of enzymes in the category by the Nomenclature Committee of the International Union of Biochemistry and Molecular Biology (NC-IUBMB).

TABLE 1

Polysaccharide degrading enzymes

EC 3.2.1.1 α-amylase
EC 3.2.1.2 β-amylase
EC 3.2.1.3 glucan 1,4-α-glucosidase
EC 3.2.1.4 cellulase
EC 3.2.1.6 endo-1,3(4)-β-glucanase
EC 3.2.1.7 inulinase
EC 3.2.1.8 endo-1,4-β-xylanase
EC 3.2.1.10 oligo-1,6-glucosidase
EC 3.2.1.11 dextranase
EC 3.2.1.14 chitinase
EC 3.2.1.15 polygalacturonase
EC 3.2.1.17 lysozyme
EC 3.2.1.18 exo-α-sialidase
EC 3.2.1.20 α-glucosidase
EC 3.2.1.21 β-glucosidase
EC 3.2.1.22 α-galactosidase
EC 3.2.1.23 β-galactosidase
EC 3.2.1.24 α-mannosidase
EC 3.2.1.25 β-mannosidase
EC 3.2.1.26 β-fructofuranosidase
EC 3.2.1.28 αα-trehalase
EC 3.2.1.31 β-glucuronidase
EC 3.2.1.32 xylan endo-1,3-β-xylosidase
EC 3.2.1.33 amylo-1,6-glucosidase
EC 3.2.1.35 hyaluronoglucosaminidase
EC 3.2.1.36 hyaluronoglucuronidase
EC 3.2.1.37 xylan 1,4-β-xylosidase
EC 3.2.1.38 β-D-fucosidase
EC 3.2.1.39 glucan endo-1,3-β-D-glucosidase
EC 3.2.1.40 α-L-rhamnosidase
EC 3.2.1.41 pullulanase
EC 3.2.1.42 GDP-glucosidase
EC 3.2.1.43 β-L-rhamnosidase
EC 3.2.1.44 fucoidanase
EC 3.2.1.45 glucosylceramidase
EC 3.2.1.46 galactosylceramidase
EC 3.2.1.47 galactosylgalactosylglucosylceramidase
EC 3.2.1.48 sucrose α-glucosidase
EC 3.2.1.49 α-N-acetylgalactosaminidase
EC 3.2.1.50 α-N-acetylglucosaminidase
EC 3.2.1.51 α-L-fucosidase
EC 3.2.1.52 β-L-N-acetylhexosaminidase
EC 3.2.1.53 β-N-acetylgalactosaminidase
EC 3.2.1.54 cyclomaltodextrinase
EC 3.2.1.55 α-N-arabinofuranosidase
EC 3.2.1.56 glucuronosyl-disulfoglucosamine glucuronidase
EC 3.2.1.57 isopullulanase
EC 3.2.1.58 glucan 1,3-β-glucosidase
EC 3.2.1.59 glucan endo-1,3-α-glucosidase
EC 3.2.1.60 glucan 1,4-α-maltotetraohydrolase
EC 3.2.1.61 mycodextranase
EC 3.2.1.62 glycosylceramidase TABLE 1-continued Polysaccharide degrading enzymes EC 3.2.1.63 1,2-α-L-fucosidase
EC 3.2.1.64 2,6-β-fructan 6-levanbiohydrolase
EC 3.2.1.65 levanase
EC 3.2.1.66 quercitrinase
EC 3.2.1.67 galacturan 1,4-α-galacturonidase
EC 3.2.1.68 isoamylase
EC 3.2.1.70 glucan 1,6-α-glucosidase
EC 3.2.1.71 glucan endo-1,2-β-glucosidase
EC 3.2.1.72 xylan 1,3-β-xylosidase
EC 3.2.1.73 licheninase
EC 3.2.1.74 glucan 1,4-β-glucosidase
EC 3.2.1.75 glucan endo-1,6-β-glucosidase
EC 3.2.1.76 L-iduronidase
EC 3.2.1.77 mannan 1,2-(1,3)-α-mannosidase
EC 3.2.1.78 mannan endo-1,4-β-mannosidase
EC 3.2.1.80 fructan β-fructosidase
EC 3.2.1.81 agarase
EC 3.2.1.82 exo-poly-α-galacturonosidase
EC 3.2.1.83 κ-carrageenase
EC 3.2.1.84 glucan 1,3-β-glucosidase
EC 3.2.1.85 6-phospho-β-galactosidase
EC 3.2.1.86 6-phospho-β-glucosidase
EC 3.2.1.87 capsular-polysaccharide endo-1,3-α-galactosidase
EC 3.2.1.88 β-L-arabinosidase
EC 3.2.1.89 arabinogalactan endo-1,4-β-galactosidase
EC 3.2.1.91 cellulose 1,4-β-cellobiosidase
EC 3.2.1.92 peptidoglycan β-N-acetylmuramidase
EC 3.2.1.93 αα-phosphotrehalase
EC 3.2.1.94 glucan 1,6-α-isomaltosidase
EC 3.2.1.95 dextran 1,6-α-isomaltotriosidase
EC 3.2.1.96 mannosyl-glycoprotein endo-β-N-acetylglucosaminidase
EC 3.2.1.97 glycopeptide α-N-acetylgalactosaminidase
EC 3.2.1.98 glucan 1,4-α-maltohexaosidase
EC 3.2.1.99 arabinan endo-1,5-α-L-arabinosidase
EC 3.2.1.100 mannan 1,4-mannobiosidase
EC 3.2.1.101 mannan endo-1,6-α-mannosidase
EC 3.2.1.102 blood-group-substance endo-1,4-β-galactosidase
EC 3.2.1.103 keratan-sulfate endo-1,4-β-galactosidase
EC 3.2.1.104 steryl-β-glucosidase
EC 3.2.1.105 strictosidine β-glucosidase
EC 3.2.1.106 mannosyl-oligosaccharide glucosidase
EC 3.2.1.107 protein-glucosylgalactosylhydroxylysine glucosidase
EC 3.2.1.108 lactase
EC 3.2.1.109 endogalactosaminidase
EC 3.2.1.110 mucinaminylserine mucinaminidase
EC 3.2.1.111 1,3-α-L-fucosidase
EC 3.2.1.112 2-deoxyglucosidase
EC 3.2.1.113 mannosyl-oligosaccharide 1,2-α-mannosidase
EC 3.2.1.114 mannosyl-oligosaccharide 1,3-1,6-α-mannosidase
EC 3.2.1.115 branched-dextran exo-1,2-α-glucosidase
EC 3.2.1.116 glucan 1,4-α-maltotriohydrolase
EC 3.2.1.117 amygdalin β-glucosidase
EC 3.2.1.118 prunasin β-glucosidase
EC 3.2.1.119 vicianin β-glucosidase
EC 3.2.1.120 oligoxyloglucan β-glycosidase
EC 3.2.1.121 polymannuronate hydrolase
EC 3.2.1.122 maltose-6'-phosphate glucosidase
EC 3.2.1.123 endoglycosylceramidase
EC 3.2.1.124 3-deoxy-2-octulosonidase
EC 3.2.1.125 raucaffricine β-glucosidase
EC 3.2.1.126 coniferin β-glucosidase
EC 3.2.1.127 1,6-α-L-fucosidase
EC 3.2.1.128 glycyrrhizinate β-glucuronidase
EC 3.2.1.129 endo-α-sialidase
EC 3.2.1.130 glycoprotein endo-α-1,2-mannosidase
EC 3.2.1.131 xylan α-1,2-glucuronosidase
EC 3.2.1.132 chitosanase
EC 3.2.1.133 glucan 1,4-α-maltohydrolase
EC 3.2.1.134 difructose-anhydride synthase
EC 3.2.1.135 neopullulanase
EC 3.2.1.136 glucuronoarabinoxylan endo-1,4-β-xylanase
EC 3.2.1.137 mannan exo-1,2-1,6-β-mannosidase
EC 3.2.1.139 α-glucuronidase
EC 3.2.1.140 lacto-N-biosidase
EC 3.2.1.141 4-α-D-[(1→4)-α-D-glucano]trehalose trehalohydrolase
EC 3.2.1.142 limit dextrinase
EC 3.2.1.143 poly(ADP-ribose) glycohydrolase
EC 3.2.1.144 3-deoxyoctulosonase TABLE 1-continued Polysaccharide degrading enzymes EC 3.2.1.145 galactan 1,3-β-galactosidase
EC 3.2.1.146 β-galactofuranosidase
EC 3.2.1.147 thioglucosidase
EC 3.2.1.149 β-primeverosidase
EC 3.2.1.150 oligoxyloglucan reducing-end-specific cellobiohydrolase
EC 3.2.1.151 xyloglucan-specific endo-β-1,4-glucanase
EC 3.2.1.152 mannosylglycoprotein endo-β-mannosidase
EC 3.2.1.153 fructan β-(2,1)-fructosidase
EC 3.2.1.154 fructan β-(2,6)-fructosidase
EC 3.2.1.156 oligosaccharide reducing-end xylanase For the degradation of cellulose, two types of exoglucanase have been described that differ in their approach to the cellulose chain. One type attacks the non-reducing end and the other attacks the reducing end. Cellulase enzymes which cleave the cellulose chain internally are referred to as endo-β-1,4-glucanases (E.C. 3.2.1.4) and serve to provide new reducing and non-reducing chain termini on which exo-β-1,4-glucanases (cellobiohydrolase, CBH; E.C. 3.2.1.91) can operate (Tomme et al. (1995) *Microbial Physiology* 37:1-81 [40]). The product of the exoglucanase reaction is typically cellobiose, so a third activity, β-D-glucosidase (E.C. 3.2.1.21), is required to cleave cellobiose to glucose. The exoglucanase can also yield longer glucose chains (up to 6 glucose units) that will require a β-D-glucosidase activity to reduce their size. Relative to the other enzyme activities needed for degradation of cellulose into fermentable sugars, only a minor amount of the β-D-glucosidase activity is required. In brief, current processes to produce fermentable sugars involve the addition to a cellulose-containing composition an endocellulase (endo-β-1,4-glucanases) which cleaves the cellulose chain internally and an exocellulase (exo-β-1,4-glucanases) which cleaves the free ends of the cellulose chain. In order to produce the end product of glucose, a third enzyme is involved, a glucosidase (β-D-glucosidases), which acts on the cellobiose to produce glucose. When referring to a cellulase in this instance is meant any of the above enzymes, whether an endocellulase, exocellulase, β-D glucosidase, or any other enzyme that degrades cellulose.

Here, one uses the expansin proteins of the invention to increase the degradation and glucose production rate as, by unfolding the crystalline cellulose to make it more available so the enzymes can degrade it more efficiently. Cosgrove (1999) *Annu Rev Plant Physiol Plant Mol Biol* 50:391-417 [41]. Increased amounts of glucose may be produced compared to a process in which the transgenic expansin is not added to the cellulase and cellulose and/or the amount of cellulase enzyme(s) or number of different cellulase enzymes needed to produce the same amount of glucose may be reduced or eliminated compared to the process where the expansin is not added, thereby saving costs of the process.

When using a plant, tissue, parts or cells expressing a heterologous cellulose degrading enzyme as the source of an exogenous cellulose degrading enzyme, the plant can be used in a commercial process. When using the seed itself, it can, for example, be made into flour and then applied in the commercial process. Extraction from biomass can be accomplished by known methods. Downstream processing for any production system refers to all unit operations after product synthesis, in this case protein production in transgenic seed (Kusnadi, A. R., Nikolov, Z. L., Howard, J. A., 1997. *Biotechnology and Bioengineering.* 56:473-484 [42]). Seed is processed either as whole seed ground into flour, or fractionated and the germ separated from the hulls and endosperm. If germ is used, it is usually defatted using a hexane extraction or other process such as cold pressing and the remaining crushed germ ground into a meal or flour. In some cases the germ is used directly in the industrial process or the protein can be extracted (See, e.g. WO 98/39461 [43]). Extraction is generally made into aqueous buffers at specific pH to enhance recombinant protein extraction and minimize native seed protein extraction.

In addition to the assay described here, any convenient means of detecting presence of the protein of interest may be used. For example, a Western analysis is a variation of the Southern analysis technique. With a Southern analysis, DNA is cut with restriction endonucleases and fractionated on an agarose gel to separate the DNA by molecular weight and then transferring to nylon membranes. It is then hybridized with the probe fragment which was radioactively labeled with $^{32}P$ and washed in an SDS solution. In the Western analysis, instead of isolating DNA, the protein of interest is extracted and placed on an acrylamide gel. The protein is then blotted onto a membrane and contacted with a labeling substance. See e.g., Hood et al., "Commercial Production of Avidin from Transgenic Maize; Characterization of Transformants, Production, Processing, Extraction and Purification" *Molecular Breeding* 3:291-306 (1997) [44]. The ELISA or enzyme linked immunoassay has been known since 1971. In general, antigens solubilized in a buffer are coated on a plastic surface. When serum is added, antibodies can attach to the antigen on the solid phase. The presence or absence of these antibodies can be demonstrated when conjugated to an enzyme. Adding the appropriate substrate will detect the amount of bound conjugate which can be quantified. A common ELISA assay is one which uses biotinylated anti-(protein) polyclonal antibodies and an alkaline phosphatase conjugate. For example, an ELISA used for quantitative determination of laccase levels can be an antibody sandwich assay, which utilizes polyclonal rabbit antibodies obtained commercially. The antibody is conjugated to alkaline phosphatases for detection. In another example, an ELISA assay to detect trypsin or trypsinogen uses biotinylated anti-trypsin or anti-trypsinogen polyclonal antibodies and a streptavidin-alkaline phosphatase conjugate.

When referring to a plant tissue composition is meant any plant part, plant tissue (which can be optionally ground, sieved, pulverized, chopped, sliced, minced, ground, crushed, mashed or soaked or the like as long as the cellulose degradation enhancing property is retained) or extract and when referring to plant seed or plant germ tissue is meant any part, tissue (which can be optionally ground, sieved, pulverized, chopped, sliced, minced, ground, crushed, mashed or soaked or the like as long as the cellulose degradation enhancing property is retained) or extract of the seed or germ. Further, it is not meant to imply the entire plant seed or germ must be used or that plant tissue or cells must be present in the composition in the final extract where an extract is provided as long as plant cells are used to produce the extract. In an embodiment the tissue composition is seed or germ tissue composition. Such plant seed tissue can include the whole seed or its parts, including pericarp (kernel or hull), embryo (called the germ in processing language), or endosperm. In a preferred embodiment, the plant tissue is embryo plant tissue or extract. The plant seed tissue may be in another embodiment a grain seed or part thereof. In yet another embodiment, the plant tissue is a corn seed tissue or part thereof, such as, for example, an embryo that is also referred to as the germ. When referring to tissue is meant an aggregate of cells that can constitute structure(s) or component(s) of the plant, or which can be a portion of such structure or component, or which are from more than one such structure or organ. Seed tissue can be whole seed, portions of the seed, and ground or pulverized or otherwise processed in a manner that is convenient. The tissue composition in one embodiment can be a suspension of plant cells. As noted, the tissue composition can also be provided as an extract. Any of the many available means to prepare such an extract can be employed. When referring to an extract is meant the general process of placing tissue/cells in a liquid, preferably a buffer (the tissue may be optionally ground or otherwise pre-treated), and removing the supernatant.

The cellulosic biomass can originate from the same plants as the expansin producing plant tissue or from different plants. In an embodiment, the cellulosic biomass comprises plant residues. More preferably, in one embodiment, the cellulosic biomass comprises crop residues normally left in the field after the harvest of corn grain, which is also known as corn stover. Most preferably, the cellulosic biomass comprises corn stover that is from the same plants as the cell wall polysaccharide-degrading enzyme substitute and/or enzymes for increased cost efficiency.

As is apparent to one skilled in the art, any nucleic acid molecule encoding an expansin may be used in the process. Further, known nucleotide sequences can be used to isolate corresponding sequences from other organisms, particularly other plants, or to synthesize synthetic sequences. In this manner, methods such as PCR, hybridization, synthetic gene construction and the like can be used to identify or generate such sequences based on their sequence homology to the sequences set forth herein. Sequences identified, isolated or constructed based on their sequence identity to the whole of or any portion of an expansin-encoding sequence may be employed. In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed (Sambrook et al., 1989 [45]; Innis et al., 1990 [46]; Innis et al., 1995 [47]; Innis et al., 1999 [46]). Known methods of PCR include, but are not limited to, methods using paired primers, nested primers, degenerate primers, gene-specific primers, vector-specific primers, partially-mismatched primers, and the like. Once isolated, many methods are available for one skilled in the art to detect expansin expression.

When the nucleic acid is prepared or altered synthetically, advantage can be taken of known codon preferences of the intended host where the nucleic acid is to be expressed. For example, although nucleic acid sequences of the present invention may be expressed in both monocotyledonous and dicotyledonous plant species, sequences can be modified to account for the specific codon preferences and GC content preferences of monocotyledons or dicotyledons as these preferences have been shown to differ (Murray et al. *Nucl. Acids Res.* 17:477-498 (1989) [48]). Thus, the maize preferred codon for a particular amino acid may be derived from known gene sequences from maize. Maize codon usage for 28 genes from maize plants is listed in Table 4 of Murray et al., supra. [48].

With reference to nucleic acid molecules, the term "isolated nucleic acid" is sometimes used. This term, when applied to DNA, refers to a DNA molecule that is separated from sequences with which it is immediately contiguous (in the 5' and 3' directions) in the naturally occurring genome of the organism from which it was derived. For example, the isolated nucleic acid may comprise a DNA molecule inserted into a vector, such as a plasmid or virus vector, or integrated into the genomic DNA of a prokaryote or eukaryote. An isolated nucleic acid molecule may also comprise a cDNA molecule.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the DNA sequences of the invention. Methods for preparation of probes for hybridization and for construction of cDNA and genomic libraries are generally known in the art and are disclosed (Sambrook et al., 1989 [45]).

For example, an expansin-encoding nucleic acid sequence, or one or more portions thereof, may be used as a probe capable of specifically hybridizing to corresponding sequences. To achieve specific hybridization under a variety of conditions, such probes include sequences that are unique among the sequences to be screened and are preferably at least about 10 nucleotides in length, and most preferably at least about 20 nucleotides in length. Such sequences may alternatively be used to amplify corresponding sequences from a chosen plant by PCR. This technique may be used to isolate sequences from a desired plant or as a diagnostic assay to determine the presence of sequences in a plant. Hybridization techniques include hybridization screening of DNA libraries plated as either plaques or colonies (Sambrook et al., 1989 [45]).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulfate) at 37° C., and a wash in 1× to 2×SSC (20.times.SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1.0 M NaCl, 1% SDS at 37° C., and a wash in 0.1×SSC at 60 to 65° C.

Specificity is also the function of post-hybridization washes, the critical factors being the ionic strength and temperature of the final wash solution. For DNA-DNA hybrids, the $T_m$ can be approximated from the equation $T_m=81.5°$ C.$+16.6$ (log M)$+0.41$ (% GC)$-0.61$ (% form.)$-500/L$, where M is the molarity of monovalent cations, % GC is the percentage of guanosine and cytosine nucleotides in the DNA, % form. is the percentage of formamide in the hybridization solution, and L is the length of the hybrid in base pairs (Meinkoth and Wahl, 1984 [49]). The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted for sequences of the desired identity to hybridize. For example, if sequences with 90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11 to 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Ausubel et al. (1993) [50] and Sambrook et al. (1989) [45].

Thus, isolated sequences that have expansin activity (increasing degradation of cellulose in the presence of a cellulase) and which hybridize under stringent conditions to a known sequence, or to fragments thereof may be employed.

The following terms are used to describe the sequence relationships between two or more nucleic acids or polynucleotides: (a) "reference sequence", (b) "comparison window", (c) "sequence identity" and (d) "percentage of sequence identity."

(a) As used herein, "reference sequence" is a defined sequence used as a basis for sequence comparison. A reference sequence may be a subset or the entirety of a specified sequence; for example, as a segment of a full-length promoter sequence, or the complete promoter sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to accurately reflect the similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a mathematical algorithm.

Optimal alignment of sequences for comparison can use any means to analyze sequence identity (homology) known in the art, e.g., by the progressive alignment method of termed "PILEUP" (Morrison, (1997) *Mol. Biol. Evol.* 14:428-441 [51], as an example of the use of PILEUP); by the local homology algorithm of Smith & Waterman (*Adv. Appl. Math.* 2: 482 (1981) [7]); by the homology alignment algorithm of Needleman & Wunsch (*J. Mol. Biol.* 48:443-453 (1970) [8]); by the search for similarity method of Pearson (*Proc. Natl. Acad. Sci. USA* 85: 2444 (1988)[9]); by computerized implementations of these algorithms (e.g., GAP, BEST FIT, FASTA, and TFASTA in the Wisconsin Genetics Software Package, Genetics Computer Group, 575 Science Dr., Madison, Wis.); ClustalW (CLUSTAL in the PC/Gene program by Intelligenetics, Mountain View, Calif., described by, e.g., Higgins (1988), *Gene* 73: 237-244 [52]; Corpet (1988), *Nucleic Acids Res.* 16:10881-10890 [53]; Huang, *Computer Applications in the Biosciences* 8:155-165 (1992) [54]; and Pearson (1994), *Methods in Mol. Biol.* 24:307-331) [55]; Pfam (Sonnhammer (1998), *Nucleic Acids Res.* 26:322-325) [56]; TreeAlign (Hein (1994), *Methods Mol. Biol.* 25:349-364) [57]; MEG-ALIGN, and SAM sequence alignment computer programs; or, by manual visual inspection.

Another example of an algorithm that is suitable for determining sequence similarity is the BLAST algorithm, which is described in Altschul et al, (1990) *J. Mol. Biol.* 215: 403-410 [58]. The BLAST programs (Basic Local Alignment Search Tool) of Altschul, S. F., et al., (1990) *J. Mol. Biol.* 215:403-410 [58]) searches under default parameters for identity to sequences contained in the BLAST "GENEMBL" database. A sequence can be analyzed for identity to all publicly available DNA sequences contained in the GENEMBL database using the BLASTN algorithm under the default parameters.

Software for performing BLAST analyses is publicly available through the National Center for Biotechnology Information; see also Zhang (1997), *Genome Res.* 7:649-656 [59] for the "PowerBLAST" variation. This algorithm involves first identifying high scoring sequence pairs (HSPs) by identifying short words of length W in the query sequence that either match or satisfy some positive valued threshold score T when aligned with a word of the same length in a database sequence. T is referred to as the neighborhood word score threshold (Altschul et al. (1990), *J. Mol. Biol.* 215: 403-410 [58]). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a wordlength (W) of 11, the BLOSUM62 scoring matrix (see Henikoff (1992), *Proc. Natl. Acad. Sci. USA* 89:10915-10919 [60]) alignments (B) of 50, expectation (E) of 10, M=5, N=−4, and a comparison of both strands. The term BLAST refers to the BLAST algorithm which performs a statistical analysis of the similarity between two sequences; see, e.g., Karlin (1993), *Proc. Natl. Acad. Sci. USA* 90:5873-5787 [61]. One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

In an embodiment, GAP (Global Alignment Program) can be used. GAP uses the algorithm of Needleman and Wunsch (*J. Mol. Biol.* 48:443-453, 1970) [8] to find the alignment of two complete sequences that maximizes the number of matches and minimizes the number of gaps. Default gap creation penalty values and gap extension penalty values in the commonly used Version 10 of the Wisconsin Package® (Accelrys, Inc., San Diego, Calif.) for protein sequences are 8 and 2, respectively. For nucleotide sequences the default gap creation penalty is 50 while the default gap extension penalty is 3. Percent Similarity is the percent of the symbols that are similar. Symbols that are across from gaps are ignored. A similarity is scored when the scoring matrix value for a pair of symbols is greater than or equal to 0.50, the similarity threshold. A general purpose scoring system is the BLOSUM62 matrix (Henikoff and Henikoff (1993), *Proteins* 17: 49-61 [62]), which is currently the default choice for BLAST programs. BLOSUM62 uses a combination of three matrices to cover all contingencies. Altschul, J. Mol. Biol. 36: 290-300 (1993) [63], herein incorporated by reference in its entirety and is the scoring matrix used in Version 10 of the Wisconsin Package® (Accelrys, Inc., San Diego, Calif.) (see Henikoff & Henikoff (1989) *Proc. Natl. Acad. Sci. USA* 89:10915 [60]).

(c) As used herein, "sequence identity" or "identity" in the context of two nucleic acid sequences makes reference to the residues in the two sequences that are the same when aligned for maximum correspondence over a specified comparison window.

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base occurs in both sequences to yield the number of matched positions, dividing the number of matched positions by the total number of positions in the window of comparison, and multiplying the result by 100 to yield the percentage of sequence identity.

Identity to a sequence would mean a polynucleotide sequence having at least 65% sequence identity, more preferably at least 70% sequence identity, more preferably at least 75% sequence identity, more preferably at least 80% identity, more preferably at least 85% 86%, 87%, 88%, 89%, 90%, 91%, 92%, 93%, 94%, 95%, 96%, 97%, 98%, 99% sequence identity.

Such nucleic acid molecule can also include functional variants of a known sequence. Functional variants include, for example sequences having one or more nucleotide substitutions, deletions or insertions and wherein the variant retains expansin activity, particularly the ability to enhance cellulose degradation with cellulases. Functional variants can be created by any of a number of methods available to one skilled in the art, such as by site-directed mutagenesis, induced mutation, identified as allelic variants, cleaving through use of restriction enzymes, or the like. Activity can likewise be measured by any variety of techniques, including measurement of synergistic activity as described herein.

The invention further encompasses a "functional fragment" that is a fragment formed by one or more deletions from a larger sequence yet retains expansin activity. Activity can be measured as described herein. See for example, Sambrook et al. (1989) [45]. Functional fragments can be obtained by use of restriction enzymes to cleave the naturally occurring nucleotide sequences; by synthesizing a nucleotide sequence from the naturally occurring DNA sequence; or can be obtained through the use of PCR technology. See particularly, Mullis et al. (1987) [64] and Erlich, editor. (1989) [14].

The expansin encoding sequence(s) may be combined with any number of other components to be introduced into the plant, including combined with another gene of interest or nucleic acid sequence of interest to be expressed in the plant. The "gene of interest" or "nucleic acid sequence of interest" refers to a nucleic acid that may encode a desired polypeptide or protein but also may refer to a nucleic acid that does not constitute an entire gene, and which does not necessarily encode a polypeptide or protein. For example, when used in a homologous recombination process, the promoter may be placed in a construct with a sequence that targets an area of the chromosome in the plant but may not encode a protein. As used herein, the terms nucleic acid of interest or polynucleotide refer to deoxyribonucleotides or ribonucleotides and polymers thereof in either single- or double-stranded form. As such, the terms include RNA and DNA, which can be a gene or a portion thereof, a cDNA, a synthetic polydeoxyribonucleic acid sequence, or the like, and can be single-stranded or double-stranded, as well as a DNA/RNA hybrid. Furthermore, the terms are used herein to include naturally-occurring nucleic acid molecules, which can be isolated from a cell, as well as synthetic molecules, which can be prepared, for example, by methods of chemical synthesis or by enzymatic methods such as by the polymerase chain reaction (PCR). Unless specifically limited, the terms encompass nucleic acids containing known analogues of natural nucleotides that have similar binding properties as the reference nucleic acid and are metabolized in a manner similar to naturally occurring nucleotides. The term nucleic acid is used interchangeably with gene, cDNA, and mRNA encoded by a gene.

Unless otherwise indicated, when referring to a particular nucleic acid sequence, it also implicitly encompasses conservatively modified variants thereof (e.g. degenerate codon substitutions) and complementary sequences as well as the sequence explicitly indicated.

The term conservatively modified variants applies to both amino acid and nucleic acid sequences. With respect to particular nucleic acid sequences, conservatively modified variants refers to those nucleic acids which encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine Thus, at every position where an alanine is specified by a codon, the codon can be altered to any of the corresponding codons described without altering the encoded polypeptide. Such nucleic acid variations are silent variations and represent one species of conservatively modified variation. Every nucleic acid sequence herein that encodes a polypeptide also, by reference to the genetic code, describes every possible silent variation of the nucleic acid. One of ordinary skill will recognize that each codon in a nucleic acid (except AUG, which is ordinarily the only codon for methionine; and UGG, which is ordinarily the only codon for tryptophan) can be modified to yield a functionally identical molecule. Accordingly, each silent variation of a nucleic acid which encodes a polypeptide of the present invention is implicit in each described polypeptide sequence and is within the scope of the present invention.

A construct is a package of genetic material inserted into the genome of a cell via various techniques.

As used herein, the term vector refers broadly to any plasmid or virus encoding an exogenous nucleic acid. The term should also be construed to include non-plasmid and non-viral compounds which facilitate transfer of nucleic acid into virions or cells, such as, for example, polylysine compounds and the like. The vector may be a viral vector that is suitable as a delivery vehicle for delivery of the nucleic acid, or mutant thereof, to a cell, or the vector may be a non-viral vector which is suitable for the same purpose. Examples of viral and non-viral vectors for delivery of DNA to cells and tissues are well known in the art and are described, for example, in Ma et al. (1997, Proc. Natl. Acad. Sci. U.S.A. 94:12744-12746 [65]). Examples of viral vectors include, but are not limited to, a recombinant vaccinia virus, a recombinant adenovirus, a recombinant retrovirus, a recombinant adeno-associated virus, a recombinant avian pox virus, and the like (Cranage et al., 1986, EMBO J. 5:3057-3063 [66]; International Patent Application No. WO94/17810, published Aug. 18, 1994 [67]; International Patent Application No. WO94/23744, published Oct. 27, 1994 [68]). Examples of non-viral vectors include, but are not limited to, liposomes, polyamine derivatives of DNA, and the like.

In general, the methods available for construction of recombinant genes, optionally comprising various modifications for improved expression, can differ in detail. However, conventionally employed methods include PCR amplification, or the designing and synthesis of overlapping, complementary synthetic oligonucleotides, which are annealed and ligated together to yield a gene with convenient restriction sites for cloning, or subcloning from another already cloned source, or cloning from a library. The methods involved are standard methods for a molecular biologist (Sambrook et al., 1989 [45]).

A variety of components may be included in the vector to be introduced into a plant cell, as one skilled in the art appreciates. A promoter is used to drive expression of the expansin encoding nucleic acid molecule and the same or different promoters may be used to drive other included components. In an embodiment the promoter is a promoter that preferentially expresses in the seed of the plant. In another embodiment the promoter is one which preferentially expresses in the embryo or germ of the plant seed. By "promoter" is meant a regulatory region of DNA capable of regulating the transcription of a sequence linked thereto. It usually comprises a TATA box capable of directing RNA polymerase II to initiate RNA synthesis at the appropriate transcription initiation site for a particular coding sequence. The promoter is the minimal sequence sufficient to direct transcription in a desired manner. The term "regulatory region" is also used to refer to the sequence capable of initiating transcription in a desired manner. When referring to preferential expression, what is meant is expression at a higher level in the particular plant tissue than in other plant tissue. When referring to a seed or embryo preferred promoter or a promoter that expresses in a seed or embryo preferred manner is meant that it confers expression to an operably linked sequence to a higher degree in seed tissue than in other parts of the plant or to a higher degree in embryo tissue that in other parts of the seed. The embryo preferred promoter may express during embryo development, along with expression at other stages, may express strongly during embryo development and to a much lesser degree at other times.

Examples of these types of promoters include seed preferred expression such as that provided by the phaseolin promoter (Bustos et al. (1989) The Plant Cell Vol. 1, 839-853 [20]). For dicots, seed-preferred promoters include, but are not limited to, bean β-phaseolin, napin, β-conglycinin, soybean lectin, cruciferin, and the like. For monocots, seed-preferred promoters include, but are not limited to, maize 15 kDa zein, 22 kDa zein, 27 kDa zein, γ-zein, waxy, shrunken 1, shrunken 2, globulin 1, an Ltp1 (See, for example, U.S. Pat. No. 7,550,579 [69]), an Ltp2 (Opsahl-Sorteberg, H-G. et al., (2004) Gene 341:49-58 [70]), and oleosin genes. See also WO 00/12733 [71], where seed-preferred promoters from end1 and end2 genes are disclosed. Seed-preferred promoters also include those promoters that direct gene expression predominantly to specific tissues within the seed such as, for example, the endosperm-preferred promoter of γ-zein, the cryptic promoter from tobacco (Fobert et al. (1994) "T-DNA tagging of a seed coat-specific cryptic promoter in tobacco" Plant J. 4: 567-577 [72]), the P-gene promoter from corn (Chopra et al. (1996) "Alleles of the maize P gene with distinct tissue specificities encode Myb-homologous proteins with C-terminal replacements" Plant Cell 7:1149-1158 [73], Erratum in Plant Cell 1997, 1:109 [73]), promoters that direct expression to the seed coat or hull of corn kernels, for example the pericarp-specific glutamine synthetase promoter (Muhitch et al., (2002) "Isolation of a Promoter Sequence From the Glutamine Synthetase$_{1-2}$ Gene Capable of Conferring Tissue-Specific Gene Expression in Transgenic Maize" Plant Science 163:865-872 [74] and GenBank accession number AF359511 [SEQ ID NO: 10]). Expression to the embryo tissue of the seed is provided in another embodiment. Examples of such promoters include the globulin promoters. One example is the globulin-1 promoter from corn (Belanger and Kriz (1991) "Molecular basis for Allelic Polymorphism of the maize Globulin-1 gene" Genetics 129: 863-972 [75] and GenBank accession No. L22344 [SEQ ID NO: 11]). Another example is the Zea mays extended globulin-1 promoter of U.S. Pat. No. 7,169,967 [76], incorporated herein by reference in its entirety. Still a further example is the globulin-2 promoter, U.S. Pat. No. 7,112,723 [77], also incorporated herein by reference in its entirety. Any convenient seed or embryo preferred promoter may be used in the process.

As used herein, a nucleotide segment is referred to as operably linked when it is placed into a functional relationship with another DNA segment. For example, DNA for a signal sequence is operably linked to DNA encoding a polypeptide if it is expressed as a preprotein that participates in the secretion of the polypeptide; a promoter or enhancer is operably linked to a coding sequence if it stimulates the transcription of the sequence. Operably linked elements may be contiguous or non-contiguous. When used to refer to the joining of two protein coding regions, by operably linked it is intended that the coding regions are in the same reading frame. Alternatively, the additional gene(s) can be provided on multiple expression cassettes. Such an expression cassette is provided with a plurality of restriction sites and/or recombination sites for insertion of the polynucleotide to be under the transcriptional regulation of the regulatory regions.

In one embodiment, the plant marker and the gene of interest can be both functionally linked to the same promoter. In another embodiment, the plant marker and the gene of interest can be functionally linked to different promoters. In yet third and fourth embodiments, the expression vector can contain two or more genes of interest that can be linked to the same promoter or different promoters. For example, the seed or embryo promoter can be used to drive the gene of interest and the marker, or a different promoter used for one or the other. These other promoter elements can be those that are constitutive or sufficient to render promoter-dependent gene expression controllable as being cell-type specific, tissue-specific or time or developmental stage specific, or being inducible by external signals or agents. Such elements may be located in the 5' or 3' regions of the gene. Although the additional promoter may be the endogenous promoter of a structural gene of interest, the promoter can also be a foreign regulatory sequence. Promoter elements employed to control expression of product proteins and the selection gene can be any plant-compatible promoters. These can be plant gene promoters, such as, for example, the ubiquitin promoter (European patent application no. 0 342 926 [78]); the promoter for the small subunit of ribulose-1,5-bis-phosphate carboxylase (ss-RUBISCO) (Coruzzi et al., (1984) Tissue-specific and light-regulated expression of a pea nuclear gene encoding the small subunit of ribulose-1,5-bisphosphate carboxylase. *EMBO J.* 3, 1671-1679 [79]; Broglie et al., (1984) Light-regulated expression of a pea ribulose-1,5-bisphosphate carboxylase small subunit gene in transformed plant cells. *Science* 224, 838-843984 [79]); or promoters from the tumor-inducing plasmids from *Agrobacterium tumefaciens*, such as the nopaline synthase, octopine synthase and mannopine synthase promoters (Velten and Schell, (1985) Selection-expression plasmid vectors for use in genetic transformation of higher plants. *Nucleic Acids Res.* 13, 6981-6998 [80]) that have plant activity; or viral promoters such as the cauliflower mosaic virus (CaMV) 19S and 35S promoters (Guilley et al., 1982 Transcription of Cauliflower mosaic virus DNA: detection of promoter sequences, and characterization of transcripts. *Cell* 30, 763-773 [81]; Odell et al., 1985 Identification of DNA sequences required for activity of the cauliflower mosaic virus 35S promoter. *Nature* 313, 810-812 [82]), the figwort mosaic virus FLt promoter (Maiti et al., 1997 Promoter/leader deletion analysis and plant expression vectors with the figwort mosaic virus (FMV) full length transcript (FLt) promoter containing single or double enhancer domains. *Transgenic Res.* 6, 143-156 [83]) or the coat protein promoter of TMV (Grdzelishvili et al., 2000 Mapping of the tobacco mosaic virus movement protein and coat protein subgenomic RNA promoters in vivo. *Virology* 275, 177-192 [84]). Alternatively, plant promoters such as heat shock promoters for example soybean hsp 17.5-E (Gurley et al., 1986 Upstream sequences required for efficient expression of a soybean heat shock gene. Mol. Cell. Biol. 6, 559-565 [85]); or ethanol-inducible promoters (Caddick et al., 1998 An ethanol inducible gene switch for plants used to manipulate carbon metabolism NatBiotechnol 16(2), 177-180. [86]) may be used. See International Patent Application No. WO 91/19806 [87] for a review of illustrative plant promoters suitably employed in the present invention.

One skilled in the art readily appreciates that the promoter can be used with any of a variety of nucleotide sequences comprising the gene of interest to be expressed in plants. For example, the gene of interest may encode a protein that is useful for industrial or pharmaceutical purposes or the like, or to impact the plant itself, such as through expression of a protein that provides disease resistance, insect resistance, herbicide resistance, or impacts agronomic traits as well as grain quality traits. The sequences used with the promoter can be native or non-native sequences to the plant. DNA sequences native to plants as well as non-native DNA sequences can be transformed into plants and used to modulate levels of native or non-native proteins.

The gene of interest can also be a nucleotide sequence used to target an area of the plant genome through homologous recombination. The promoter may be placed in a construct with such sequence, which sequence will not necessarily encode a protein. The sequence recombines in the genome and the promoter may be placed at the desired site targeted by the sequences to regulate the desired endogenous nucleotide sequence.

Further, the gene of interest can be an mRNA that can be used for a silencing system, such as antisense, and in that instance, no protein is produced. Means of increasing or inhibiting a protein are well known to one skilled in the art and, by way of example, may include, transgenic expression, antisense suppression, co-suppression methods including but not limited to: RNA interference, gene activation or suppression using transcription factors and/or repressors, mutagenesis including transposon tagging, directed and site-specific mutagenesis, chromosome engineering and, homologous recombination. In the case of use with homologous recombination, no in vivo construct will be required.

Once the gene is engineered to contain desired features, such as the desired subcellular localization sequences, it may then be placed into an expression vector by standard methods. The selection of an appropriate expression vector will depend upon the method of introducing the expression vector into host cells. A typical expression vector contains prokaryotic DNA elements coding for a bacterial origin of replication and an antibiotic resistance gene to provide for the growth and selection of the expression vector in the bacterial host; a cloning site for insertion of an exogenous DNA sequence; eukaryotic DNA elements that control initiation of transcription of the exogenous gene (such as the promoter of the invention or another promoter); and DNA elements that control the processing of transcripts, such as transcription termination/polyadenylation sequences. It also can contain such sequences as are needed for the eventual integration of the vector into the plant chromosome.

In addition, markers that facilitate identification of a plant cell containing the polynucleotide encoding the marker may be employed. Scorable or screenable markers are useful, where presence of the sequence produces a measurable product and can produce the product without destruction of the plant cell. Examples include a β-glucuronidase, or uidA gene (GUS), which encodes an enzyme for which various chromogenic substrates are known (for example, U.S. Pat. No. 5,268,463 [88] and U.S. Pat. No. 5,599,670 [89]); chloramphenicol acetyl transferase (Jefferson et al. (1987) *The EMBO Journal* vol. 6 No. 13 pp. 3901-3907 [90]); alkaline phosphatase. Other screenable markers include the anthocyanin/flavonoid genes in general (See discussion at Taylor and Briggs, (1990) *The Plant Cell* 2:115-127 [91]) including, for example, an R-locus gene, which encodes a product that regulates the production of anthocyanin pigments (red color) in plant tissues (Dellaporta et al., in *Chromosome Structure and Function*, Kluwer Academic Publishers, Appels and Gustafson eds., pp. 263-282 (1988)

[92]); the genes which control biosynthesis of flavonoid pigments, such as the maize C1 gene (Kao et al., (1996) *Plant Cell* 8: 1171-1179 [93]; Scheffler et al. (1994) *Mol. Gen. Genet.* 242:40-48 [94]) and maize C2 (Wienand et al., (1986) *Mol. Gen. Genet.* 203:202-207 [95]); the B gene (Chandler et al., (1989) *Plant Cell* 1:1175-1183 [96]), the p1 gene (Grotewold et al, (1991 *Proc. Natl. Acad. Sci* USA) 88:4587-4591 [97]; Grotewold et al., (1994) *Cell* 76:543-553 [98]; Sidorenko et al., (1999) *Plant Mol. Biol.* 39:11-19 [99]); the bronze locus genes (Ralston et al., (1988) *Genetics* 119:185-197 [100]; Nash et al., (1990) *Plant Cell* 2(11): 1039-1049 [101]), among others. Yet further examples of suitable markers include the cyan fluorescent protein (CYP) gene (Bolte et al. (2004) *J. Cell Science* 117: 943-54 [102] and Kato et al. (2002) *Plant Physiol* 129: 931-42 [103]), the yellow fluorescent protein gene (PhiYFP™ from Evrogen; see Bolte et al. (2004) *J. Cell Science* 117: 943-54 [102]); a lux gene, which encodes a luciferase, the presence of which may be detected using, for example, X-ray film, scintillation counting, fluorescent spectrophotometry, low-light video cameras, photon counting cameras or multiwell luminometry (Teeri et al. (1989) *EMBO J.* 8:343 [104]); a green fluorescent protein (GFP) gene (Sheen et al., (1995) *Plant J.* 8(5):777-84 [105]); and DsRed where plant cells transformed with the marker gene are red in color, and thus visually selectable (Dietrich et al. (2002) *Biotechniques* 2(2):286-293 [106]). Additional examples include a p-lactamase gene (Sutcliffe, (1978) *Proc. Nat'l. Acad. Sci. U.S.A.* 75:3737 [107]), which encodes an enzyme for which various chromogenic substrates are known (e.g., PADAC, a chromogenic cephalosporin); a xylE gene (Zukowsky et al., (1983) *Proc. Nat'l. Acad. Sci. U.S.A.* 80:1101 [108]), which encodes a catechol dioxygenase that can convert chromogenic catechols; an α-amylase gene (Ikuta et al., (1990) *Biotech.* 8:241 [109]); and a tyrosinase gene (Katz et al., (1983) *J. Gen. Microbiol.* 129:2703 [110]), which encodes an enzyme capable of oxidizing tyrosine to DOPA and dopaquinone, which in turn condenses to form the easily detectable compound melanin. Clearly, many such markers are available to one skilled in the art.

The expression vector can optionally also contain a signal sequence located between the promoter and the gene of interest and/or after the gene of interest. A signal sequence is a nucleotide sequence, translated to give an amino acid sequence, which is used by a cell to direct the protein or polypeptide of interest to be placed in a particular place within or outside the eukaryotic cell. Many signal sequences are known in the art. See, for example Becker et al., (1992) *Plant Mol. Biol.* 20:49 [111], Knox, C., et al., "Structure and Organization of Two Divergent Alpha-Amylase Genes from Barley", *Plant Mol. Biol.* 9:3-17 (1987) [112], Lerner et al., (1989) *Plant Physiol.* 91:124-129 [113], Fontes et al., (1991) *Plant Cell* 3:483-496 [114], Matsuoka et al., (1991) *Proc. Natl. Acad. Sci.* 88:834 [115], Gould et al., (1989) *J. Cell. Biol.* 108:1657 [116], Creissen et al., (1991) *Plant J.* 2:129 [117], Kalderon, et al., (1984) "A short amino acid sequence able to specify nuclear location," *Cell* 39:499-509 [118], Steifel, et al., (1990) "Expression of a maize cell wall hydroxyproline-rich glycoprotein gene in early leaf and root vascular differentiation" *Plant Cell* 2:785-793 [119]. When targeting the enzyme to the cell wall use of a signal sequence is necessary. One example is the barley alpha-amylase signal sequence. Rogers, J. C. (1985) "Two barley alpha-amylase gene families are regulated differently in aleurone cells" *J. Biol. Chem.* 260: 3731-3738 [120].

In those instances where it is desirable to have the expressed product of the heterologous nucleotide sequence directed to a particular organelle, particularly the plastid, amyloplast, or to the endoplasmic reticulum, or secreted at the cell's surface or extracellularly, the expression cassette can comprise a coding sequence for a transit peptide. Such transit peptides are well known in the art and include, but are not limited to, the transit peptide for the acyl carrier protein, the small subunit of RUBISCO, plant EPSP synthase, *Zea mays* Brittle-1 chloroplast transit peptide (Nelson et al. Plant Physiol 117(4):1235-1252 (1998) [121]; Sullivan et al. Plant Cell 3(12):1337-48 [122]; Sullivan et al., Planta (1995) 196(3):477-84 [123]; Sullivan et al., J. Biol. Chem. (1992) 267(26):18999-9004 [124]) and the like. One skilled in the art will readily appreciate the many options available in expressing a product to a particular organelle Use of transit peptides is well known (e.g., see U.S. Pat. No. 5,717,084 [125]; U.S. Pat. No. 5,728,925 [126]). A protein may be targeted to the endoplasmic reticulum of the plant cell. This may be accomplished by use of a localization sequence, such as KDEL. This sequence (Lys-Asp-Glu-Leu) [SEQ ID NO: 14] contains the binding site for a receptor in the endoplasmic reticulum. (Munro et al., (1987) "A C-terminal signal prevents secretion of luminal ER proteins." *Cell.* 48:899-907 [127]. Retaining the protein in the vacuole is another example. Signal sequences to accomplish this are well known. For example, Raikhel U.S. Pat. No. 5,360,726 [128] shows a vacuole signal sequence as does Warren et al. U.S. Pat. No. 5,889,174 [129]. Vacuolar targeting signals may be present either at the amino-terminal portion, (Holwerda et al., (1992) *The Plant Cell,* 4:307-318 [130], Nakamura et al., (1993) *Plant Physiol.,* 101:1-5 [131]), carboxy-terminal portion, or in the internal sequence of the targeted protein. (Holwerda et al., (1992) *The Plant Cell,* 4:307-318 [130], Saalbach et al. (1991) *The Plant Cell,* 3:695-708 [132]). Additionally, amino-terminal sequences in conjunction with carboxy-terminal sequences are responsible for vacuolar targeting of gene products (Shinshi et al. (1990) *Plant Molec. Biol.* 14:357-368 [133]).

The expression cassette can include one or more enhancers. By "enhancer" is intended a cis-acting sequence that increases the utilization of a promoter. Such enhancers can be native to a gene or from a heterologous gene. Further, it is recognized that some promoters can contain one or more native, enhancers or enhancer-like elements. An example of one such enhancer is the 35S enhancer, which can be a single enhancer, or duplicated. See for example, McPherson et al, U.S. Pat. No. 5,322,938 [134]. Other methods known to enhance translation can also be utilized, for example, introns, and the like.

Where appropriate, the nucleotide sequence may be optimized for increased expression in the transformed plant. That is, nucleic acid sequences can be synthesized using plant-preferred codons for improved expression. See, for example, Campbell and Gowri (1990) *Plant Physiol.* 92: 1-11 [135] for a discussion of host-preferred codon usage. Methods are available in the art for synthesizing plant-preferred genes. See, for example, U.S. Pat. No. 5,380,831 [136], U.S. Pat. No. 5,436,391 [137], and Murray et al. (1989) *Nucl. Acids Res.* 17:477-498 (1989) [48]. Additional sequence modifications are known to enhance gene expression in a plant. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures. In another example, a Kozak or Kozak-like consensus sequence may be used to enhance translation, the full consensus sequence being (GCC)GCC A/G CC ATG G [SEQ ID NO: 13], with a purine (adenine or guanine) three bases upstream of the start codon. See, Kozak (1986) *Cell* 44(2):283-92 [138]; Kozak (1987) *Nucl. Acids Res.* 15(20):8125-8148 [139].

The termination region can be native with the promoter nucleotide sequence utilized, can be native with the DNA sequence of interest, or can be derived from another source. Convenient termination regions are available from the Ti-plasmid of *A. tumefaciens*, such as the octopine synthase (MacDonald et al., (1991) *Nuc. Acids Res.* 19(20)5575-5581 [140]) and nopaline synthase termination regions (Depicker et al., (1982) *Mol. and Appl. Genet.* 1:561-573 [141] and Shaw et al. (1984) *Nucleic Acids Research* Vol. 12, No. 20 pp 7831-7846 [142] (nos)). Examples of various other terminators include the pin II terminator from the protease inhibitor II gene from potato (An, et al. (1989) *Plant Cell* 1, 115-122 [143]. See also, Guerineau et al. (1991) *Mol. Gen. Genet.* 262:141-144 [144]; Proudfoot (1991) *Cell* 64:671-674 [145]; Sanfacon et al. (1991) *Genes Dev.* 5:141-149 [146]; Mogen et al. (1990) *Plant Cell* 2:1261-1272 [147]; Munroe et al. (1990) *Gene* 91:151-158 [148]; Ballas et al. (1989) *Nucleic Acids Res.* 17:7891-7903 [149]; and Joshi et al. (1987) *Nucleic Acid Res.* 15:9627-9639 [150].

Obviously, many variations on the promoters, selectable markers, signal sequences, leader sequences, termination sequences, introns, enhancers and other components of the vector are available to one skilled in the art.

Methods for introducing expression vectors into plant tissue available to one skilled in the art are varied and will depend on the plant selected. Procedures for transforming a wide variety of plant species are well known and described throughout the literature. (See, for example, Miki and McHugh (2004) *Biotechnol.* 107, 193-232 [151]; Klein et al. (1992) *Biotechnology* (NY) 10, 286-291 [152]; and Weising et al. (1988) *Annu. Rev. Genet.* 22, 421-477 [153]). For example, the DNA construct may be introduced into the genomic DNA of the plant cell using techniques such as microprojectile-mediated delivery (Klein et al. 1992, supra [152]), electroporation (Fromm et al., 1985 *Proc. Natl. Acad. Sci. USA* 82, 5824-5828 [154]), polyethylene glycol (PEG) precipitation (Mathur and Koncz, 1998 *Methods Mol. Biol.* 82, 267-276 [155]), direct gene transfer (WO 85/01856 [156]), in vitro protoplast transformation (U.S. Pat. No. 4,684,611 [157]), and microinjection of plant cell protoplasts or embryogenic callus (Crossway, A. (1985) *Mol. Gen. Genet.* 202, 179-185 [158]). *Agrobacterium* transformation methods of Ishida et al. (1996) [159] and also described in U.S. Pat. No. 5,591,616 [160] are yet another option. Co-cultivation of plant tissue with *Agrobacterium tumefaciens* is a variation, where the DNA constructs are placed into a binary vector system (Ishida et al., 1996 *Nat. Biotechnol.* 14, 745-750 [159]). The virulence functions of the *Agrobacterium tumefaciens* host will direct the insertion of the construct into the plant cell DNA when the cell is infected by the bacteria. See, for example, Fraley et al. (1983) *Proc. Natl. Acad. Sci. USA,* 80, 4803-4807 [161]. *Agrobacterium* is primarily used in dicots, but monocots including maize can be transformed by *Agrobacterium*. See, for example, U.S. Pat. No. 5,550,318 [162]. In one of many variations on the method, *Agrobacterium* infection of corn can be used with heat shocking of immature embryos (Wilson et al. U.S. Pat. No. 6,420,630 [163]) or with antibiotic selection of Type II callus (Wilson et al., U.S. Pat. No. 6,919,494 [164]).

Standard methods for transformation of canola are described by Moloney et al. (1989) [165]. Corn transformation is described by Fromm et al. (1990) [166], and Gordon-Kamm et al. (1990) [167]. *Agrobacterium* is primarily used in dicots, but certain monocots such as maize can be transformed by *Agrobacterium*. See, for example, U.S. Pat. No. 5,550,318 [162]. Rice transformation is described by Hiei et al. (1994), and Lee et al. (1991). Wheat can be transformed by techniques similar to those used for transforming corn or rice. Sorghum transformation is described by Casas et al. (1993) [168] and barley transformation is described by Wan and Lemaux (1994) [169]. Soybean transformation is described in a number of publications, including U.S. Pat. No. 5,015,580 [170].

In one method, the *Agrobacterium* transformation methods of Ishida et al. (1996) [159] and also described in U.S. Pat. No. 5,591,616 [160], are generally followed, with modifications that the inventors have found improve the number of transformants obtained. The Ishida method uses the A1188 variety of maize that produces Type I callus in culture. In one preferred embodiment the Hi II maize line is used which initiates Type II embryogenic callus in culture (Armstrong et al., 1991 [171]).

While Ishida recommends selection on phosphinothricin when using the bar or pat gene for selection, another preferred embodiment provides use of bialaphos instead. In general, as set forth in the U.S. Pat. No. 5,591,616 [160], and as outlined in more detail below, dedifferentiation is obtained by culturing an explant of the plant on a dedifferentiation-inducing medium for not less than seven days, and the tissue during or after dedifferentiation is contacted with *Agrobacterium* having the gene of interest. The cultured tissue can be callus, an adventitious embryo-like tissue or suspension cells, for example. In this preferred embodiment, the suspension of *Agrobacterium* has a cell population of $10^6$ to $10^{11}$ cells/ml and are contacted for three to ten minutes with the tissue, or continuously cultured with *Agrobacterium* for not less than seven days. The *Agrobacterium* can contain plasmid pTOK162, with the gene of interest between border sequences of the T region of the plasmid, or the gene of interest may be present in another plasmid-containing *Agrobacterium*. The virulence region may originate from the virulence region of a Ti plasmid or Ri plasmid. The bacterial strain used in the Ishida protocol is LBA4404 with the 40 kb super binary plasmid containing three vir loci from the hypervirulent A281 strain. The plasmid has resistance to tetracycline. The cloning vector cointegrates with the super binary plasmid. Since the cloning vector has an *E. coli* specific replication origin, but not an *Agrobacterium* replication origin, it cannot survive in *Agrobacterium* without co-integrating with the super binary plasmid. Since the LBA4404 strain is not highly virulent, and has limited application without the super binary plasmid, the inventors have found in yet another embodiment that the EHA101 strain is preferred. It is a disarmed helper strain derived from the hypervirulent A281 strain. The cointegrated super binary/cloning vector from the LBA4404 parent is isolated and electroporated into EHA101, selecting for spectinomycin resistance. The plasmid is isolated to assure that the EHA101 contains the plasmid. EHA101 contains a disarmed pTi that carries resistance to kanamycin. See, Hood et al. (1986) The hypervirulence of *Agrobacterium tumefaciens* A281 is encoded in a region of pTiBo542 outside of T-DNA" *J Bacteriol* 168: 1291-1301 [172].

Further, the Ishida protocol as described provides for growing fresh culture of the *Agrobacterium* on plates, scraping the bacteria from the plates, and resuspending in the co-culture medium as stated in the U.S. Pat. No. 5,591,616 [160] for incubation with the maize embryos. This medium includes 4.3 g MS salts, 0.5 mg nicotinic acid, 0.5 mg pyridoxine hydrochloride, 1.0 ml thiamine hydrochloride, casamino acids, 1.5 mg 2,4-D, 68.5 g sucrose and 36 g glucose per liter, all at a pH of 5.8. In a further preferred method, the bacteria are grown overnight in a 1 ml culture and then a fresh 10 ml culture is re-inoculated the next day when transformation is to occur. The bacteria grow into log phase, and are harvested at a density of no more than $OD_{600=0.5}$, preferably between 0.2 and 0.5. The bacteria are then centrifuged to remove the media and resuspended in the co-culture medium. Since Hi II is used, medium preferred for Hi II is used. This medium is described in considerable detail by Armstrong and Green (1985). The resuspension medium is the same as that described above. All further Hi II media are as described in Armstrong and Green (1985) Establishment and maintenance of friable, embryogenic maize callus and involvement of L-proline. *Planta* 154:207-214 [173]. The result is redifferentiation of the plant cells and regeneration into a plant. Redifferentiation is sometimes referred to as dedifferentiation, but the former term more accurately describes the process where the cell begins with a form and identity, is placed on a medium in which it loses that identity, and becomes "reprogrammed" to have a new identity. Thus the scutellum cells become embryogenic callus.

The term introduced in the context of inserting a nucleic acid into a cell, includes transfection or transformation or transduction and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA). When referring to introduction of a nucleotide sequence into a plant is meant to include transformation into the cell, as well as crossing a plant having the sequence with another plant, so that the second plant contains the heterologous sequence, as in conventional plant breeding techniques. Such breeding techniques are well known to one skilled in the art. For a discussion of plant breeding techniques, see Poehlman (1995) *Breeding Field Crops*. AVI Publication Co., Westport Conn, $4^{th}$ Edit [174]. Backcrossing methods may be used to introduce a gene into the plants. This technique has been used for decades to introduce traits into a plant. An example of a description of this and other plant breeding methodologies that are well known can be found in references such as Poehlman, supra [174], and *Plant Breeding Methodology*, edit. Neal Jensen, John Wiley & Sons, Inc. (1988) [175]. In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a plant is obtained wherein essentially all of the desired morphological and physiological characteristics of the recurrent parent are recovered in the converted plant, in addition to the single transferred gene from the nonrecurrent parent.

EXAMPLES

The following examples are provided in order to demonstrate and further illustrate certain preferred embodiments and aspects of the present invention and are not to be construed as limiting the scope thereof.

Ethanol is an example of a renewable biofuel product which could replace petroleum-based transportation fuel. One of the biggest barriers to producing ethanol from lignocellulosic material is cellulose degradation by cellulases. Expansin synergistic activity with cellulases is believed to lower that barrier. Expansins are plant cell wall loosening proteins that enable cell enlargement and a variety of other developmental processes where cell wall modification is important. Expansin has been shown to enhance the activity of cellulases on cellulose by increasing the accessibility of cellulases to crystalline cellulose. Maize lines expressing the cucumber expansin gene (Genbank Accession No.: U30382, [SEQ ID NO: 4]) were generated as part of a biomass conversion effort to produce large amounts of expansin. In this study, high level expression of cucumber expansin in the transgenic maize lines is demonstrated and it is shown that the maize-derived expansin is active.

Ethanol can partially substitute for petroleum fuel and it can be produced by anaerobic fermentation of sugars from starch or cellulose. Even though yearly production of ethanol has increased, the production from corn starch is not enough to meet the requirement to replace gasoline. Ethanol production which uses hydrolyzed lignocellulosic material can utilize large volumes of agricultural resources that are unused today (Hood et al. 2007 [176]). However, cellulose hydrolysis requires large amounts of cellulase enzymes, and because the cost of the enzymes is still high, the cost of ethanol production is also high. The demand for large amounts of cellulase and their high production cost motivate the development of effective enhancements of cellulase activity.

The plant protein, expansin, may be one of those enhancements. It is believed that expansin induces cell growth by loosening cell wall polymers (Cosgrove et al. 2002 [177]). Because expansin acts through loosening the wall for growth, it suggests that expansin may open the wall structure, possibly allowing entry of other molecules. Indeed, expansin can increase cellulase activity through a synergistic effect when tested with small amounts of expansin in bench scale experiments (Cosgrove 2001 [35]) possibly through increasing accessibility.

Expansin expression is very low in the native plant cell wall. In cucumber seedlings, expansin exists at one part protein per 5,000 parts cell wall (on a dry mass basis) and induces wall extension with these very small amounts (Mc-Queen-Mason & Cosgrove 1995 [178]). Therefore, a recombinant expansin production system is required if this protein is to be used in industrial applications because recovery of large amounts of expansin from natural sources is not possible.

Enzyme production through a plant-based system has many advantages such as low cost and easy scale up (Hood et al. 2007 [176]). High levels of enzyme accumulation in grain offer extremely low cost through easy harvesting, storage and transportation. The plant system is approaching microbial systems in cost structure (Howard et al. 2011 [179]), perhaps allowing applications in cost sensitive industries such as biomass conversion. The plant production system is being utilized to potentially achieve low cost production of expansin.

Example 1

Nucleotide sequence fragments from expressing expansin isolated from bamboo (Bambuseae) *Phyllostachys edulis* were identified at GenBank FP094161.1 [SEQ ID NO: 9] and used to identify a sequence obtained after harvesting young shoots, isolating RNA and preparing cDNA clones. Using PCR primers, a sequence was identified and isolated and is shown as SEQ ID NO: 1 in FIG. 15, which was combined with a 3' histidine tag, shown in bold and underlined [SEQ ID NO: 2] also shown in FIG. 15. Note that the last 9 nucleotides at the end are the stop codon (TAA) plus a Sac I restriction endonuclease cloning site. The sequence was introduced into a vector having the histidine tag to aide in identification. Tobacco was transformed using *Agrobacterium tumefaciens* infiltration for transient expression with six constructs and anti-his antibodies used to attempt to identify expansin protein. Constructs included the 35S promoter (Odell et al. (1985) *Nature* 313:810-812 [82]) and phosphinothricin acetyltransferase (pat) selectable marker (see, e.g., Gordon-Kamm et al., (1990) *Plant Cell* 2:603 [167]). Two constructs contained the cucumber expansin gene, [SEQ ID NO: 4] (shown in FIG. 17), one with a 3' histidine tag, one with 5' histidine tag, and four constructs contained the bamboo expansin gene, two with bamboo cDNA [SEQ ID NO: 1] (one 3', one 5' his tag) and two with genomic DNA [SEQ ID NO: 3] (one 3', one 5' his tag) (shown in FIG. 16). Leaves were harvested from infiltrated plants (3 plants per vector) at 24, 48, and 72 hours after infiltration. No protein was detected in extracts from any of the infiltrated plants.

Example 2

Transgenic maize lines expressing the cucumber expansin gene (Genbank Accession No.: U30382, shown as SEQ ID NO: 4) in FIG. 17 were generated previously as part of a biomass conversion effort. Because it was unknown which subcellular location would be the most beneficial for accumulation of this protein, the top three sites identified from other studies (Hood et al. 2003 [180]; Hood et al. 2007 [176]) were tested—the endoplasmic reticulum (ER), the cell wall and the vacuole. All constructs employed the maize globulin-1 promoter as it shows specificity for embryos and promotes high level expression (Hood et al. 2003 [180]). While procedures for screening of transgenic lines and a breeding program for other genes and proteins in transgenic corn to increase protein accumulation have been previously established (Woodard et al. 2003 [181]), expansin improvement has not been done.

Typically, expansin activity is confirmed by a reconstituted extension assay on inert cell walls (Cosgrove 1989 [36]) or tested by plant cell wall swelling (Cosgrove et al. 2002 [177]). These methods have sensitivity issues and are not appropriate for screening crude expansin protein in hundreds of transgenic seeds because they are slow, laborious and require purified or highly enriched expansin protein to detect activity.

For these reasons, a high throughput novel expansin activity assay (see below) was developed. To test hundreds of corn seed samples, an expansin assay and a corn seed extraction method were optimized. Transgenic corn lines were screened with these methods and the best plants were chosen for further development. Moreover, activity of the plant-derived expansin protein is synergistic with cellulase on pretreated lignocellulosic biomass. The results demonstrate that the corn seed-based system is expected to be a feasible commercial production method to use expansin in the biomass conversion industry.

2. Materials and Methods
2.1. Plant Expression Vectors

Transgenic maize lines were developed as a part of a biomass conversion project. To produce expansin protein in maize, three expression vectors were constructed with the cucumber expansin gene (Genbank Accession No.: U30382, [SEQ ID NO: 4]). All vectors contain the maize tissue-preferred promoter, globulin-1 (Belanger et al. 1991 [75]) and targeting sequences (Table 2). To target the expansin gene to the cell wall, the barley alpha amylase signal sequence (BAASS) (Rogers 1985 [120]) was used. A KDEL (lys-asp-glu-leu) [SEQ ID NO: 14] sequence and vacuole sequence (Holwerda et al. 1992 [130]) were used to target the protein to the endoplasmic reticulum (ER) and vacuole, respectively. All expression cassettes also harbor the proteinase inhibitor II terminator sequence (pin II terminator) (An et al. 1989 [143]).

To produce expansin in the cell wall and ER [SEQ ID NO: 6], BAASS [SEQ ID NO: 5], and KDEL [SEQ ID NO: 14] sequences were spliced onto the gene by polymerase chain reaction (PCR). The amplicon was introduced into a cloning vector, and then moved to an intermediate vector to add the pin II terminator sequence. The complete unit in the intermediate vector was ligated to the plant expression vector, pSB I, as described previously (Hood et al. 2007 [176]). The cucumber expansin gene was provided by D. Cosgrove (The Pennsylvania State University).

All vectors include the glufosinate ammonium (bialaphos) resistance gene, maize-optimized phosphinothricin acetyltransferase (mopat) (White et al. 1990 [182]; Anzai et al. 1989 [183]; Uchimiya et al. 1993 [184]) expressed from the cauliflower mosaic virus (CaMV) 35S promoter. The pSB II vector from Japan Tobacco, Inc (Hiei et al. 1994 [185]) was used as a final cloning vector and the complete expression cassette was placed between the T-DNA borders in this vector. *A. tumefaciens* strain LBA4404 harboring the superbinary vector pSB I (Hiei et al. 1994 [185]) was mated with an *E. coli* strain containing the pSB II vector, and the resulting co-integrated vector, pSBIII was generated, then isolated for characterization.

TABLE 2

| LB | | | | RB | | |
|---|---|---|---|---|---|---|
| P35S | moPAT | pGlob-1 | BAASS | | Expansin | BCA |
| t35S | | pin II | | | | |
| P35S | moPAT | pGlob-1 | BAASS | | Expansin | BCG |
| t35S | | KDEL | pin II | | | |
| P35S | moPAT | pGlob-1 | vacuole seq | | Expansin | BCJ |
| t35S | | pin II | | | | |

Barley Alpha Amylase Sequence:
[SEQ ID NO: 5]
atggcgaacaagcacctgagccttagcctcttcctcgtgctcctgggc ctctccgcctccctcgcctccggc Vacuole Targeting Sequence:
[SEQ ID NO: 6]
atggcccacgcccgcgtcctcctcctggcgctcgccgtcctggcca cggccgcgtcgccgtcgcctcctcctccttcgccgactccaac ccgatccggccggtcaccgaccgcgccgcgtccacc Plant transcription units used to generate transgenic plants expressing the cucumber expansin gene as shown above. Vectors for expression of expansin in maize are shown in Table 2, targeting the protein to the cell wall, endoplasmic reticulum or vacuole. DNA sequence of the signal peptides (cell wall and vacuole) is also shown above. Finally, EHA101 (Hood et al. 1986 [172]) was electroporated with pSB III and used for plant transformation.

2.2. Generation of Transgenic Plants

Stable transformation of maize embryos was conducted with a modified method of Ishida et al. (Ishida et al. 1996 [159]). *A. tumefaciens* strain EHA101 (Hood et al. 1986 [172]) containing each of the vectors described above was grown to optical density 0.5 at 600 nm in yeast extract/peptone medium, and then co-cultivated with immature zygotic embryos of the Hi-II maize genotype at 18° C. for 5 days (Hood et al. 2007 [176]). $T_0$ plants were regenerated from bialaphos-resistant somatic embryos. $T_1$ seeds were produced by pollination with elite inbred lines.

2.3. Gene Confirmation Using PCR

PCR was conducted to confirm the existence of the cucumber expansin gene in transgenic corn. The primers specific for the cucumber expansin gene were 5'-ACC TTC TAC GGC GGT GGT GA-3' [SEQ ID NO: 7] and 5'-CAT CCA GTT CGA GAC CCC TT-3' [SEQ ID NO: 8]. DNA of transgenic corn was used as templates. DNA was extracted from the young leaves of cell wall, ER and vacuole lines using DNeasy® Plant Mini Kit (Qiagen, Germantown, Md.). PCR was done as follows: 98° C. for 10 sec; then 30 cycles of 98° C. for 10 sec, 55° C. for 5 sec, and 72° C. for 50 sec; with a final 7 min extension at 72° C. A programmable PCR thermocycler, Mastercycler epgradient S (Eppendorf North America, Hauppauge, N.Y.) and TaKaRa PrimeSTAR® HS (Premix) (Takara Shuzo, Shiga, Japan) were used with the manufacturer's instructions.

2.4. SDS-Polyacrylamide Gel Electrophoresis and Immunoblotting

Enriched cucumber expansin and recombinant corn expansin were analyzed by Western blot using anti-expansin antibodies. Cucumber expansin was enriched following a protocol described by McQueen-Mason et al. 1992 [2]. Recombinant corn expansin was extracted from mixed seeds of cell wall and ER targeted lines that had been greenhouse grown and self pollinated. Expansin was extracted with 50 mM sodium acetate pH 5.0 and enriched with 30% ammonium sulfate precipitation. Each sample was desalted with a Corning® Spin-X® UF Centrifugal Concentrator 10,000 molecular weight cut-off (MWCO) polyethanesulfone (PES) Membrane (Corning, Inc. Corning, N.Y.) just before use.

SDS-PAGE was conducted with the Novex® NuPAGE® SDS-PAGE Gel System (Invitrogen, Carlsbad, Calif.) using 12% Bis-Tris minigels. Minigels were stained with Coomassie Brilliant Blue R-250 Staining Solution (Bio-Rad, Richmond, Calif.) to confirm efficient separation. Proteins in unstained gels were electrophoretically transferred using an XCell II™ Blot Module (Invitrogen, Carlsbad, Calif.) to an Immobilion-NY+ nitrocellulose membrane (Millipore, Bedford, Mass.). Transfer was performed in a solution of 48 mM Tris, 39 mM glycine, and 20% (v/v) methanol at 4° C. overnight. After transfer, the membrane was blocked with 10% (v/v) horse serum (TCS Bioscience, Basingstoke, Hampshire, UK) in phosphate-buffered saline (PBS) containing 0.05% (v/v) Tween 20 and 2 mM sodium azide for 2 h. Anti-expansin antibody (1:1000) was added to blocking buffer and the blot was incubated in this solution for 1 hour. The membrane was washed with PBS for 2×5 min and Tris-buffered saline (TBS) for 2×5 min. The blot was incubated with alkaline phosphatase conjugated goat anti-rabbit IgG (Sigma, St. Louis, Mo., 1:10,000) in 10% horse serum in TBS for 1 h. The membrane was washed 4×5 min. in TBS. Chemiluminescent detection was conducted with CDP-Star (Roche Diagnostics, Indianapolis, Ind.), Nitro Block II (Tropix, Bedford, Mass.) and CDP-Star detection buffer (0.1M Tris, 0.1M NaCl, pH 9.5). The membrane was washed with CDP-Star detection buffer for 2×2 min then placed in a sealable plastic bag. Detection reagent (3 ml CDP-Star detection buffer, 150 μL Nitro Block II, 30 μL CDP-Star) was poured on the membrane and the bag sealed. After incubation for 5 min., chemiluminescent signal was detected with Kodak Biomax XAR film (Sigma, Rochester, N.Y.) and the film was developed with an SRX-101A Medical Film Processor (Konica, Shinjuku-ku, Tokyo, Japan). The protein marker for SDS-PAGE was Precision Plus Protein™ Dual Color Standards (Bio-Rad, Richmond, Calif.). The expansin immunoblot protocol and antibody were kindly provided by D. Cosgrove (The Pennsylvania State University).

2.5. Expansin Assay Optimization Using Design of Experiment (DOE)

The major factors of the expansin assay and corn sample preparation were optimized to find the best conditions to determine expansin activity in corn seed. Using DOE, three factors; 1) sample amount, 2) incubation time and 3) NaCl concentration for extraction from seed were tested with three levels per factor (Table 3). A $3^3$ factorial design was used (three factors, three levels for each factor) with three observations for each combination. Assays were conducted using Sigmacell microcrystalline cellulose (Sigma, St. Louis, Mo.) as the substrate in 200 μL reactions in 96-well plates. Once data were obtained, factor effects as well as their interactions were analyzed using three-way Analysis of Variance (ANOVA).

2.6. Corn and Cucumber Sample Preparation for Expansin Assay

For the single seed assay, each corn grain was crushed using a hammer and transferred to a 2 ml tube with six 2.8 mm stainless steel beads and 1 ml of 50 mM sodium acetate buffer pH 5.0 containing 150 mM NaCl. The assembled tube was cooled at −20° C. for 30 min and inserted in the Precellys®24 lyser/homogeniser (Bertin Technologies, Saint Quentin en Yvelines Cedex, France) to extract protein. Precellys®24 settings were: 5000 rpm, 20 sec cycle duration, 5 sec delay time between cycles, for 3 total cycles. After protein extraction, the lysate was transferred to 1.5 ml centrifuge tubes and centrifuged at 16,000 g for 30 min.

TABLE 3

Critical factors and levels used to conduct DOE.

| Factors | | Level | | |
|---|---|---|---|---|
| | | 0 | 1 | 2 |
| Factor A | Sample amount (corn protein) | 5 ug | 10 ug | 20 ug |
| Factor B | Incubation time | 0.5 hr | 1 hr | 2 hr |
| Factor C | NaCl concentration of Extraction buffer | 0 mM | 150 mM | 300 mM |

In some assays, 6 seeds from a single transgenic ear were combined, cooled at 4° C. overnight and ground with a coffee grinder at 4° C. Ground seeds (400 mg) were used to extract protein. The protein extraction method was the same as that used for single seeds.

Enriched recombinant corn expansin and native corn seed extract were used as a positive and negative control sample for the expansin assay, respectively. For preparing enriched corn extract, 300 g of corn seed from several self-pollinated plants was cooled at 4° C. overnight and ground with a coffee grinder. Ground seeds were mixed with 1 Liter of 50 mM sodium acetate buffer pH 5.0, 1 M NaCl and incubated at 4° C. for 1 hr with gentle stirring. After Incubation, crude extract and tissues were separated with Miracloth. Ground seed was re-extracted using the same method twice more and the supernatants were pooled. Expansin was enriched with 60% ammonium sulfate precipitation. Ammonium sulfate pellets were stored at −80° C. and were resuspended with 50 mM sodium acetate buffer pH 5.0 and desalted with a Corning® Spin-X® UF Centrifugal Concentrator 10,000 MWCO PES Membrane (Corning, Inc. Corning, N.Y.) just before use.

Enriched cucumber expansin extract was prepared following a protocol described by McQueen-Mason et al. 1992 [2] with minor modifications. In brief, 300 g of ~3 cm hypocotyl regions of etiolated cucumber seedlings were collected on ice and frozen in liquid nitrogen. Frozen tissues were ground with a mortar and pestle then the wall fragments were resuspended with 20 mM Hepes, pH 6.8, 2 mM EDTA, 3 mM sodium metabisulfite at 4° C. and extracted with gentle stirring for 30 min. Tissues were collected by filtration using Miracloth (Calbiochem, San Diego, Calif.) and washed twice with the same buffer. Expansin crude extract was prepared from the pellet by three extractions with 20 mM Hepes, pH 6.8, 1 M NaCl, 2 mM EDTA, 3 mM sodium metabisulfite at 4° C. for 1 hr each. Supernatants were pooled and expansin protein was precipitated with 60% ammonium sulfate. Ammonium sulfate pellets were stored at −80° C. and were resuspended with 50 mM sodium acetate buffer pH 5.0 and desalted with a Corning® Spin-X® UF Centrifugal Concentrator 10,000 MWCO PES Membrane (Corning, Corning, N.Y.) just before use.

2.7. Expansin Activity Assay

The expansin activity assay was conducted as described herein. In brief, Sigmacell cellulose S3504 (Sigma, St. Louis, Mo.), Sigma® C2730 cellulase (crude fungal cellulose mixture from *Trichoderma reesei*, Sigma, St. Louis, Mo.), and expansin were mixed and the final volume was brought up to 200 μL with 50 mM sodium acetate buffer pH 5.0. For high throughput assay, a 96-well microtiter plate (Corning® 96 well EIA/RIA plates, CLS9017, Corning, N.Y.) was used. Enriched transgenic corn extract and native corn extract were used as positive and negative control samples, respectively. Each plate was incubated at 37° C. with agitation. After incubation, plates were left on the bench for 30 min at room temperature to precipitate the Sigmacell cellulose. Ten microliters of supernatant were transferred to a new 96-well plate and 60 μl glucose oxidase solution were added to each well. This plate was incubated at 37° C. for 30 min without shaking After incubation, 60 μl of 12 N sulfuric acid were added to each well to stop the reaction. The developed pink color was measured at O.D. 540 nm. Expansin activity was expressed as the ratio of the glucose amount released from cellulose by expansin synergistic activity with cellulase compared to glucose released by cellulase alone. Expansin activity was calculated (Equation 1) as:

$$\text{Expansin activity} = \frac{Sc - So}{Co} \quad \text{Equation 1}$$

where Sc is an average signal of the wells which had expansin and cellulase added together; So is an average signal of the wells which had putative expansin only (i.e., corn seed extract); Co is an average signal of the wells which had cellulase only.

2.8. Screening of Transgenic Corn Lines

Transgenic corn lines were screened using the expansin activity assay. For efficient screening, the screening were divided into 3 steps: 1) construct analysis, 2) individual transgenic event (ITE) analysis from a construct and 3) individual plant analysis from an ITE. Corn samples were prepared with the method described above. To find the best construct (generating cell wall, ER or vacuole targeted protein), 30 plants were randomly chosen from ITEs generated from each construct and their expansin activity was compared. Best events were chosen by analysis of all ITEs of the chosen construct. Single seed assays were conducted to find best plants from chosen ITEs.

2.9. Activity of Recombinant Corn Expansin on Lignocellulosic Material

Enriched cucumber expansin and enriched recombinant corn expansin were prepared as described above. Their expansin activity was tested with Sigmacell, pretreated corn stover and pretreated tobacco stems. In this assay, components were incubated for 6 hrs instead of 1 hr.

Pretreated corn stover was provided by NREL and obtained from J. Howard (Applied Biotechnology Institute, San Luis Obispo, Calif.). It was stored at −20° C. and thawed and washed with 50 mM sodium acetate pH 5.0 5 times just before use.

Tobacco stems were pretreated following a protocol described by Sathistsuksanoh et al. [186]. In brief, 1.5 g of dry stems were mixed with 9 ml of 85% phosphoric acid and incubated at 50° C. for 45 min, then chilled on ice. After chilling, 40 ml of 95% ethanol was added then the mixture centrifuged at 6,950 g for 20 min at room temperature. The pellet was resuspended with 40 ml of 95% ethanol then centrifuged twice more as above. The pellet was washed with water and centrifuged again. Pretreated pellets were stored at −20° C. The pellet was thawed and washed with 50 mM sodium acetate pH 5.0 5 times just before use. Pretreated tobacco stems were provided by J. Xu and X. Ge (Arkansas State University).

3. Results 3.1. Construction of Expression Vectors and Transgenic Plant Generation To achieve high protein accumulation in maize seed, several factors were considered. For maize expression, the first 40 codons of each coding sequence including the signal sequence were optimized and the strong embryo-preferred globulin-1 promoter from maize was used (Belanger and Kriz 1991 [75]; Streatfield et al. 2002 [187]; Hood et al. 2003 [180]). In order to move the nascent protein into the endomembrane system, the barley α-amylase signal sequence (Rogers 1985 [120]) was fused to the 5' end of the ER and cell wall constructs. To retain the protein in the ER, a KDEL-encoding sequence was added at the 3' end of the gene. The maize lytic vacuole was targeted using the vacuole targeting sequence from barley aleurain (Holwerda et al. 1992 [130]). A herbicide resistance gene (35 S:pat) was used for selection of transgenic events (White et al. 1990 [182]).

3.2. Regeneration of Transgenic Plants

*A. tumefaciens* co-cultivation with immature zygotic embryos from Hi-II maize was conducted to generate transgenic maize plants. Multiple ITEs were recovered from each vector (Table 4). Multiple clonal plants were recovered from somatic embryos of positive herbicide-resistant callus of each independent event. Plantlets were transferred to soil and allowed to flower in the greenhouse. Female flowers of the transgenic plants were pollinated with pollen from an elite inbred. Ten, 22 and 12 ITEs were recovered for cell wall (BCA), ER (BCG) and vacuole (BCJ) targeted proteins, respectively (Table 4).

TABLE 4

Recovery and expression of independent transgenic events

| Construct | Promoter/target sequence/gene | Target | # events | # plants |
|---|---|---|---|---|
| BCA | Globulin1:BAASS:Expansin | Cell wall | 10 | 65 |
| BCG | Globulin1:BAASS:Expansin: KDEL | ER | 22 | 202 |
| BCJ | Globulin1:Vacuole:Expansin | Vacuole | 12 | 108 |

3.3. PCR Verification of Expansin Gene in Transgenic Plants

Genomic DNA from ITEs was extracted and analyzed by PCR to verify the existence of the expansin gene. Cucumber expansin gene-specific primers were used for amplification of a portion of the expansin gene and their expected amplicon size was 484 bp (FIG. 1). All transgenic lines showed the expected size of the amplicon and LH 283 did not show any amplicon. FIG. 1 shows the presence of the expansin gene in transgenic corn lines was confirmed using PCR. One ITE from each vector was screened. EXPA, synthesized cucumber expansin gene in *E. coli*; BCA, DNA from transgenic line leaf (cell wall); BCG, DNA from transgenic line leaf (ER); BCJ, DNA from transgenic line leaf (vacuole); LH283, DNA from native corn leaf.

3.4. Western Blot Analysis of Expansin from Cucumber and Transgenic Corn.

Figure 2:
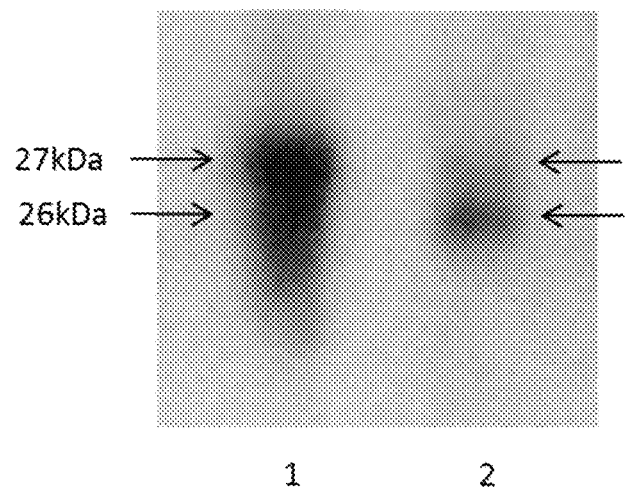
FIG. 2 shows a western blot detection of enriched cucumber expansin and enriched recombinant corn expansin using anti-expansin antibody. Lane: 1, cucumber expansin; 2, recombinant corn expansin from BCG seed. Equal volumes of cucumber and corn extract (10 µL) were used (approximately 20 µg of total protein in the corn extract).

Cucumber and transgenic corn expansin salt extracts were prepared as described in materials and methods. After electrophoresis and blotting, two bands were detected (26 and 27 kDa) in each lane with the anti-expansin antibody, ~1 kDa different in molecular weight (FIG. 2). This is the same result as seen by McQueen-Mason et al. 1992 [2]. An interesting observation is that the dominant band in maize extracts is opposite the dominant band in cucumber extracts. Nevertheless, this result shows that transgenic corn produces expansin protein. FIG. 2 shows a western blot detection of enriched cucumber expansin and enriched recombinant corn expansin using anti-expansin antibody. Lane: 1, cucumber expansin; 2, recombinant corn expansin from BCG seed. Equal volumes of cucumber and corn extract (10 μL) were used (approximately 20 μg of total protein in the corn extract).

3.5. Expansin Assay Optimization Using Design of Experiments

In the published method to recover expansin protein from plant tissue, the buffer contains a high concentration of salt (e.g. 50 mM sodium acetate pH 5.0, 1M NaCl), which is required because the hydrogen bonds between the cellulose binding domain of expansin and cell wall polymers must be broken during extraction (McQueen-Mason et al. 1992 [2]). A high salt concentration in the extraction buffer was challenging for the new high throughput assay because salt inhibits the activity of cellulase and glucose oxidase which are the key components of the expansin activity assay. A desalting method which could be used with the high throughput expansin assay was sought. It was found that the centrifugal desalting device which has a regenerated cellulose membrane absorbed a significant amount of expansin protein from the crude extract (data not shown).

Moreover, high throughput desalting plates such as the Zeba 96-well Spin Desalting plate (Pierce, Rockforf, Ill.) and the MultiScreen® Filter Plate with an Ultracel®-10 membrane (Millipore, Bedford, Mass.) were not appropriate for desalting corn samples because they diluted the sample too much or were easily clogged.

Therefore, using design of experiments (DOE) various NaCl concentrations were investigated for the extraction buffer. The objective was to find the most effective NaCl concentration which would extract expansin protein from corn seed but did not inhibit the expansin activity assay. Three levels of NaCl were assigned in the extraction buffer as 0, 150 and 300 mM were hypothesized that would be enough salt (150 or 300 mM) to extract the protein but would not inhibit the assay. Two additional factors, the amounts of sample extract and incubation time, were also tested. Experiments were performed based on a $3^3$ factorial design and analyzed experimental results with three-way Analysis of Variance (ANOVA).

TABLE 5

Three-way ANOVA table testing three factors on expansin activity
Dependent Variable: di

| Source | DF | Squares | Mean Square | F Value | Pr > F |
|---|---|---|---|---|---|
| Model | 26 | 135.4138889 | 5.2082265 | 5.3 | <.0001 |
| Error | 54 | 53.0683333 | 0.9827469 | | |
| Corrected Total | 80 | 188.4822222 | | | |

| R-Square | Coeff Var | Root MSE | di Mean |
|---|---|---|---|
| 0.718444 | 112.4625 | 0.991336 | 0.881481 |

Error! Reference source not found. shows the ANOVA table for the full model which has three factors (A, B and C) and their interactions. Because the p-value is less than 0.001 (highlighted) it was concluded that this model is significant at the significance level 0.05.

TABLE 6

Factor and interaction effects from three-way ANOVA

| Source | DF | Type I SS | Mean Square | F Value | Pr > F |
|---|---|---|---|---|---|
| fa | 2 | 26.18388889 | 13.09194444 | 13.32 | <.0001 |
| fb | 2 | 1.15796296 | 0.57898148 | 0.59 | 0.5583 |
| fa * fb | 4 | 30.31314815 | 7.57828704 | 7.71 | <.0001 |
| fc | 2 | 3.47018519 | 1.73509259 | 1.77 | 0.1808 |
| fa * fc | 4 | 10.71425926 | 2.67856481 | 2.73 | 0.0386 |
| fb * fc | 4 | 32.09185185 | 8.02296296 | 8.16 | <.0001 |
| fa * fb * fc | 8 | 31.48259259 | 3.93532407 | 4 | 0.0009 | fa, factor A (sample amount); fb, factor B (incubation time); fc, factor C (NaCl concentration)

As shown in Table 6, the three-way interaction among factors A, B, and C is significant at the significance level 0.05 because its p-value is 0.0009. This indicates all main factors and two-way interactions are also significant. Each factor and their interactions were also analyzed (Table 6). To find the best combinations which show the highest mean, Bonferroni multiple comparions were used. Error! Reference source not found. shows the combinations and their mean value.

TABLE 7

Bonferroni multiple comparison
Least Squares Means
Adjustment for Multiple Comparisons: Bonferroni
H0:LSMean = Control

| fa | fb | fc | di LSMEAN | Pr > \|t\| |
|---|---|---|---|---|
| 0 | 0 | 0 | 2.35000000 | |
| 0 | 0 | 1 | 1.80000000 | 1.0000 |
| 0 | 0 | 2 | −0.98333333 | 0.0034 |
| 0 | 1 | 0 | −0.71666667 | 0.0100 |
| 0 | 1 | 1 | 0.15000000 | 0.2291 |
| 0 | 1 | 2 | 2.75000000 | 1.0000 |
| 0 | 2 | 0 | 0.53333333 | 0.7521 |
| 0 | 2 | 1 | 1.81666667 | 1.0000 |
| 0 | 2 | 2 | −0.30000000 | 0.0482 |
| 1 | 0 | 0 | −0.28333333 | 0.0512 |
| 1 | 0 | 1 | −1.21666667 | 0.0013 |
| 1 | 0 | 2 | −1.21666667 | 0.0013 |
| 1 | 1 | 0 | 0.76666667 | 1.0000 |
| 1 | 1 | 1 | 1.88333333 | 1.0000 |
| 1 | 1 | 2 | 0.30000000 | 0.3707 |
| 1 | 2 | 0 | −0.21666667 | 0.0651 |
| 1 | 2 | 1 | 0.56666667 | 0.8285 |
| 1 | 2 | 2 | 1.36666667 | 1.0000 |
| 2 | 0 | 0 | 3.16666667 | 1.0000 |
| 2 | 0 | 1 | 2.01666667 | 1.0000 |
| 2 | 0 | 2 | 2.48333333 | 1.0000 |
| 2 | 1 | 0 | 0.23333333 | 0.3001 |
| 2 | 1 | 1 | 1.13333333 | 1.0000 |
| 2 | 1 | 2 | 2.65000000 | 1.0000 |
| 2 | 2 | 0 | −0.53333333 | 0.0202 |
| 2 | 2 | 1 | 1.03333333 | 1.0000 |
| 2 | 2 | 2 | 2.26666667 | 1.0000 | fa, factor A (sample amount); fb, factor B (incubation time); fc, factor C (NaCl concentration)

The results of this DOE showed that the combination of factor A level 2, factor B level 0 and factor C level 0, which is 20 ug of extract, 0.5 hr incubation time and extraction buffer without salt, were the best combination. However, 1 hr incubation was used to ensure an adequate reaction time to lower variability and 150 mM NaCl for the extraction buffer, to ensure consistent extraction, with 20 ug of sample protein. NaCl concentrations up to 300 mM do not affect the expansin activity assay and this combination of conditions was sensitive enough to distinguish the high and low recombinant corn expansin activity without desalting the extracts.

3.6. Screening of Transgenic Corn Lines

Figure 3:
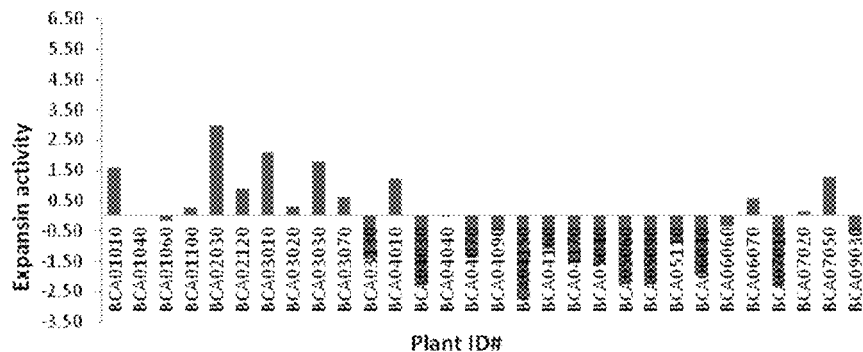
FIG. 3A-C show screening results of transgenic corn lines to determine the construct that produced the highest expressing plants.
Figure 3:
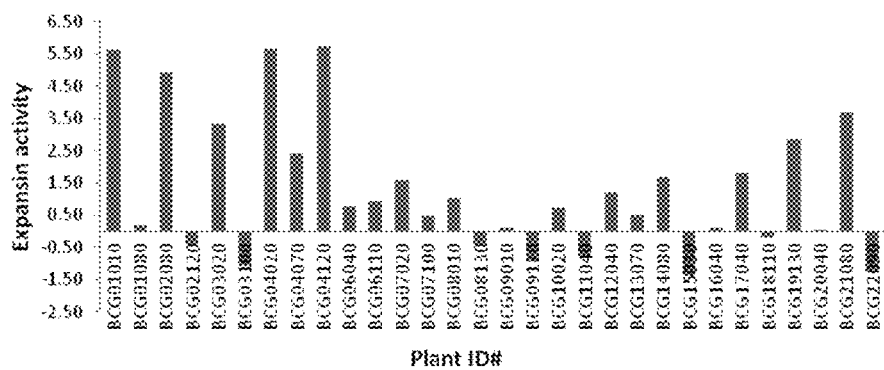
Figure 3:
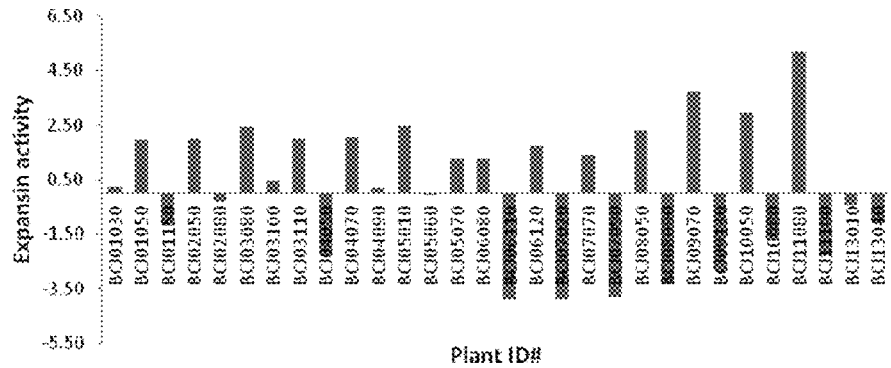

In order to use the transgenic plants for industrial applications, they must be screened and those showing the highest expression chosen for further development. Experience has demonstrated that single seed assays are the most useful because the seed populations from a single ear are segregating 1:1 (so half are nulls) and individual seeds can show variable potential for high expression (Hood et al. 2003 [180]; Hood et al. 2007 [176]). Pools of seed are averages of positive and negative seeds and often mask the expression of really high seeds. In addition, a pool of 50 seeds is required in order to obtain a significant average pool of seeds, something that is not usually possible when recovering first generation seed from greenhouse grown plants. However, in the case of these expansin plants, there was a concern that the activity assay was not sensitive enough to analyze single seeds, and a small pool of seed for a number of the ITEs was screened to determine the range of the values for the recombinant expansin seeds. Nevertheless, choosing the best plants is important because these are the ones that could be propagated for industrial applications. Moreover, because recombinant protein accumulation can be increased by manipulating corn germplasm through breeding and the best plants can be greatly improved with elite inbred maize germplasm (Hood et al. 2012 [188]), it is critical to identify the very best T1 seeds and plants for propagation. Thus, expansin activity in transgenic corn was screened to choose 1) the construct that yielded the highest overall expression in seeds, 2) the highest-expressing ITEs of the best construct and 3) the highest-expressing plants of the best ITEs. To choose the best construct, 30 plants representing all events from each construct were randomly selected from BCA (cell wall), BCG (ER) and BCJ (vacuole) lines and the seeds of the chosen plants were analyzed using the optimized expansin activity assay and sample preparation method (FIG. 3A, FIG. 3B and FIG. 3C). FIG. 3A-C show screening results of transgenic corn lines to determine the construct that produced the highest expressing plants. FIG. 3A shows cell wall-localized T1 expansin seeds analyzed from 30 lines selected at random from 10 independent transgenic events. FIG. 3B shows endoplasmic reticulum (ER)-localized T1 expansin seeds analyzed from 30 lines selected at random from 22 ITEs. FIG. 3C shows vacuole-localized T1 expansin seeds analyzed from 30 lines selected at random from 12 ITEs. Expansin activity was calculated as described herein.

To analyze the results of construct screening, one-way ANOVA was used to determine if all three constructs have the same mean value. For the ANOVA analysis, construct was used as a factor which has three different levels (BCA, BCG and BCJ). As highlighted in Table 8, it was concluded that there is at least one level which is different from others. Therefore, multiple comparisons were conducted among those three levels (Table 9) and it was found that one vector has the highest mean value which is significantly different from the others.

The corn expansin extraction method that does not include a desalting step has a drawback. The desalting step not only removes salt but also glucose from corn extracts. Therefore, glucose present in the extract (not released by expansin synergistic activity with cellulase) could mask the expansin assay and contribute to background. However, the corn expansin extraction method was fast, convenient and sensitive enough to distinguish the better transgenic lines in spite of background glucose.

Because the ER targeted construct was chosen as the best construct, individuals from the ER targeted protein ITEs (BCG) were further screened to identify high-expressing plants within positive events. Not only was expansin activity the highest overall for this construct, expansin activity in individual plants of the ER lines was also higher than either cell wall or vacuole targeted protein lines.

Figure 4:
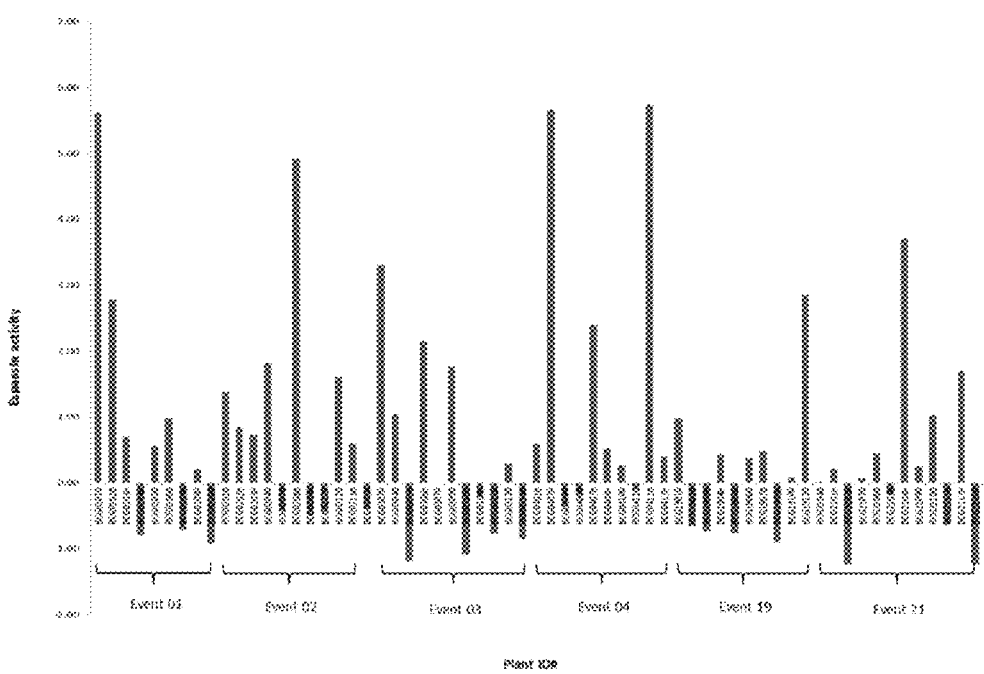
FIG. 4 shows expansin activity assays of all plants from selected high-expressing BCG ITEs. All plants of chosen ITEs (01, 02, 03, 04, 19 and 21) were analyzed with the expansin activity assay. Samples for the assay were prepared from 6 randomly chosen seeds from each plant. Each bar is the ratio of glucose released from expansin plus crude fungal cellulase compared to fungal cellulase alone. Assays were run in triplicate and the ratio is determined from the average of the triplicates.

Six positive events (01, 02, 03, 04, 19 and 21) from the ER construct were chosen for further analysis. All plants from these ITEs were analyzed with the same method used for selecting the best construct (FIGS. 4A&B). As seen in FIGS. 4A&B, several plants from each ITE showed good activity. However, they are not all high, and they are not all the same. These assays were done with pools of six seed, and those that were highest were then analyzed by single seed assays. One plant of event 01 and two plants of event 04 (BCG01010, BCG04020 and BCG04120) showed relatively higher activity than others and were analyzed in more detail. FIG. 4 shows expansin activity assays of all plants from selected high-expressing BCG ITEs. All plants of chosen ITEs (01, 02, 03, 04, 19 and 21) were analyzed with the expansin activity assay. Samples for the assay were prepared from 6 randomly chosen seeds from each plant. Each bar is the ratio of glucose released from expansin plus crude fungal cellulase compared to fungal cellulase alone. Assays were run in triplicate and the ratio is determined from the average of the triplicates.

Figure 5:
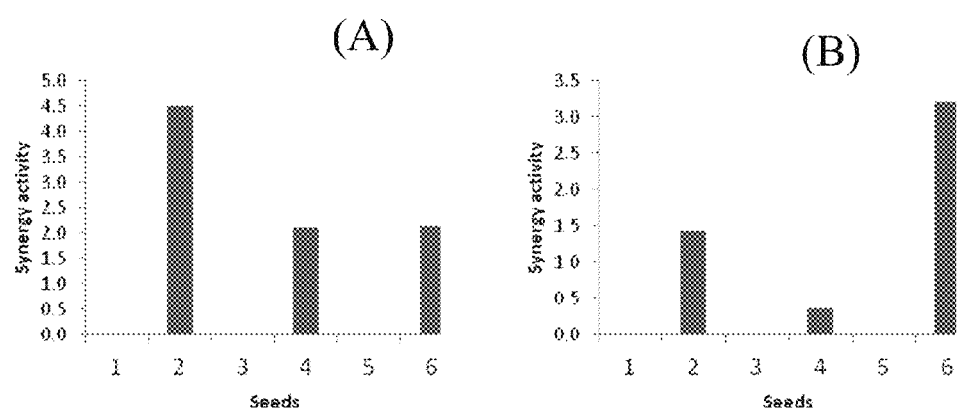
FIGS. 5A&B shows an analysis of single seed variation of two high-expressing BCG plants. Six seeds were randomly chosen and their expansin activity was analyzed. Each bar represents the synergistic activity of each seed extract.
(FIG. 5B) Single seed assay results BCG04120. In each case, seeds 1, 3, and 5 were null segregants. Where other seed from these two lines is planted and bred for production, they are expected to produce even higher amounts of expansin.

The single seed expansin activity assay was then conducted on BCG01010 and BCG04120 (FIGS. 5A&B). For the single seed assay, 6 seeds were randomly chosen and analyzed separately for expansin activity. As expected, three seeds were null, showing no synergy. However, the three positive seeds from each plant clearly showed tremendous variation. Their synergy ranged from a low of 0.5× increased activity for seed 4 of BCG04120, up to 4.5× increased activity for seed 2 of BCG01010. This variation is also expected from past experience and shows the highest activity in seed 2 of BCG01010 and seed 6 of BCG04120. FIGS. 5A&B shows an analysis of single seed variation of two high-expressing BCG plants. Six seeds were randomly chosen and their expansin activity was analyzed. Each bar represents the synergistic activity of each seed extract. FIG. 5A shows single seed assay results of BCG01010. FIG. 5B shows single seed assay results BCG04120. In each case, seeds 1, 3, and 5 were null segregants. Where other seed from these two lines is planted and bred for production, they are expected to produce even higher amounts of expansin.

TABLE 8

One-way ANOVA analysis of construct screening
One-way ANOVA

| Source | DF | SS | MS | F | P |
|---|---|---|---|---|---|
| Factor | 2 | 40.48 | 20.24 | 4.82 | 0.01 |
| Error | 87 | 365.36 | 4.2 | | |
| Total | 89 | 405.84 | | | |

S = 2.049
R-Sq = 9.97%
R-Sq + 7.90%

TABLE 9

95% confidence intervals for each level of construct.
C8 represents BCJ, C9 represents BCG, and C10 represents BCA.

```
                        Individual 95% CIs For Mean Based on
                                     Pooled StDev
Level   N    Mean    StDev  ---+---------+---------+---------+------
C8     30   0.222    2.430            (---------*--------)
C9     30   1.297    2.110                        (--------*---------)
C10    30  -0.316    1.497   (--------*--------)
                            ---+---------+---------+---------+------
                           -0.80       0.00      0.80      1.60
```

Pooled StDev = 2.049

3.7. Expansin Activity on Lignocellulosic Material

Figure 6:
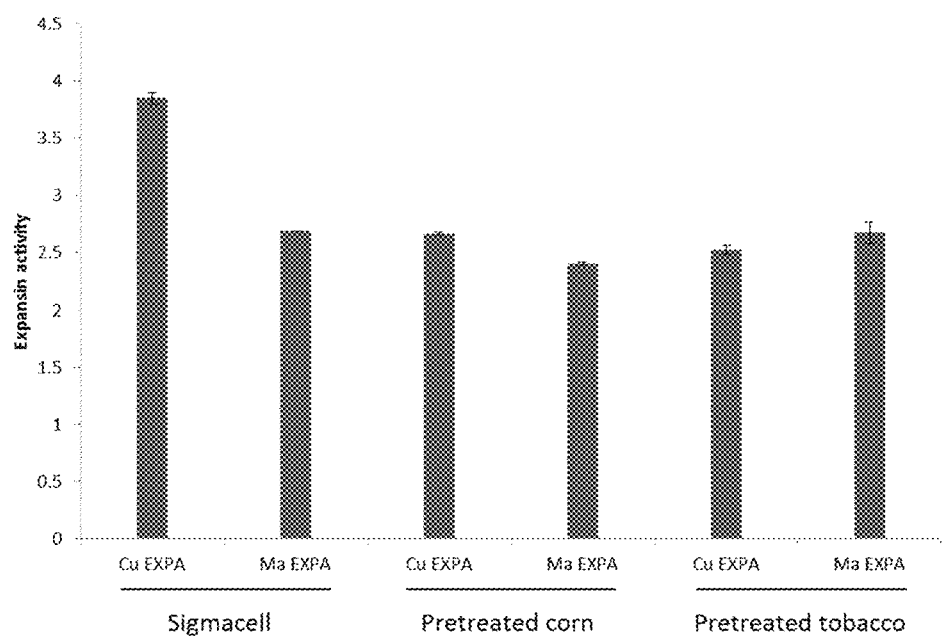
FIG. 6 shows Expansin activity on lignocellulosic material. Cucumber and recombinant corn expansin were tested with various substrates: Sigmacell, pretreated corn stover and pretreated tobacco stems. Cu EXPA, enriched cucumber expansin; Ma EXPA, enriched recombinant corn expansin. Activity is expressed as described herein.

Synergistic activity of recombinant corn expansin and cucumber expansin on lignocellulosic material was compared (FIG. 6). This result showed that recombinant corn expansin has activity similar to cucumber expansin on three distinct substrates—Sigmacell, pretreated corn stover and pretreated tobacco stems, indicating that expansin from the corn system could be an industrial product. FIG. 6 shows Expansin activity on lignocellulosic material. Cucumber and recombinant corn expansin were tested with various substrates: Sigmacell, pretreated corn stover and pretreated tobacco stems. Cu EXPA, enriched cucumber expansin; Ma EXPA, enriched recombinant corn expansin. Activity is expressed as described herein.

4. Discussion

The success of recombinant protein expression in plants depends in part on the characteristics of the target protein (Streatfield 2007 [189]). Each protein also accumulates to variable degrees in different subcellular compartments. Three target organelles were chosen: 1) cell wall, 2) ER and 3) vacuole, because they appear to be the top three sites for protein accumulation in corn seed (Hood et al. 2007 [176]; Streatfield et al. 2002 [187]). However, higher levels of expansin protein were expected to adversely impact the plant.

Levels of expansin in these corn seeds could not be assessed after these transgenic lines were generated because of the lack of an efficient expansin assay system. An ELISA is a logical, high throughput assay to screen transgenic corn seeds, but no commercial source of expansin protein and anti-expansin antibody is available. Overexpression of expansin using the *E-coli* expression system with Gateway® technology, and the tobacco transient transformation system with *Agrobacterium* (Medrano et al. 2009 [190]) were not successful. Anti-peptide antibodies were equally unsuccessful at detecting expansin. The traditional activity assay for expansin is cumbersome and slow, thus it is not practical for screening large numbers of samples. Therefore, a novel high throughput expansin activity assay was developed. With this assay, the transgenic maize seeds could be screened and high-expressing potentially commercial lines found. In addition, the desired activity of recombinant corn expansin for commercial application was shown because recombinant expansin not only showed activity on Sigmacell but also on pretreated corn stover and pretreated tobacco stems.

Expansin expression using the transgenic maize bioproduction system was successful. ER targeted protein showed the best accumulation over other subcellular locations, similar to E1 cellulase (Hood et al., 2007 [176]). Moreover, the best plants of ER-targeted lines can now be used for breeding to increase expansin expression, allowing scale-up of production for testing in larger volumes.

Example 3

Improvements in recombinant protein expression are expected, and thus the economics of this system are also expected to be very favorable.

Presently, submerged culture fermentation is the major method to produce industrial cellulases. Scale-up of this system to meet the volume requirement of cellulases for biomass conversion is capital intensive. In addition, current production costs of cellulases from this system are in the $0.50 per gallon of biofuel range (or $10 per kg enzyme), making the cost of cellulases too high for commercialization of the industry. Therefore, submerged culture fermentation using microorganisms is still impractical to meet the requirement of the biomass conversion industry (Hood et al. 2007 [176]; Howard et al. 2011 [179]), suggesting that alternative approaches should be used to lower the cost of enzymes.

One approach to lowering the cost of cellulases for biomass conversion is to produce the enzymes required in the greatest amounts in a lower cost production system. Cellulase production using the transgenic maize system was tested and its initial expression was ~15% TSP of maize seed extract representing 0.04% of dry weight (Hood et al. 2007 [176]). Moreover, it has been observed that breeding transgenic maize lines with initial high expression to elite inbred maize lines can significantly increase accumulation of heterologous recombinant protein to as much as 100-fold over the initial amount in T1 seed (Streatfield et al. 2001 [191]; Hood et al. 2003 [180]). Based on this information and recent enzyme specific activity, cellulase production through the maize-seed production system could meet industrial requirements for biomass conversion (Howard et al., 2011 [179]). These efforts could be further enhanced by addition of synergistic amounts of recombinant expansin from seed. Even though the exact level of expansin accumulation is not known, addition of approximately equivalent amounts of total protein extract from seed and crude fungal cellulases can improve glucose release as much as 2.5-fold.

It can assumed that the recombinant expansin accumulation level in corn seed empirically is 0.015% of dry weight (calculated from a 0.5% TSP assumption) and estimate the cost effectiveness of this cellulase activity enhancement. For example, as seen in Table 10 below, if corn extracts containing expansin are added at a 1:1 ratio with crude fungal cellulases, at its current level of expression this extract lowers the cost of fungal cellulases necessary for biomass conversion by $2 per kilogram. The expression level of the recombinant protein in maize seed has a tremendous impact on the cost of production, and breeding can improve that. In addition, because the recombinant expansin is entirely contained within the germ (embryo) of the seed, the production grain can be processed to recover clean germ which is 10% of the dry weight of the grain, improving the enzyme concentration in dry mass 10-fold. Thus, if breeding can improve expression just 5-fold as shown in the last line of Table 10, added expansin could lower the cost of crude fungal cellulases to $4.60 per kg—more than half. These examples clearly show that with standard breeding and processing activities, the impact of recombinant expansin on the biomass conversion industry could be significant. What remains to be done is testing the system at a large scale.

TABLE 10

Comparison of cost of enzymes for biomass conversion when crude fungal cellulase is enhanced with recombinant expansin.

| System | Source | Expansin manufacturing cost estimates ($/kg) | Cellulase activity fold increase by synergistic activity | Final cost |
|---|---|---|---|---|
| Microbial | Microbial fermentation 50 g/l Fungus | | | $10[1] |
| Extraction from seed w/by-product | Extraction from corn germ @ 1.5% of dry wt | $10 | 2.5 | $8 |
| Extraction from seed w/by-product | Extraction from corn germ @7.5% of dry wt | $2.50 | 2.5 | $5 |
| Seed by-product | Direct use of corn germ @1.5% of dry wt | $7.8 | 2.5 | $7.12 |
| Seed by-Product | Direct use of corn germ @ 7.5% dry wt | $1.50 | 2.5 | $4.6 |

[1]Cost of crude fungal cellulase in every case is $10 per kg. Cost of expansin varies according to increases in accumulation levels and changes in processing steps. Breeding of expansin lines will allow recovery of increased expression of expansin in grain.

Example 4

While procedures for screening of transgenic lines and a breeding program for other genes and proteins in transgenic corn to increase protein accumulation have been previously established (Woodard et al. 2003 [181]), expansin improvement has not been done.

Typically, expansin activity is confirmed by a reconstituted extension assay on inert cell walls (Cosgrove 1989 [36]) or tested by plant cell wall swelling (Cosgrove et al. 2002 [177]). Neither of these methods is appropriate for screening crude expansin protein in hundreds of transgenic seeds because these methods are slow, laborious and require purified or highly enriched expansin protein. To screen transgenic maize lines, an ELISA was developed because it is a high-throughput assay and can identify the best transgenic plants. But no anti-cucumber expansin antibody or expansin protein is commercially available. Therefore, to generate antibodies, overexpression of cucumber expansin was required. Several attempts were made to overexpress expansin protein because 1) expansin purification is not efficient since expansin exists in very low quantities in the cell wall, 2) anti-expansin antibodies and expansin proteins are not commercially available and 3) ELISA is a high throughput detection method requiring antibodies generated from large quantities of protein. Nevertheless, overexpression of expansin using the *E. coli* expression system with Gateway® technology (Invitrogen, Carlsbad, Calif.) and tobacco transient transformation with *Agrobacterium* (Medrano et al. 2009 [190]) were not successful. Anti-peptide antibodies were developed, and although they were high titer against the peptides, they did not recognize native expansin.

For these reasons, a high throughput novel expansin activity assay was developed which determines the increased activity of cellulase by expansin addition. Expansin protein from transgenic corn seeds was fractionated and enriched for use as a positive (active) protein because a large amount of expansin was required to test and optimize the novel expansin assay. Assay validation was conducted with enriched native cucumber expansin. Anti-expansin antibody (provided by D. Cosgrove, The Pennsylvania State University) was used to confirm that expansin protein was present in the extract and could account for the measured activity.

2. Materials and Methods 2.1 Enriched Cucumber Expansin Preparation

Enriched cucumber expansin extract was prepared following a protocol described by McQueen-Mason et al. 1992 [2] with minor modifications. In brief, 300 g of ~3 cm hypocotyl regions of etiolated cucumber seedlings were collected on iced water and frozen in liquid nitrogen immediately. Frozen tissues were ground with a mortar and pestle, then the wall fragments were homogenized with 20 mM Hepes, pH 6.8, 2 mM EDTA, 3 mM sodium metabisulfite at 4° C. and extracted with gentle stirring for 30 min. Tissues were collected by filtration using Miracloth (Calbiochem, San Diego, Calif.) and washed twice with the same buffer. Expansin crude extract was prepared from the pellet by three extractions with 20 mM Hepes, pH 6.8, 1 M NaCl, 2 mM EDTA, 3 mM sodium metabisulfite at 4° C. for 1 hr. Supernatants were pooled and expansin protein was precipitated with 60% ammonium sulfate. Ammonium sulfate pellets were stored at −80° C. and were resuspended with 50 mM sodium acetate buffer pH 5.0 and desalted with a Corning® Spin-X® UF Centrifugal Concentrator 10,000 MWCO Polyethersulfone (PES) Membrane (Corning, Inc. Corning, N.Y.) just before use.

2.2. Enriched Corn Expansin Preparation

Transgenic corn lines which overexpress cucumber expansin were produced by stable transformation with three expression vectors. Each vector was constructed with targeting sequences: 1) endoplasmic reticulum (ER), 2) cell wall and 3) vacuole. ER and cell wall lines were propagated in a greenhouse, self-pollinated and $T_2$ seeds were used as a source of expansin protein.

Enriched corn expansin extract was prepared with the same method used for preparing the cucumber sample without the homogenation/washing step.

2.3. SDS-Polyacrylamide Gel Electrophoresis and Immunoblotting

SDS-PAGE was conducted with the Novex® NuPAGE® SDS-PAGE Gel System (Invitrogen, Carlsbad, Calif.) using 12% NuPAGE® Bis-Tris mini gels. Minigels were stained with Coomassie Brilliant Blue R-250 Staining Solution (Bio-Rad, Richmond, Calif.) to confirm efficient separation. Proteins in unstained gels were electrophoretically transferred using an XCell II™ Blot Module (Invitrogen, Carlsbad, Calif.) to an Immobilion-NY+ nitrocellulose membrane (Millipore, Bedford, Mass.). Transfer was performed in a solution of 48 mM Tris, 39 mM glycine, and 20% (v/v) methanol at 4° C. overnight. After transfer, the membrane was blocked with 10% (v/v) horse serum (TCS Bioscience, Basingstoke, Hampshire, UK) in phosphate-buffered saline (PBS) containing 0.05% (v/v) Tween 20 and 2 mM sodium azide for 2 h. Anti-expansin antibody (1:1000) was added to blocking solution and incubated for 1 hour. The membrane was washed with PBS for 2×5 min and Tris-buffered saline (TBS) for 2×5 min. The blot was incubated with alkaline phosphatase conjugated goat anti-rabbit IgG (Sigma, St. Louis, Mo., 1:10,000 in 10% horse serum in TBS) for 1 h. The membrane was washed 4×5 min. in TBS. Chemiluminescent detection was conducted with CDP-Star (Roche Diagnostics, Indianapolis, Ind.), Nitro Block II (Tropix, Bedford, Mass.) and CDP-Star detection buffer (0.1M Tris, 0.1M NaCl, pH 9.5). The membrane was washed with CDP-Star detection buffer for 2×2 min then placed in a sealable plastic bag. Detection reagent (3 ml CDP-Star detection buffer, 150 µL Nitro Block II, 30 µL CDP-Star) was poured on the membrane and the bag sealed. After incubation for 5 min., chemiluminescent signal was detected with Kodak Biomax XAR film (Sigma, Rochester, N.Y.) and the film was developed with an SRX-101A Medical Film Processor (Konica, Shinjuku-ku, Tokyo, Japan). Molecular weight of the bands was estimated by migration distance analysis. The protein marker for SDS-PAGE was Precision Plus Protein™ Dual Color Standards (Bio-Rad, Richmond, Calif.). Expansin immunoblot protocol and antibody were kindly provided by D. Cosgrove (The Pennsylvania State University).

2.4. Expansin Activity Assay

The expansin activity assay consists of Sigmacell cellulose S3504 (Sigma, St. Louis, Mo.), a complete *Trichoderma reesei* extract, Sigma® C2730 cellulase (Sigma, St. Louis, Mo.), and expansin. Sigmacell cellulose is a microcrystalline cellulose and expansin synergistic activity with cellulase on microcrystalline cellulose was tested, based on the original patent from Cosgrove's laboratory (Cosgrove 2001 [35]). Components were mixed and the final volume was brought up to 200 µL with 50 mM sodium acetate buffer pH 5.0. For the high throughput assay, a 96 well microtiter plate (Corning® 96 well EIA/RIA plates, CLS9017, Corning Industry) was used with TempPlate RT Select optically clear film (USA Scientific, Inc. Orlando Fla.) to seal the wells. To measure the cellulase activity as increased by expansin synergy, the glucose amount from 1) blank (Sigmacell+Buffer), 2) cellulase alone (Sigmacell+Buffer+Cellulase), 3) expansin without cellulase (Sigmacell+Buffer+Expansin) and 4) expansin with cellulase (Sigmacell+Buffer+Cellulase+Expansin) were measured. Enriched transgenic corn extract and native corn extract were used as positive and negative control samples, respectively. Each plate was incubated using a shaking incubater (model 12400, New Brunswick Scientific, Edison N.J.) at 37° C. with agitation at 225 RPM. After incubation, plates were left on the bench for 20 min at room temperature to precipitate the Sigmacell cellulose. A specific volume of supernatant was then transferred to a new 96 well plate and 60 µl glucose oxidase solution of the GAGO-20 Glucose assay kit (Sigma, St. Louis, Mo.) was added to each well. This plate was sealed and incubated at 37° C. for 30 min without shaking After incubation, 60 µl of 12 N sulfuric acid was added to each well to stop the reaction. The developed pink color was measured at O.D. 540 nm using a Synergy HT Multi-Mode Microplate Reader (Biotek Instruments Inc., Winooski. Vt.).

Expansin activity was expressed as the ratio of the glucose amount released from cellulose by expansin synergistic activity with cellulase compared to cellulase alone. Expansin activity was calculated as:

$$\text{Expansin activity} = \frac{Sc - So}{Co} \quad \text{Equation 1}$$

where Sc is an average signal of the wells which had expansin and cellulase added together; So is an average signal of the wells which had expansin only; Co is an average signal of the wells which had cellulase only.

3. Results 3.1. Development of Novel Expansin Assay

A novel, high-throughput expansin assay was developed which is sensitive enough to detect activity of non-purified crude expansin. To develop this assay, the glucose oxidase assay was modified to detect glucose released from cellulose by expansin synergy with cellulase. In this novel expansin assay, expansin activity was determined by comparing the activity of recombinant corn expansin to that of endogenous protein extract.

This novel expansin assay was composed of 1) cellulose hydrolysis by expansin synergy with crude fungal cellulases and 2) determination of the glucose amount released from cellulose. The expansin assay was conducted as described, but with a variety of ranges tested for each factor listed.

Assay optimization was performed to determine the best 1) incubation time, 2) cellulase amount, 3) transfer volume of incubated solution to the glucose oxidase assay, 4) glass bead effect to agitate the incubation solution, and 5) effect of pre-incubation of cellulose and expansin sample prior to adding cellulase. For assay optimization experiments, expansin activity was determined by comparing the activity of extracts of transgenic corn expressing cucumber expansin to endogenous activity of native corn extracts. For assay validation, expansin activity was calculated as described in Materials and Methods, using cucumber extract.

3.2. Incubation Time Optimization

Figure 7:
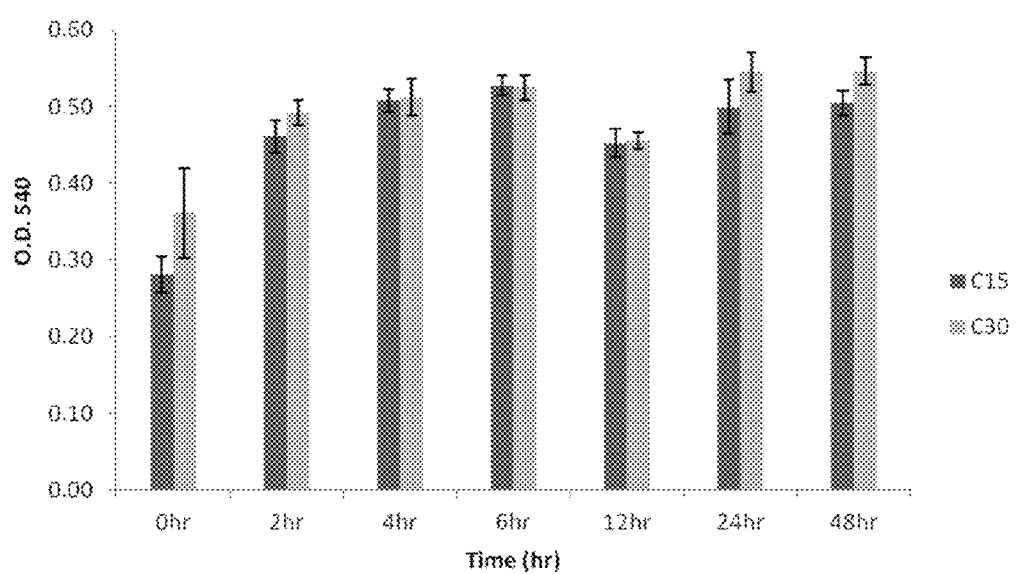
FIG. 7 shows the incubation time optimization. Glucose released from cellulose was determined using a glucose oxidase assay kit. Microcrystalline cellulose was incubated with two different concentrations of crude fungal cellulase and samples were collected at times as shown on the X-axis. Error bars represent standard deviation of triplicated samples. C15, 15 µL of 1:200 diluted cellulase; C30, 30 µL of 1:200 diluted cellulase. Cellulase preparation was from T. reesei and purchased from Sigma Chemical Co.

Sigmacell microcrystalline cellulose and cellulases were incubated for 0, 2, 4, 6, 12, 24 and 48 hrs with 15 µL and 30 µL of 1:200 diluted cellulases. Thirty microliters of supernatant was transferred to new 96 well microplates. Glucose amount in the supernatant was determined by using the glucose oxidase assay as described in Materials and Methods. The optical density (O.D.) at 540 nm of each sample was compared (FIG. 7). FIG. 7 shows the incubation time optimization. Glucose released from cellulose was determined using a glucose oxidase assay kit. Microcrystalline cellulose was incubated with two different concentrations of crude fungal cellulase and samples were collected at times as shown on the X-axis. Error bars represent standard deviation of triplicated samples. C15, 15 µL of 1:200 diluted cellulase; C30, 30 µL of 1:200 diluted cellulase. Cellulase preparation was from *T. reesei* and purchased from Sigma Chemical Co.

The assays were saturated after 2 hr incubation time. The saturated assays were purple in color and showed no difference between the two cellulase concentrations as well. The working range of the glucose oxidase assay was determined with a serially diluted glucose standard solution. This assay has a relatively narrow working range up to 25 ug of glucose and a maximum O.D. of 0.5 at O.D. 540 nm (data not shown). For further assay optimization experiments, the 2 hr incubation was used.

3.3 Optimal Cellulase Amount

The optimal crude fungal cellulase amount to show minimum activity was determined by adding 0.0024, 0.0012, 0.024, 0.12, 0.24, 1.2, 2.4 and 12 mg of cellulase to each test. Based on the glucose amount released by this cellulase preparation, the linear range of cellulase activity was determined. Enzyme amounts over 1.2 mg of cellulase released enough glucose to saturate the assay (FIG. 8A).

Figure 8:
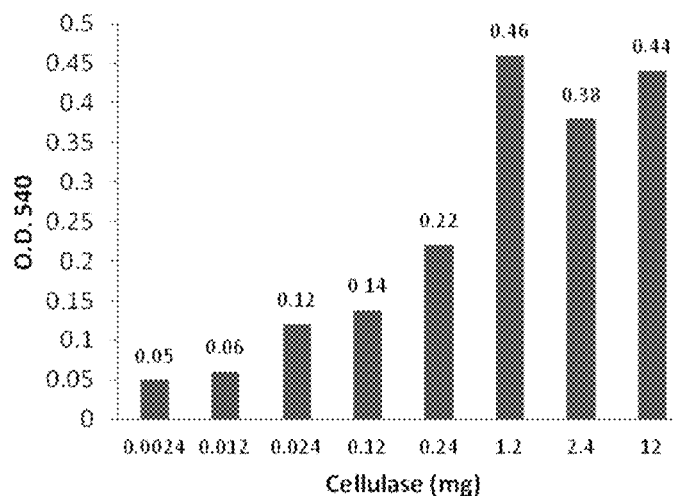
FIGS. 8A&B shows the optimal crude fungal cellulase amount determination. Glucose amount is represented by signal strength at O.D. 540.
(FIG. 8B) Signals from 0.012 to 1.2 mg of cellulase were analyzed by regression analysis. Sigma cellulose and cellulase were incubated for 2 hrs and glucose amount in the supernatant was determined. Cellulase preparation was from T. reesei and purchased from Sigma Chemical Co.
Figure 8:
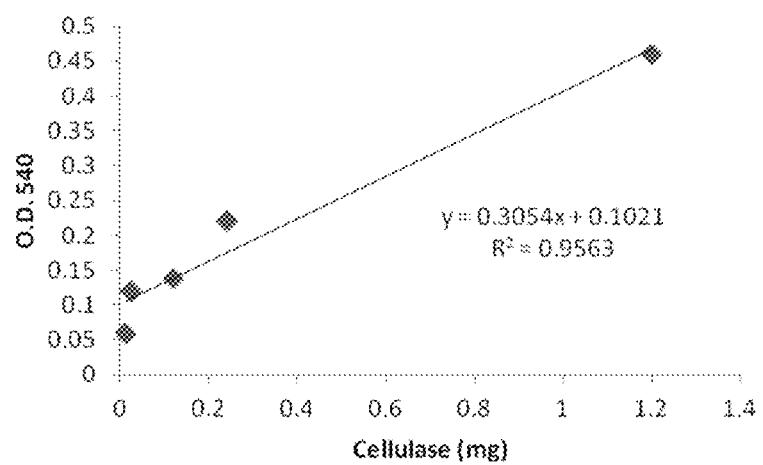

FIG. 8B shows the relationship between cellulase amount and signal strength. In the unsaturated region (0.012 to 1.2 mg of cellulase), excellent linearity was shown. In subsequent experiments, 0.018 mg of cellulase was used because this is a minimum amount of cellulase which shows glucose release. The use of the smallest amount possible of cellulase facilitated the measurement of expansin synergistic effect by providing more room to observe the increase of the amount of glucose by expansin activity. FIGS. 8A&B shows the optimal crude fungal cellulase amount determination. Glucose amount is represented by signal strength at O.D. 540. (FIG. 8A) Various amounts of crude fungal cellulase were used to release glucose from Sigmacell microcrystalline cellulose. (FIG. 8B) Signals from 0.012 to 1.2 mg of cellulase were analyzed by regression analysis. Sigma cellulose and cellulase were incubated for 2 hrs and glucose amount in the supernatant was determined. Cellulase preparation was from *T. reesei* and purchased from Sigma Chemical Co.

3.4. Optimal Crude Expansin Sampling Volume

Figure 9:
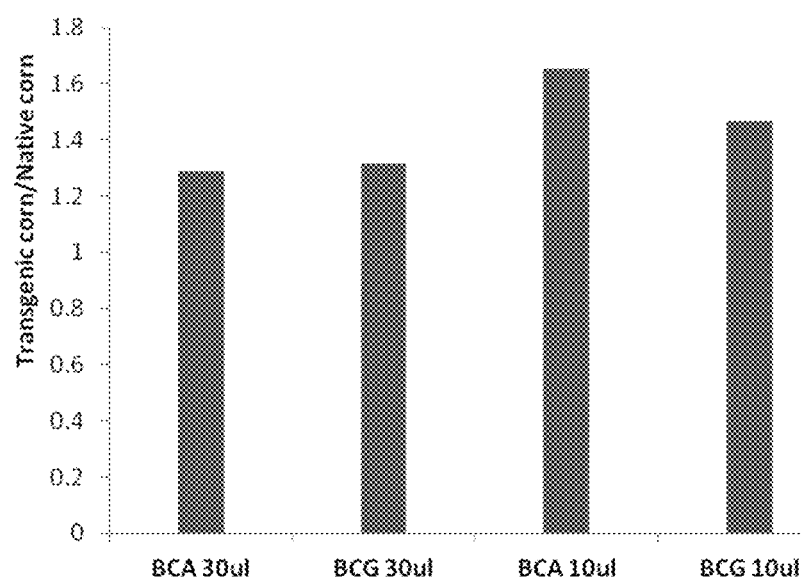
FIG. 9 shows the sampling volume determination for crude corn extract containing recombinant expansin. Ten and 30 ul of sampling volume were compared. BCA, enriched extract of transgenic line seeds (cell wall targeted protein); BCG, enriched extract of transgenic line seeds (ER targeted protein). Values represent the fold increases in cellulase activity when expansin is added. Each bar is the ratio of glucose released from Sigmacell microcrystalline cellulose when transgenic corn extract is added to crude fungal cellulases compared to the native corn extract added to crude fungal cellulases. Each reaction was an average of three replicates. Cellulase preparation was from T. reesei and purchased from Sigma Chemical Co.

This assay measures the activity of expansin protein by measuring the glucose amount released by expansin synergy with cellulase. Since the assay is easily saturated, the right amount of crude expansin extract (sample) should be added to the assay to ensure measurable activity. Twenty ug of enriched recombinant (cell wall and ER lines) and non-recombinant (LH283) corn extract were used as positive and negative expansin samples, respectively. After incubating the cellulose with expansin samples and 0.018 mg of cellulase, 30 and 10 µL of supernatant were transferred to the detection plate and glucose concentration was analyzed with the glucose oxidase assay kit (FIG. 9). FIG. 9 shows the sampling volume determination for crude corn extract containing recombinant expansin. Ten and 30 ul of sampling volume were compared. BCA, enriched extract of transgenic line seeds (cell wall targeted protein); BCG, enriched extract of transgenic line seeds (ER targeted protein). Values represent the fold increases in cellulase activity when expansin is added. Each bar is the ratio of glucose released from Sigmacell microcrystalline cellulose when transgenic corn extract is added to crude fungal cellulases compared to the native corn extract added to crude fungal cellulases. Each reaction was an average of three replicates. Cellulase preparation was from *T. reesei* and purchased from Sigma Chemical Co.

Expansin activity was represented by the signal ratio of transgenic to native corn extract because native extract also shows some endogenous activity of unknown origin. This result, (FIG. 9) showed that the assay was saturated with too much glucose when 30 µL of sample was added to the glucose oxidase assay changing the color from purple to brown, so the apparent ratio of transgenic to native corn extract was lower than that in the 10 µL samples. Thus, in subsequent experiments, 10 µL of sample was used for glucose detection.

3.5. Agitation Effect of Glass Bead

Figure 10:
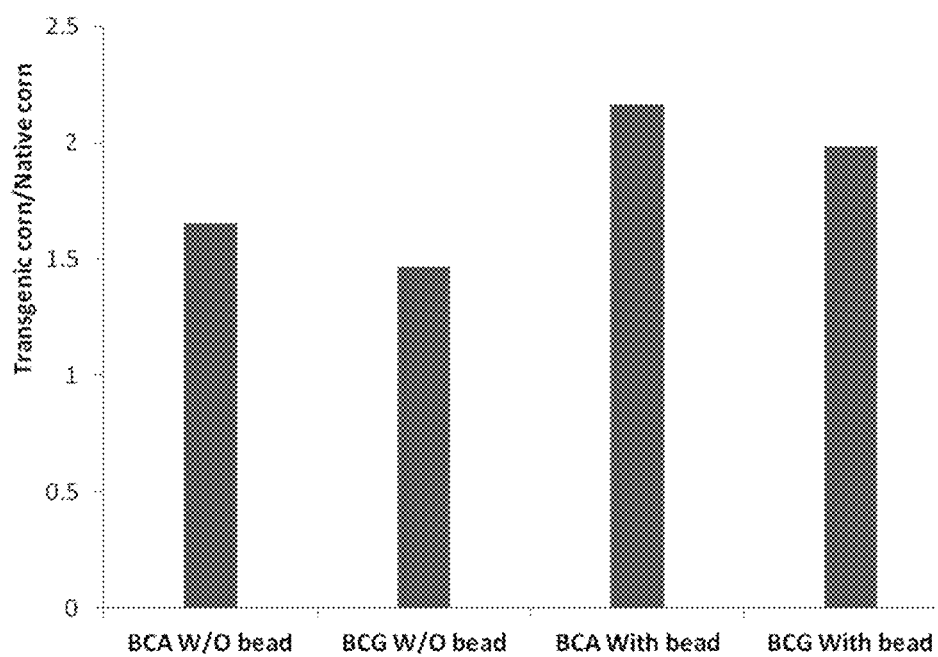
FIG. 10 shows the glass bead effect on glucose release from cellulose. Assays including microcrystalline cellulose and cellulose+crude expansin were incubated with or without glass beads. BCA, enriched extract of transgenic line seeds (cell wall targeted protein); BCG, enriched extract of transgenic line seeds (ER targeted protein). Twenty ug of transgenic and native corn extract were incubated with crude fungal cellulase for 2 hrs and 10 µL of supernatant was used for glucose detection. Values represent the fold increases in cellulase activity when expansin is added. Each bar is the ratio of glucose released from Sigmacell microcrystalline cellulose when transgenic corn extract is added to crude fungal cellulases compared to the native corn extract added to crude fungal cellulases. Each reaction was an average of three replicates. Cellulase preparation was from T. reesei and purchased from Sigma Chemical Co.

It was found that water insoluble microcrystalline cellulose did not remain suspended in each well and kept settling out. The effect of agitation with a glass bead was tested because it could agitate the cellulose suspension efficiently. Expansin activity was compared with or without glass beads in every well. FIG. 10 shows that incubation with a glass bead provides a better condition to detect expansin activity. In fact, ~40% higher glucose release was achieved with agitation. FIG. 10 shows the glass bead effect on glucose release from cellulose. Assays including microcrystalline cellulose and cellulose+crude expansin were incubated with or without glass beads. BCA, enriched extract of transgenic line seeds (cell wall targeted protein); BCG, enriched extract of transgenic line seeds (ER targeted protein). Twenty ug of transgenic and native corn extract were incubated with crude fungal cellulase for 2 hrs and 10 µL of supernatant was used for glucose detection. Values represent the fold increases in cellulase activity when expansin is added. Each bar is the ratio of glucose released from Sigmacell microcrystalline cellulose when transgenic corn extract is added to crude fungal cellulases compared to the native corn extract added to crude fungal cellulases. Each reaction was an average of three replicates. Cellulase preparation was from *T. reesei* and purchased from Sigma Chemical Co.

3.6. Pre-Incubation of Expansin with Cellulose

Figure 11:
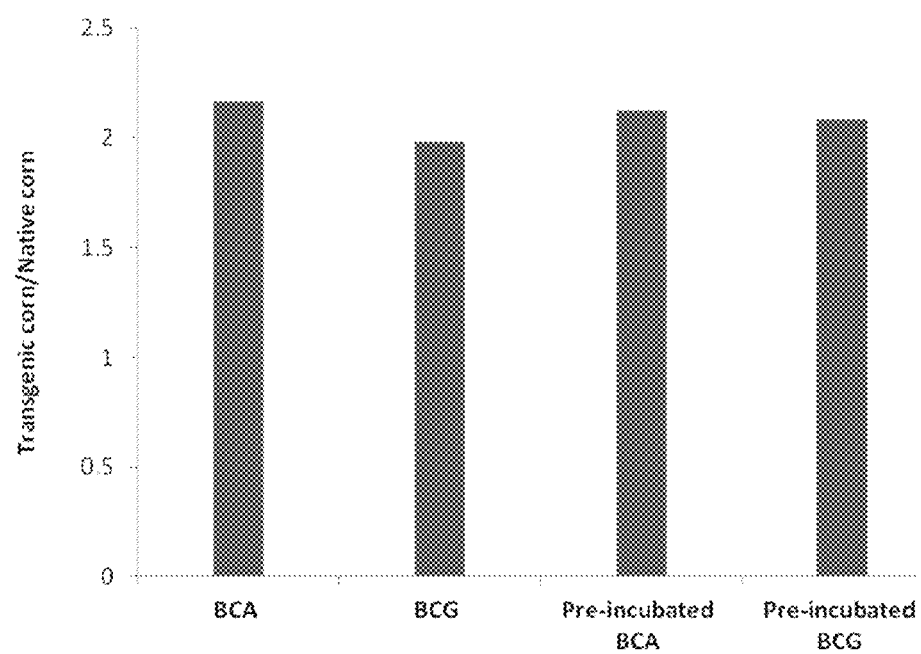
FIG. 11 shows the pre-incubation effect of cellulose and expansin on the release of glucose. Expansin samples and microcrystalline cellulose were incubated for 1 hr at 37° C. before adding cellulase. BCA, enriched extract of transgenic line seeds (cell wall targeted protein); BCG, enriched extract of transgenic line seeds (ER targeted protein). Twenty ug of transgenic and native corn extract were incubated with substrate for 1 hr before addition of crude fungal celluase. Values represent the fold increases in cellulase activity when expansin is added. Each bar is the ratio of glucose released from Sigmacell microcrystalline cellulose when transgenic corn extract is added to crude fungal cellulases compared to the native corn extract added to crude fungal cellulases. Each reaction was an average of three replicates. Cellulase preparation was from *T. reesei* and purchased from Sigma Chemical Co.

Wall loosening activity of expansin was reported even though its mode of action is uncertain (Cosgrove et al. 2002 [177]). It was hypothesized that incubation of expansin with cellulose before adding cellulase may increase the accessibility of cellulase to cellulose. To test this hypothesis, positive and negative corn extracts were incubated with cellulose at 37° C. for 1 hr prior to adding the crude fungal cellulase. FIG. 11 shows that 1 hr pre-incubation did not increase the sensitivity of the assay. Because expansin protein induces plant cell wall expansion rapidly (McQueen-Mason et al. 1992 [2]), pre-incubation may not have an advantage over direct incubation with cellulase. FIG. 11 shows the pre-incubation effect of cellulose and expansin on the release of glucose. Expansin samples and microcrystalline cellulose were incubated for 1 hr at 37° C. before adding cellulase. BCA, enriched extract of transgenic line seeds (cell wall targeted protein); BCG, enriched extract of transgenic line seeds (ER targeted protein). Twenty ug of transgenic and native corn extract were incubated with substrate for 1 hr before addition of crude fungal cellualse. Values represent the fold increases in cellulase activity when expansin is added. Each bar is the ratio of glucose released from Sigmacell microcrystalline cellulose when transgenic corn extract is added to crude fungal cellulases compared to the native corn extract added to crude fungal cellulases. Each reaction was an average of three replicates. Cellulase preparation was from *T. reesei* and purchased from Sigma Chemical Co.

3.7. Optimized Expansin Assay

The optimized expansin assay has the following conditions.

1) Incubation of cellulose with crude expansin and crude fungal cellulase 20 ug of unknown or expansin protein extract
1.25 mg of microcrystalline cellulose (e.g. Sigmacell)
18 ug of cellulase (Sigma C2730)
Glass bead (4 mm)
200 µL total volume (adjusted with sodium acetate buffer pH 5.0)
Sealed plate with plastic film
Incubation at 37° C. for 2 hr with shaking (250 rpm)

2) Detection of glucose released by expansin synergy with cellulase

Allow cellulose to settle out at room temperature.
Transfer 10 µL of supernatant to new 96 well plate
Add 60 µL of glucose oxidase solution (e.g. Sigma GAGO-20 Glucose assay kit)
Incubate 30 min at 37° C.
Add 60 µL of 12N sulfuric acid
Measure O.D. at 540 nm
Calculate synergy value 3.8. Expansin Assay Validation Enriched cucumber extract was used to validate the novel assay. Expansin protein presence in enriched cucumber extract was confirmed by western blot using an anti-expansin antibody. Assay validation was performed by determining the relationship between expansin amount and signal strength of different amounts of enriched cucumber extract, 5, 10, 20 and 40 µL and 20 µL of heat denatured extract. The optimized assay conditions were used to perform this experiment.

Figure 12:
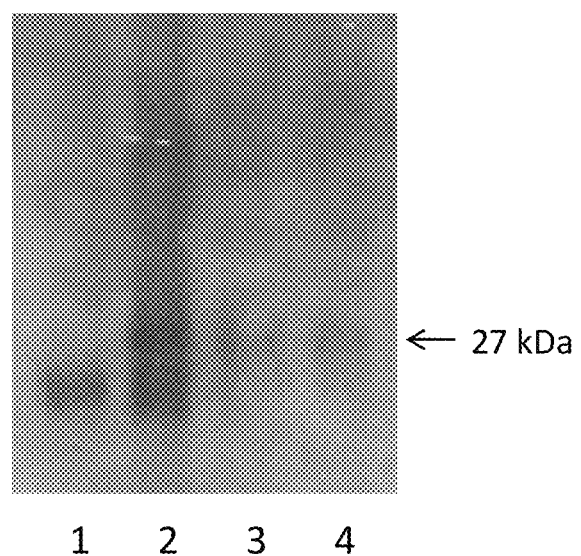
FIG. 12 shows a Western blot of expansin fractions recovered from cucumber hypocotyls. A total of 4 samples were collected from fractionation steps (Table 11, last column) and analyzed by western blot using anti-expansin antibody. Samples were designated as follows: #1 supernatant=1 hr incubation with homogenation buffer and filtration with Miracloth (3×), #2 supernatant=1 hr incubation of filtered tissue with extraction buffer (3×) then centrifugation, #3 supernatant=Ammonium sulfate precipitation (60%) and centrifugation, and #4 supernatant=Resuspended/desalted pellet. To confirm the presence of expansin protein, 10 µL of each fraction was loaded in each well. Sample 4 showed the highest synergy shown in FIG. 13.

Cucumber extract was prepared according to the expansin extraction and fractionation protocol of McQueen-Mason et al. 1992 [2]. Washing buffer (homogenation buffer) removes non-cell wall bound protein from ground cucumber tissues and extraction buffer releases expansin protein from cucumber cell walls. Also, 60% ammonium sulfate precipitation was expected to concentrate expansin protein. To confirm the efficiency of these enrichment steps and the presence of expansin protein, samples were collected at each step (Table 11) and analyzed by western blot (FIG. 12). FIG. 12 shows a Western blot of expansin fractions recovered from cucumber hypocotyls. A total of 4 samples were collected from fractionation steps (Table 11, last column) and analyzed by western blot using anti-expansin antibody. Samples were designated as follows: #1 supernatant=1 hr incubation with homogenation buffer and filtration with Miracloth (3×), #2 supernatant=1 hr incubation of filtered tissue with extraction buffer (3×) then centrifugation, #3 supernatant=Ammonium sulfate precipitation (60%) and centrifugation, and #4 supernatant=Resuspended/desalted pellet. To confirm the presence of expansin protein, 10 µL of each fraction was loaded in each well. Sample 4 showed the highest synergy shown in FIG. 13.

Western blot results showed 27 kDa bands in the salt extract and the ammonium sulfate pellet and supernatant but not in the crude extract with homogenation buffer, confirming the presence of native cucumber expansin. The enriched cucumber extract was used to validate the expansin assay.

Figure 13:
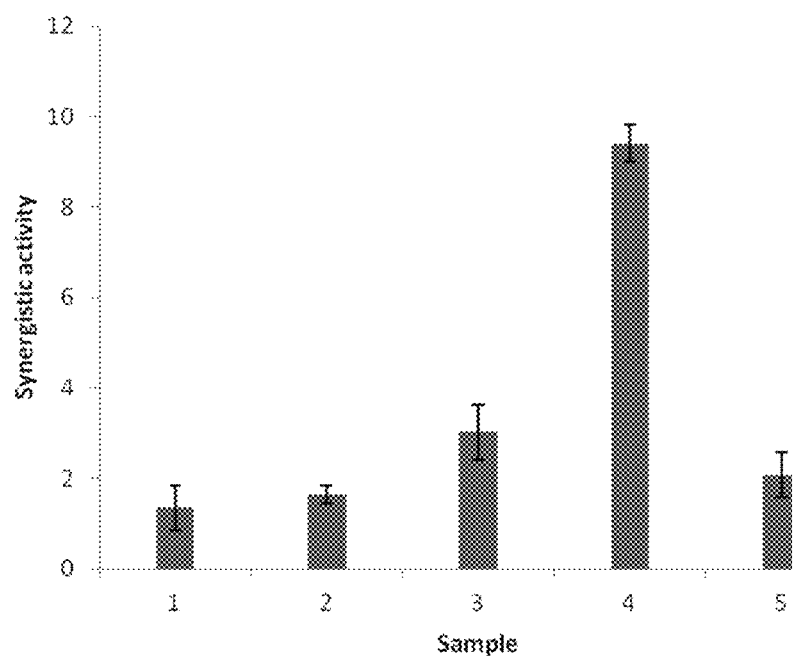
FIG. 13 shows the synergistic activity driving release of glucose from microcrystalline cellulose of native corn extract and cucumber samples from enrichment steps interacting with crude fungal cellulases. Expansin activity of samples from enrichment steps and native corn extract were analyzed with the novel expansin activity assay using 20 ug of total protein. The samples are identified as follows: 1 is the crude extract—homogenation buffer, 2 is the crude extract—extraction buffer, 3 is the supernatant after 60% ammonium sulfate precipitation, 4 is the re-suspended 60% ammonium sulfate pellet, and 5 is the native corn extract
Figure 14:
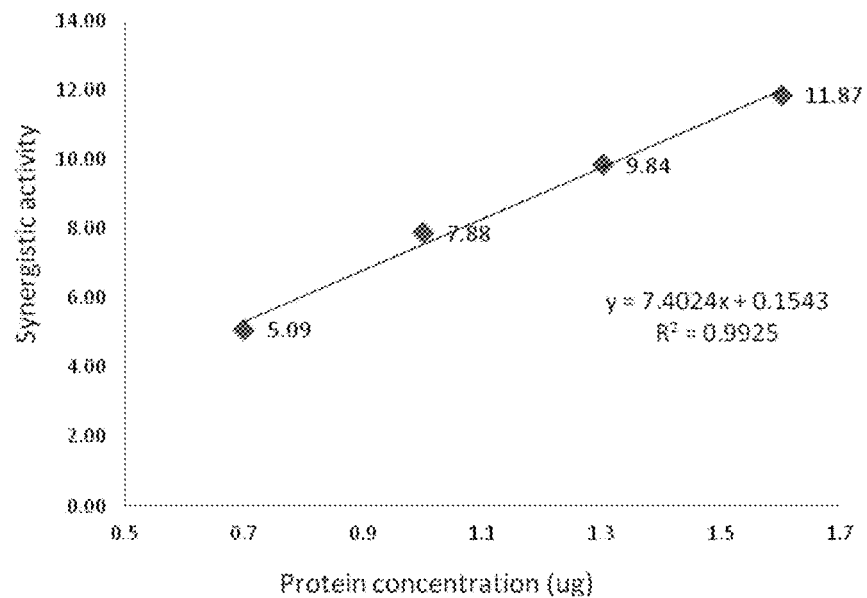
FIG. 14 shows a regression analysis of a dose-response analysis of increasing amounts of enriched expansin in the synergy assay for glucose release from cellulose. Various amounts of resuspended ammonium sulfate pellet (5, 10, 20 and 40 ug) and 20 ug of heat denatured cucumber extract were analyzed with the novel expansin activity assay. Protein concentration is represented as a log scale. Synergistic activity is represented as the increase in glucose release above that released by crude fungal cellulases alone.

The expansin activity of native corn extract and samples from the cucumber extract enrichment steps were compared in the novel expansin activity assay (FIG. 13). Native corn extract (sample #5) was prepared with the same protocol as for the cucumber extract and the resuspended ammonium sulfate pellet was used in this experiment. Based on these results it was shown that 1) the expansin enrichment protocol recovered a concentrated expansin protein and 2) the novel expansin assay can distinguish the recombinant corn expansin from native corn activity. FIG. 13 shows the synergistic activity driving release of glucose from microcrystalline cellulose of native corn extract and cucumber samples from enrichment steps interacting with crude fungal cellulases. Expansin activity of samples from enrichment steps and native corn extract were analyzed with the novel expansin activity assay using 20 ug of total protein. The samples are identified as follows: 1 is the crude extract—homogenation buffer, 2 is the crude extract—extraction buffer, 3 is the supernatant after 60% ammonium sulfate precipitation, 4 is the re-suspended 60% ammonium sulfate pellet, and 5 is the native corn extract The resuspended ammonium sulfate pellet of native cucumber extract was used to test its dose-response activity (FIG. 14). For this analysis, 5, 10, 20 and 40 ug of extracted protein, and 20 ug of heat denatured cucumber extract were tested using the novel expansin activity assay. Denatured extract did not show any synergistic activity and increasing extract amounts increased the synergistic activity. FIG. 14 shows a regression analysis of a dose-response analysis of increasing amounts of enriched expansin in the synergy assay for glucose release from cellulose. Various amounts of resuspended ammonium sulfate pellet (5, 10, 20 and 40 ug) and 20 ug of heat denatured cucumber extract were analyzed with the novel expansin activity assay. Protein concentration is represented as a log scale. Synergistic activity is represented as the increase in glucose release above that released by crude fungal cellulases alone.

TABLE 11

Fractionation steps of cucumber expansin

| | Fractionation steps | Samples |
|---|---|---|
| 1. | 300 g of freshly ground etiolated cucumber hypocotyl | |
| 2. | 1 hr incubation with homogenation buffer and filtration with Miracloth (3X) | #1. supernatant |
| 3. | 1 hr incubation of filtered tissue with extraction buffer (3X) then centrifugation | #2. supernatant |
| 4. | Ammonium sulfate precipitation (60%) and centrifugation | #3. supernatant |
| 5. | Resuspended/desalted pellet | #4. supernatant |

4. Discussion

Expansin is a protein that is active in cell wall expansion in the growing regions of most plants. It has also been shown to have synergistic activity with cellulase. Over-expression of expansin in the maize production system allows recovery of sufficient protein 1) to study its physiological effects, and 2) to assess its ability to serve as an industrial enzyme for applications, particularly in biomass conversion. Transgenic lines of maize that express the cucumber expansin gene have been recovered The gene is expressed from an embryo-preferred promoter, globulin-1, and the protein targeted to three sub-cellular locations: the cell wall, the vacuole and the endoplasmic reticulum (ER). About four hundred plants were recovered and first generation seed was harvested from them. Levels of expansin in these seeds have not been assessed because of the lack of an efficient expansin activity assay system. The traditional activity assay for expansin is cumbersome and slow, thus it is not practical for screening large numbers of samples.

Therefore, a novel high throughput expansin activity assay system was developed which measures the glucose amount released from cellulose by expansin synergy with cellulase. The assay was optimized and validated. This assay can successfully detect expansin synergistic activity and distinguish the difference between an endogenous activity and transgenic expansin. The novel expansin activity assay can now be used to screen transgenic plants or other recombinant systems to choose those that are best for industrial scale-up.

Although the invention has been described with reference to these preferred embodiments, other embodiments can achieve the same results. Variations and modifications of the present invention will be obvious to those skilled in the art and it is intended to cover in the appended claims all such modifications and equivalents. The entire disclosures of all applications, patents, and publications cited above, and of the corresponding application are hereby incorporated by reference.

REFERENCES

1. Cosgrove, D. J. (2000) "Loosening of plant cell walls by expansins," *Nature* 407(6802), 321-326.
2. McQueen-Mason, S. et al. (1992) "Two endogenous proteins that induce cell wall extension in plants," *Plant Cell* 4(11), 1425-1433.
3. Cho, H. T. and Kende, H. (1997) "Expression of expansin genes is correlated with growth in deepwater rice," *Plant Cell* 9(9), 1661-1671.
4. Downes, B. and Crowell, D. (1998) "Cytokinin regulates the expression of a soybean β-expansin gene by a post-transcriptional mechanism," *Plant Mol. Biol* 37(3), 437-444.
5. Cho, H.-T. and Cosgrove, D. J. (2002) "Regulation of Root Hair Initiation and Expansin Gene Expression in *Arabidopsis*," *Plant Cell* 14(12), 3237-3253.
6. Sun, Y. et al. (2005) "Brassinosteroid Regulates Fiber Development on Cultured Cotton Ovules," *Plant Cell Physiol* 46(8), 1384-1391.
7. Smith, T. F. and Waterman, M. S. (1981) "Comparison of biosequences," *Adv. Appl. Math.* 2(4), 482-489.
8. Needleman, S. B. and Wunsch, C. D. (1970) "A general method applicable to the search for similarities in the amino acid sequence of two proteins," *J. Mol. Biol.* 48(3), 443-453.
9. Pearson, W. R. and Lipman, D. J. (1988) "Improved tools for biological sequence comparison," *P.N.A.S.* 85(8), 2444-2448.
10. Anderson, M. L. M. and Young, B. D. (1985) "Quantitative Filter Hybridization," in *Nucleic Acid Hybridisation: A Practical Approach* (Hames, B. D. and Higgins, S. J., Eds.), pp 73-111, Oxford University Press, USA.
11. Kacian, D. L. et al. (1972) "A Replicating RNA Molecule Suitable for a Detailed Analysis of Extracellular Evolution and Replication," *Proc. Natl. Acad. Sci. U.S.A* 69(10), 3038-3042.
12. Chamberlin, M. et al. (1970) "New RNA Polymerase from *Escherichia coli* infected with Bacteriophage T7," *Nature* 228(5268), 227-231.
13. Wu, D. Y. and Wallace, R. B. (1989) "The ligation amplification reaction (LAR)—Amplification of specific DNA sequences using sequential rounds of template-dependent ligation," *Genomics* 4(4), 560-569.
14. Erlich, H. A., (Ed.) (1989) *PCR Technology: Principles and Applications for DNA Amplification*, Stockton Press, New York.
15. Mullis, K. B. et al. "Process for amplifying, detecting, and/or -cloning nucleic acid sequences," U.S. Pat. No. 4,683,195, application Ser. No. 06/828,144, filed Feb. 7, 1986. (issued Jul. 28, 1987).
16. Mullis, K. B. "Process for amplifying nucleic acid sequences," U.S. Pat. No. 4,683,202, application Ser. No. 06/791,308, filed Oct. 25, 1985. (issued Jul. 28, 1987).
17. Mullis, K. B. et al. "Process for amplifying, detecting, and/or cloning nucleic acid sequences using a thermostable enzyme," U.S. Pat. No. 4,965,188, application Ser. No. 07/063,647, filed Jun. 17, 1987. (issued Oct. 23, 1990).
18. Maniatis, T. et al. (1987) "Regulation of inducible and tissue-specific gene expression," *Science* 236(4806), 1237-1245.
19. Voss, S. D. et al. (1986) "The role of enhancers in the regulation of cell-type-specific transcriptional control," *Trends Biochem. Sci.* 11(7), 287-289.
20. Bustos, M. M. et al. (1989) "Regulation of beta-glucuronidase expression in transgenic tobacco plants by an A/T-rich, cis-acting sequence found upstream of a French bean beta-phaseolin gene," *Plant Cell Environ.* 1(9), 839-853.
21. Fraley, R. T. et al. "Plant proteins, promoters, coding sequences and use," U.S. Pat. No. 5,352,605, application Ser. No. 08/146,621, filed Oct. 27, 1993. (issued Oct. 4, 1994).
22. Gelvin, S., B. et al. "Chimeric Regulatory Regions and Gene Cassettes for Expression of Genes in Plants," WIPO PCT Patent Publication Number WO/1995/014098, Application PCT/US1994/012946, filed Nov. 17, 1994. (published May 26, 1995).

23. Garbarino, J. E. and Belknap, W. R. (1994) "Isolation of a ubiquitin-ribosomal protein gene (ubi3) from potato and expression of its promoter in transgenic plants," *Plant Mol. Biol* 24(1), 119-127.
24. Sambrook, J. et al. (1989) in *Molecular Cloning: A Laboratory Manual* (Sambrook, J., et al., Eds.) 2nd ed., pp 16.07-16.08, Cold Spring Harbor Laboratory Press, New York.
25. Graham, F. L. and van der Eb, A. J. (1973) "A new technique for the assay of infectivity of human adenovirus 5 DNA," *Virology* 52(2), 456-467.
26. Mccabe, D. E. "Gas driven gene delivery instrument," U.S. Pat. No. 5,584,807, application Ser. No. 08/376,319, filed Jan. 20, 1995. (issued Dec. 17, 1996).
27. de Wet, J. R. et al. (1987) "Firefly luciferase gene: structure and expression in mammalian cells," *Mol. Cell. Biol.* 7(2), 725-737.
28. Hirokawa, K. et al. "Mutant-type bioluminescent protein, and process for producing the mutant-type bioluminescent protein," U.S. Pat. No. 6,074,859, application Ser. No. 09/111,752, filed Jul. 8, 1998. (issued Jun. 13, 2000).
29. Szalay, A. A. et al. "Construction and expression of *renilla luciferase* and green fluorescent protein fusion genes," U.S. Pat. No. 5,976,796, application Ser. No. 08/771,850, filed Dec. 23, 1996. (issued Nov. 2, 1999).
30. Deluca, M. et al. "DNA sequences encoding coleoptera luciferase activity," U.S. Pat. No. 5,674,713, application Ser. No. 08/460,214, filed Jun. 2, 1995. (issued Oct. 7, 1997).
31. Scheirer, W. "Bioluminescence measurement system," U.S. Pat. No. 5,618,682, application Ser. No. 08/193,679, filed Feb. 8, 1994. (issued Apr. 8, 1997).
32. Sambrook, J. et al. (1989) "Synthesis of Single-stranded RNA Proves by In Vitro Transcription," in *Molecular Cloning: A Laboratory Manual* (Sambrook, J., et al., Eds.) 2nd ed., pp 9.31-58, Cold Spring Harbor Laboratory Press, New York.
33. Sambrook, J. et al. (1989) "Transfer and Fixation of Denatured RNA to Membranes," in *Molecular Cloning: A Laboratory Manual* (Sambrook, J., et al., Eds.) 2nd ed., pp 7.39-52, Cold Spring Harbor Laboratory Press, New York.
34. Cosgrove, D. J. (2005) "Growth of the plant cell wall," *Nat. Rev. Mol. Cell Biol.* 6(11), 850-861.
35. Cosgrove, D. J. "Enhancement Of Accessibility Of Cellulose By Expansins," U.S. Pat. No. 6,326,470, application Ser. No. 09/429,675, filed Oct. 28, 1999. (issued Dec. 4, 2001).
36. Cosgrove, D. (1989) "Characterization of long-term extension of isolated cell walls from growing cucumber hypocotyls," *Planta* 177(1), 121-130.
37. Shcherban, T. Y. et al. (1995) "Molecular cloning and sequence analysis of expansins—a highly conserved, multigene family of proteins that mediate cell wall extension in plants," *P.N.A.S.* 92(20), 9245-9249.
38. Kende, H. et al. (2004) "Nomenclature for members of the expansin superfamily of genes and proteins," *Plant Mol. Biol* 55(3), 311-314.
39. Rochange, S. F. et al. (2001) "Impaired growth in transgenic plants over-expressing an expansin isoform," *Plant Mol. Biol* 46(5), 581-589.
40. Tomme, P. et al. (1995) "Cellulose hydrolysis by bacteria and fungi," *Adv. Microb. Physiol.* 37, 1-81.
41. Cosgrove, D. J. (1999) "Enzymes and Other Agents That Enhance Cell Wall Extensibility," *Annu. Rev. Plant Physiol. Plant Mol. Biol.* 50(1), 391-417.
42. Kusnadi, A. R. et al. (1997) "Production of recombinant proteins in transgenic plants: Practical considerations," *Biotechnol. Bioeng.* 56(5), 473-484.
43. Howard, J. A. "Methods Of Commercial Production And Extraction Of Protein From Seed" WIPO PCT Patent Publication Number WO/1998/039461, Application PCT/US1997/004526, filed Mar. 20, 1997. (published Sep. 11, 1998).
44. Hood, E. E. et al. (1997) "Commercial production of avidin from transgenic maize: characterization of transformant, production, processing, extraction and purification," *Mol. Breed.* 3, 291-306.
45. Sambrook, J. et al., (Eds.) (1989) *Molecular Cloning: A Laboratory Manual,* 2nd ed., Cold Spring Harbor Laboratory Press, New York.
46. Innis, M. et al. (1999) *PCR Applications: Protocols for Functional Genomics,* Academic Press, New York.
47. Innis, M. et al. (1995) *PCR Strategies,* Academic Press, New York.
48. Murray, E. E. et al. (1989) "Codon usage in plant genes," *Nucleic Acids Res.* 17(2), 477-498.
49. Meinkoth, J. and Wahl, G. (1984) "Hybridization of nucleic acids immobilized on solid supports," *Anal. Biochem.* 138(2), 267-284.
50. Ausubel, F. M. et al., (Eds.) (1993) *Current Protocols in Molecular Biology,* John Wiley & Sons, New York.
51. Morrison, D. A. and Ellis, J. T. (1997) "Effects of nucleotide sequence alignment on phylogeny estimation: a case study of 18S rDNAs of apicomplexa," *Mol. Biol. Evol.* 14(4), 428-441.
52. Higgins, D. G. and Sharp, P. M. (1988) "CLUSTAL: a package for performing multiple sequence alignment on a microcomputer," *Gene* 73(1), 237-244.
53. Corpet, F. (1988) "Multiple sequence alignment with hierarchical clustering," *Nucleic Acids Res.* 16(22), 10881-10890.
54. Huang, X. et al. (1992) "Parallelization of a local similarity algorithm," *Comput. Appl. Biosci.* 8(2), 155-165.
55. Pearson, W. R. (1994) "Using the FASTA Program to Search Protein and DNA Sequence Databases," in *Computer Analysis of Sequence Data* (Griffin, A. M. and Griffin, H. G., Eds.), pp 307-331, Humana Press.
56. Sonnhammer, E. L. L. et al. (1998) "Pfam: Multiple sequence alignments and HMM-profiles of protein domains," *Nucleic Acids Res.* 26(1), 320-322.
57. Hein, J. (1994) "TreeAlign," in *Computer Analysis of Sequence Data,* pp 349-364, Springer New York.
58. Altschul, S. F. et al. (1990) "Basic local alignment search tool," *J. Mol. Biol.* 215(3), 403-410.
59. Zhang, J. and Madden, T. L. (1997) "PowerBLAST: A New Network BLAST Application for Interactive or Automated Sequence Analysis and Annotation," *Genome Res.* 7(6), 649-656.
60. Henikoff, S. and Henikoff, J. G. (1992) "Amino acid substitution matrices from protein blocks," *P.N.A.S.* 89(22), 10915-10919.
61. Karlin, S. and Altschul, S. F. (1993) "Applications and statistics for multiple high-scoring segments in molecular sequences," *P.N.A.S.* 90(12), 5873-5877.
62. Henikoff, S. and Henikoff, J. G. (1993) "Performance evaluation of amino acid substitution matrices," *Proteins* 17(1), 49-61.
63. Altschul, S. (1993) "A protein alignment scoring system sensitive at all evolutionary distances," *J. Mol. Evol.* 36(3), 290-300.

64. Mullis, K. B. and Faloona, F. A. (1987) "[21] Specific synthesis of DNA in vitro via a polymerase-catalyzed chain reaction," in *Methods in Enzymology* (Ray, W., Ed.), pp 335-350, Academic Press.
65. Kay, M. A. et al. (1997) "Gene therapy," *P.N.A.S.* 94(24), 12744-12746.
66. Cranage, M. P. et al. (1986) "Identification of the human cytomegalovirus glycoprotein B gene and induction of neutralizing antibodies via its expression in recombinant vaccinia virus," *EMBO J.* 5(11), 3057-3063.
67. Plotkin, S. A. et al. "Recombinant Cytomegalovirus Vaccine," WIPO PCT Patent Publication Number WO/1994/017810, Application PCT/US1994/002107, filed Feb. 10, 1994. (published Aug. 18, 1994).
68. Plotkin, S. A. et al. "Recombinant Cytomegalovirus Vaccine," WIPO PCT Patent Publication Number WO/1994/023744, Application PCT/US1994/004180, filed Apr. 15, 1994. (published Oct. 27, 1994).
69. Abbitt, S. E. and Nair, R. "Pericarp-Preferred Regulatory Element," U.S. Pat. No. 7,550,579, application Ser. No. 11/408,223, filed Apr. 20, 2006. (issued Jun. 23, 2009).
70. Opsahl-Sorteberg, H.-G. et al. (2004) "Identification of a 49-bp fragment of the HvLTP2 promoter directing aleurone cell specific expression," *Gene* 341(0), 49-58.
71. Martino-Catt, S. J. et al. "Seed-Preferred Promoters From End Genes," WIPO PCT Patent Publication Number WO/2000/012733, Application PCT/US1999/019604, filed Aug. 25, 1999. (published Mar. 9, 2000).
72. Fobert, P. R. et al. (1994) "T-DNA tagging of a seed coat-specific cryptic promoter in tobacco," *Plant J.* 6(4), 567-577.
73. Chopra, S. et al. (1996) "Alleles of the maize P gene with distinct tissue specificities encode Myb-homologous proteins with C-terminal replacements," *Plant Cell* 8(7), 1149-1158.
74. Muhitch, M. J. et al. (2002) "Isolation of a Promoter Sequence From the Glutamine Synthetase$_{1-2}$ Gene Capable of Conferring Tissue-Specific Gene Expression in Transgenic Maize," *Plant Science* 163(4), 865-872.
75. Belanger, F. C. and Kriz, A. L. (1991) "Molecular basis for allelic polymorphism of the maize Globulin-1 gene," *Genetics* 129(3), 863-872.
76. Streatfield, S. J. et al. "Globulin-1 Promoter From Maize And Method Of Using Same," U.S. Pat. No. 7,169,967, application Ser. No. 11/085,864, filed Mar. 22, 2005. (issued Jan. 30, 2007).
77. Streatfield, S. J. et al. "Globulin 2 Regulatory Region And Method Of Using Same," U.S. Pat. No. 7,112,723, application Ser. No. 11/190,408, filed Jul. 27, 2005. (issued Sep. 26, 2006).
78. Quail, P. H. et al. "Plant Ubiquitin Promoter System," European Patent Publication Number EP0342926 A2, Application EP19890304930, filed May 16, 1989. (published Nov. 23, 1989).
79. Broglie, R. et al. (1984) "Light-regulated expression of a pea ribulose-1,5-bisphosphate carboxylase small subunit gene in transformed plant cells," *Science* 224(4651), 838-843.
80. Velten, J. and Schell, J. (1985) "Selection-expression plasmid vectors for use in genetic transformation of higher plants," *Nucleic Acids Res.* 13(19), 6981-6998.
81. Guilley, H. et al. (1982) "Transcription of cauliflower mosaic virus DNA: detection of promoter sequences, and characterization of transcripts," *Cell* 30(3), 763-773.
82. Odell, J. T. et al. (1985) "Identification of DNA sequences required for activity of the cauliflower mosaic virus 35S promoter," *Nature* 313(6005), 810-812.
83. Maiti, I. B. et al. (1997) "Promoter/leader deletion analysis and plant expression vectors with the figwort mosaic virus (FMV) full length transcript (FLt) promoter containing single or double enhancer domains," *Transgenic Res.* 6(2), 143-156.
84. Grdzelishvili, V. Z. et al. (2000) "Mapping of the Tobacco mosaic virus movement protein and coat protein subgenomic RNA promoters in vivo," *Virology* 275(1), 177-192.
85. Gurley, W. B. et al. (1986) "Upstream sequences required for efficient expression of a soybean heat shock gene," *Mol. Cell. Biol.* 6(2), 559-565.
86. Caddick, M. X. et al. (1998) "An ethanol inducible gene switch for plants used to manipulate carbon metabolism," *Nat. Biotechnol.* 16(2), 177-180.
87. Kishore, G. M. "Increased Starch Content In Plants," WIPO PCT Patent Publication Number WO/1991/019806, Application PCT/US1991/004036, filed Jun. 7, 1991. (published Dec. 26, 1991).
88. Jefferson, R. A. "Plant Promoter Beta-Glucuronidase Gene Construct," U.S. Pat. No. 5,268,463, application Ser. No. 07/447,976, filed Dec. 8, 1989. (issued Dec. 7, 1993).
89. Jefferson, R. A. "Beta-Glucuronidase And Glucuronide Permease Gene System," U.S. Pat. No. 5,599,670, application Ser. No. 08/329,701, filed Feb. 21, 1995. (issued Feb. 4, 1997).
90. Jefferson, R. A. et al. (1987) "GUS fusions: beta-glucuronidase as a sensitive and versatile gene fusion marker in higher plants," *EMBO J.* 6(13), 3901-3907.
91. Taylor, L. P. and Briggs, W. R. (1990) "Genetic regulation and photocontrol of anthocyanin accumulation in maize seedlings," *Plant Cell* 2(2), 115-127.
92. Dellaporta. (1988) in *Chromosome Structure and Function* (Appels and Gustafson, Eds.), pp 263-282, Kluwer Academic Publishers.
93. Kao, C. Y. et al. (1996) "Localization and interaction of the cis-acting elements for abscisic acid, VIVIPAROUS 1, and light activation of the C1 gene of maize," *Plant Cell* 8(7), 1171-1179.
94. Scheffler, B. et al. (1994) "Molecular analysis of C1 alleles in *Zea mays* defines regions involved in the expression of this regulatory gene," *Mol. Gen. Genet.* 242(1), 40-48.
95. Wienand, U. et al. (1986) "Molecular cloning of the c2 locus of *Zea mays*, the gene coding for chalcone synthase," *Mol. Gen. Genet.* 203(2), 202-207.
96. Chandler, V. L. et al. (1989) "Two regulatory genes of the maize anthocyanin pathway are homologous: isolation of B utilizing R genomic sequences," *Plant Cell* 1(12), 1175-1183.
97. Grotewold, E. et al. (1991) "Alternatively spliced products of the maize P gene encode proteins with homology to the DNA-binding domain of myb-like transcription factors," *P.N.A.S.* 88(11), 4587-4591.
98. Grotewold, E. et al. (1994) "The myb-homologous P gene controls phlobaphene pigmentation in maize floral organs by directly activating a flavonoid biosynthetic gene subset," *Cell* 76(3), 543-553.
99. Sidorenko, L. et al. (1999) "Characterization of the regulatory elements of the maize P-rr gene by transient expression assays," *Plant Mol. Biol* 39(1), 11-19.
100. Ralston, E. J. et al. (1988) "Sequence of three bronze alleles of maize and correlation with the genetic fine structure," *Genetics* 119(1), 185-197.

101. Nash, J. et al. (1990) "Bronze-2 gene of maize: reconstruction of a wild-type allele and analysis of transcription and splicing," *Plant Cell* 2(11), 1039-1049.

102. Bolte, S. et al. (2004) "The N-myristoylated Rab-GTPase m-Rabmc is involved in post-Golgi trafficking events to the lytic vacuole in plant cells," *J. Cell Sci.* 117(6), 943-954.

103. Kato, N. et al. (2002) "Spectral Profiling for the Simultaneous Observation of Four Distinct Fluorescent Proteins and Detection of Protein-Protein Interaction via Fluorescence Resonance Energy Transfer in Tobacco Leaf Nuclei," *Plant Physiol.* 129(3), 931-942.

104. Teeri, T. H. et al. (1989) "Gene fusions to lacZ reveal new expression patterns of chimeric genes in transgenic plants," *EMBO J.* 8(2), 343-350.

105. Sheen, J. et al. (1995) "Green-fluorescent protein as a new vital marker in plant cells," *Plant J.* 8(5), 777-784.

106. Dietrich, C. and Maiss, E. (2002) "Red fluorescent protein DsRed from Discosoma sp. as a reporter protein in higher plants," *BioTechniques* 32(2), 288-290, 292-283.

107. Sutcliffe, J. G. (1978) "Nucleotide sequence of the ampicillin resistance gene of *Escherichia coli* plasmid pBR322," *Proc. Natl. Acad. Sci. U.S.A* 75(8), 3737-3741.

108. Zukowski, M. M. et al. (1983) "Chromogenic identification of genetic regulatory signals in *Bacillus subtilis* based on expression of a cloned *Pseudomonas* gene," *P.N.A.S.* 80(4), 1101-1105.

109. Ikuta, N. et al. (1990) "The [alpha]-Amylase Gene as a Marker for Gene Cloning: Direct Screening of Recombinant Clones," *Nat. Biotechnol.* 8(3), 241-242.

110. Katz, E. et al. (1983) "Cloning and Expression of the Tyrosinase Gene from *Streptomyces antibioticus* in *Streptomyces lividans*," *J. Gen. Microbiol.* 129(9), 2703-2714.

111. Becker, T. W. et al. (1992) "Thecab-m7 gene: a light-inducible, mesophyll-specific gene of maize," *Plant Mol. Biol* 20(1), 49-60.

112. Knox, C. P. et al. (1987) "Structure and organization of two divergent α-amylase genes from barley," *Plant Mol. Biol* 9(1), 3-17.

113. Lerner, D. R. and Raikhel, N. V. (1989) "Cloning and Characterization of Root-Specific Barley Lectin," *Plant Physiol.* 91(1), 124-129.

114. Fontes, E. B. et al. (1991) "Characterization of an immunoglobulin binding protein homolog in the maize floury-2 endosperm mutant," *Plant Cell Environ.* 3(5), 483-496.

115. Matsuoka, K. and Nakamura, K. (1991) "Propeptide of a precursor to a plant vacuolar protein required for vacuolar targeting," *P.N.A.S.* 88(3), 834-838.

116. Gould, S. J. et al. (1989) "A conserved tripeptide sorts proteins to peroxisomes," *J. Cell Biol.* 108(5), 1657-1664.

117. Creissen, G. et al. (1992) "Molecular characterization of glutathione reductase cDNAs from pea (*Pisum sativum* L.)," *Plant J.* 2(1), 129-131.

118. Kalderon, D. et al. (1984) "A short amino acid sequence able to specify nuclear location," *Cell* 39(3), 499-509.

119. Stiefel, V. et al. (1990) "Expression of a maize cell wall hydroxyproline-rich glycoprotein gene in early leaf and root vascular differentiation," *Plant Cell* 2(8), 785-793.

120. Rogers, J. C. (1985) "Two barley alpha-amylase gene families are regulated differently in aleurone cells," *J. Biol. Chem.* 260(6), 3731-3738.

121. Shannon, J. C. et al. (1998) "Brittle-1, an Adenylate Translocator, Facilitates Transfer of Extraplastidial Synthesized ADP-Glucose into Amyloplasts of Maize Endosperms," *Plant Physiol.* 117(4), 1235-1252.

122. Sullivan, T. D. et al. (1991) "Analysis of maize brittle-1 alleles and a defective Suppressor-mutator-induced mutable allele," *Plant Cell* 3(12), 1337-1348.

123. Sullivan, T. and Kaneko, Y. (1995) "The maize brittle1 gene encodes amyloplast membrane polypeptides," *Planta* 196(3), 477-484.

124. Li, H. M. et al. (1992) "Information for targeting to the chloroplastic inner envelope membrane is contained in the mature region of the maize Btl-encoded protein," *J. Biol. Chem.* 267(26), 18999-19004.

125. Herrera-Estrella, L. et al. "Chimaeric Gene Coding For A Transit Peptide And A Heterologous Peptide," U.S. Pat. No. 5,717,084, application Ser. No. 08/470,719, filed Jun. 6, 1995. (issued Feb. 10, 1998).

126. Herrera-Estrella, L. et al. "Chimaeric Gene Coding For A Transit Peptide And A Heterologous Poly-Peptide," U.S. Pat. No. 5,728,925, application Ser. No. 08/430,257, filed Apr. 28, 1995. (issued Mar. 17, 1998).

127. Munro, S. and Pelham, H. R. B. (1987) "A C-terminal signal prevents secretion of luminal ER proteins," *Cell* 48(5), 899-907.

128. Raikhel, N. V. "Polypeptides Enabling Sorting Of Proteins To Vacuoles In Plants," U.S. Pat. No. 5,360,726, application Ser. No. 07/791,930, filed Nov. 12, 1991. (issued Nov. 1, 1994).

129. Warren, G. W. et al. "Nucleotide Sequences Encoding Pesticidal Proteins," U.S. Pat. No. 5,889,174, application Ser. No. 08/470,567, filed Jun. 6, 1995. (issued Mar. 30, 1999).

130. Holwerda, B. C. et al. (1992) "Proaleurain vacuolar targeting is mediated by short contiguous peptide interactions," *Plant Cell* 4(3), 307-318.

131. Nakamura, K. and Matsuoka, K. (1993) "Protein targeting to the vacuole in plant cells," *Plant Physiol.* 101(1), 1-5.

132. Saalbach, G. et al. (1991) "Different legumin protein domains act as vacuolar targeting signals," *Plant Cell* 3(7), 695-708.

133. Shinshi, H. et al. (1990) "Structure of a tobacco endochitinase gene: evidence that different chitinase genes can arise by transposition of sequences encoding a cysteine-rich domain," *Plant Mol. Riot* 14(3), 357-368.

134. McPherson, J. C. and Kay, R. "Dna Sequence For Enhancing The Efficiency Of Transcription," U.S. Pat. No. 5,322,938, application Ser. No. 07/977,600, filed Nov. 17, 1992. (issued Jun. 21, 1994).

135. Campbell, W. H. and Gowri, G. (1990) "Codon Usage in Higher Plants, Green Algae, and Cyanobacteria," *Plant Physiol.* 92(1), 1-11.

136. Adang, M. J. et al. "Synthetic Insecticidal Crystal Protein Gene," U.S. Pat. No. 5,380,831, application Ser. No. 08/057,191, filed May 3, 1993. (issued Jan. 10, 1995).

137. Fujimoto, H. et al. "Synthetic Insectidal Gene, Plants Of The Genus *Oryza* Transformed With The Gene, And Production Thereof," U.S. Pat. No. 5,436,391, application Ser. No. 07/982,712, filed Nov. 27, 1992. (issued Jul. 25, 1995).

138. Kozak, M. (1986) "Point mutations define a sequence flanking the AUG initiator codon that modulates translation by eukaryotic ribosomes," *Cell* 44(2), 283-292.

139. Kozak, M. (1987) "An analysis of 5'-noncoding sequences from 699 vertebrate messenger RNAs," *Nucleic Acids Res.* 15(20), 8125-8148.

140. MacDonald, M. H. et al. (1991) "Characterization of the polyadenylation signal from the T-DNA-encoded octopine synthase gene," *Nucleic Acids Res.* 19(20), 5575-5581.

141. Depicker, A. et al. (1982) "Nopaline synthase: transcript mapping and DNA sequence," *J. Mol. Appl. Genet.* 1(6), 561-573.
142. Shaw, C. H. et al. (1984) "A functional map of the nopaline synthase promoter," *Nucleic Acids Res.* 12(20), 7831-7846.
143. An, G. et al. (1989) "Functional analysis of the 3' control region of the potato wound-inducible proteinase inhibitor II gene," *Plant Cell* 1(1), 115-122.
144. Guerineau, F. et al. (1991) "Effect of deletions in the cauliflower mosaic virus polyadenylation sequence on the choice of the polyadenylation sites in tobacco protoplasts," *Mol. Gen. Genet.* 226(1), 141-144.
145. Proudfoot, N. (1991) "Poly(A) signals," *Cell* 64(4), 671-674.
146. Sanfaçon, H. et al. (1991) "A dissection of the cauliflower mosaic virus polyadenylation signal," *Genes Dev* 5(1), 141-149.
147. Mogen, B. et al. (1990) "Upstream sequences other than AAUAAA are required for efficient messenger RNA 3'-end formation in plants," *Plant Cell* 2(12), 1261-1272.
148. Munroe, D. and Jacobson, A. (1990) "Tales of poly(A): a review," *Gene* 91(2), 151-158.
149. Ballas, N. et al. (1989) "Efficient functioning of plant promoters and poly(A) sites in *Xenopus oocytes*," *Nucleic Acids Res.* 17(19), 7891-7903.
150. Joshi, C. P. (1987) "Putative polyadenylation signals in nuclear genes of higher plants: a compilation and analysis," *Nucleic Acids Res.* 15(23), 9627-9640.
151. Miki, B. and McHugh, S. (2004) "Selectable marker genes in transgenic plants: applications, alternatives and biosafety," *J. Biotechnol.* 107(3), 193-232.
152. Klein, T. M. et al. (1992) "Transformation of microbes, plants and animals by particle bombardment," *Nat. Biotechnol.* 10(3), 286-291.
153. Weising, K. et al. (1988) "Foreign genes in plants: transfer, structure, expression, and applications," *Annu. Rev. Genet.* 22(1), 421-477.
154. Fromm, M. et al. (1985) "Expression of genes transferred into monocot and dicot plant cells by electroporation," *P.N.A.S.* 82(17), 5824-5828.
155. Mathur, J. and Koncz, C. (1998) "PEG-Mediated Protoplast Transformation with Naked DNA," in *Arabidopsis Protocols* (Martinez-Zapater, J. and Salinas, J., Eds.), pp 267-276, Humana Press.
156. De Wet, J. M. J. "Method For The Transfer Of Exogenous Genes In Plants Using Pollen As A Vector" WIPO PCT Patent Publication Number WO/1985/001856, Application PCT/US1984/001774, filed Oct. 31, 1984. (published May 9, 1985).
157. Schilperoort, R. A. et al. "Process For The In-Vitro Transformation Of Plant Protoplasts With Plasmid Dna," U.S. Pat. No. 4,684,611, application Ser. No. 06/760,145, filed Jul. 29, 1985. (issued Aug. 4, 1987).
158. Crossway, A. et al. (1986) "Integration of foreign DNA following microinjection of tobacco mesophyll protoplasts," *Mol. Genet. Genomics* 202, 179-185.
159. Ishida, Y. et al. (1996) "High efficiency transformation of maize (*Zea mays* L.) mediated by *Agrobacterium tumefaciens*," *Nat. Biotechnol.* 14(6), 745-750.
160. Hiei, Y. and Komari, T. "Method For Transforming Monocotyledons," U.S. Pat. No. 5,591,616, application Ser. No. 08/193,058, filed May 3, 1994. (issued Jan. 7, 1997).
161. Fraley, R. T. et al. (1983) "Expression of bacterial genes in plant cells," *P.N.A.S.* 80(15), 4803-4807.
162. Rice, T. B. et al. "Methods And Compositions For The Production Of Stably Transformed, Fertile Monocot Plants And Cells Thereof," U.S. Pat. No. 5,550,318, application Ser. No. 07/565,844, filed Aug. 9, 1990. (issued Aug. 27, 1996).
163. Wilson, H. M. and Held, B. M. "Methods For Tissue Culturing And Transforming Elite Inbreds Of *Zea Mays* L," U.S. Pat. No. 6,420,630, application Ser. No. 09/203,679, filed Dec. 1, 1998. (issued Jul. 16, 2002).
164. Wilson, H. M. and Held, B. M. "Methods For Tissue Culturing And Transforming Elite Inbreds Of *Zea Mays* L," U.S. Pat. No. 6,919,494, application Ser. No. 09/917,964, filed Jul. 30, 2001. (issued Jul. 19, 2005).
165. Moloney, M. M. et al. (1989) "High efficiency transformation of *Brassica napus* using *Agrobacterium* vectors," *Plant Cell Rep.* 8(4), 238-242.
166. Fromm, M. et al. (1990) "Inheritance and expression of chimeric genes in the progeny of transgenic maize plants," *Bio/Technology* 8(9), 833-839.
167. Gordon-Kamm, W. et al. (1990) "Transformation of Maize Cells and Regeneration of Fertile Transgenic Plants," *Plant Cell* 2(7), 603-618.
168. Casas, A. M. et al. (1993) "Transgenic sorghum plants via microprojectile bombardment," *P.N.A.S.* 90(23), 11212-11216.
169. Wan, Y. and Lemaux, P. (1994) "Generation of Large Numbers of Independently Transformed Fertile Barley Plants," *Plant Physiol.* 104(1), 37-48.
170. Christou, P. et al. "Particle-Mediated Transformation Of Soybean Plants And Lines," U.S. Pat. No. 5,015,580, application Ser. No. 07/193,357, filed May 12, 1988. (issued May 14, 1991).
171. Armstrong, C. et al. (1991) "Development and availability of germplasm with high type II culture formation response," *Maize Genet Coop Newsletter* 13, 92-93.
172. Hood, E. E. et al. (1986) "The hypervirulence of *Agrobacterium tumefaciens* A281 is encoded in a region of pTiBo542 outside of T-DNA," *J. Bacteriol.* 168(3), 1291-1301.
173. Armstrong, C. L. and Green, C. E. (1985) "Establishment and maintenance of friable, embryogenic maize callus and the involvement of L-proline," *Planta* 164(2), 207-214.
174. Poehlman, J. M. and Sleper, D. A. (1995) *Breeding field crops*, 4th Edition ed., Iowa State University Press.
175. Jensen, N., (Ed.) (1988) *Plant Breeding Methodology*, John Wiley & Sons, Inc.
176. Hood, E. E. et al. (2007) "Subcellular targeting is a key condition for high-level accumulation of cellulase protein in transgenic maize seed," *Plant Biotechnol. J.* 5(6), 709-719.
177. Cosgrove, D. J. et al. (2002) "The Growing World of Expansins," *Plant Cell Physiol* 43(12), 1436-1444.
178. McQueen-Mason, S. J. and Cosgrove, D. J. (1995) "Expansin mode of action on cell walls. Analysis of wall hydrolysis, stress relaxation, and binding," *Plant Physiol.* 107(1), 87-100.
179. Howard, J. A. (2011) *Plant Biomass Conversion*, John Wiley & Sons, Inc.
180. Hood, E. E. et al. (2003) "Criteria for high-level expression of a fungal laccase gene in transgenic maize," *Plant Biotechnol. J.* 1(2), 129-140.
181. Woodard, S. L. et al. (2003) "Maize (*Zea mays*)-derived bovine trypsin: characterization of the first large-scale, commercial protein product from transgenic plants," *Biotechnol. Appl. Biochem.* 38(Pt 2), 123-130.

182. White, J. et al. (1990) "A cassette containing the bar gene of *Streptomyces hygroscopicus*: a selectable marker for plant transformation," *Nucleic Acids Res.* 18(4), 1062.
183. Anzai, H. et al. (1989) "Transgenic tobacco resistant to a bacterial disease by the detoxification of a pathogenic toxin," *Mol. Gen. Genet.* 219(3), 492-494.
184. Uchimiya, H. (1993) "Bialaphos Treatment of Transgenic Rice Plants Expressing a bar Gene Prevents Infection by the Sheath Blight Pathogen (*Rhizoctonia solani*)," *Bio/Technology* 11(7), 835-836.
185. Hiei, Y. et al. (1994) "Efficient transformation of rice (*Oryza sativa* L.) mediated by *Agrobacterium* and sequence analysis of the boundaries of the T-DNA," *Plant J.* 6(2), 271-282.
186. Sathitsuksanoh, N. et al. (2009) "Saccharification of a Potential Bioenergy Crop, *Phragmites australis* (Common Reed), by Lignocellulose Fractionation Followed by Enzymatic Hydrolysis at Decreased Cellulase Loadings," *Ind. Eng. Chem. Res.* 48, 6441-6447.
187. Streatfield, S. J. (2002) "Development of an Edible Subunit Vaccine in Corn against Enterotoxigenic Strains of *Escherichia coli*," *In Vitro Cellular and Development Biology—Plant* 38, 11-17.
188. Hood, E. E. et al. (2012) "Manipulating corn germplasm to increase recombinant protein accumulation," *Plant Biotechnol. J.* 10(1), 20-30.
189. Streatfield, S. J. (2007) "Approaches to achieve high-level heterologous protein production in plants," *Plant Biotechnol. J.* 5(1), 2-15.
190. Medrano, G. et al. (2009) "Rapid system for evaluating bioproduction capacity of complex pharmaceutical proteins in plants," in *Recombinant Proteins From Plants. Recombinant Proteins From Plants: Methods and Protocols*, pp 51-67, Humana Press, Totowa, N.J.
191. Streatfield, S. J. et al. (2001) "Plant-based vaccines: unique advantages," *Vaccine* 19(17-19), 2742-2748.

We claim:

1. A method of producing expansin, the method comprising introducing into a plant cell a vector comprising a heterologous nucleic acid molecule encoding an expansin protein, wherein said heterologous nucleic acid molecule encoding the expansin protein comprises a barley alpha amylase signal sequence and a localization sequence of SEQ ID NO:14, wherein said heterologous nucleic acid is operably linked to a regulatory region preferentially expressing said expansin protein in plant seed cells, and wherein said regulatory region is a globulin-1 promoter.

2. A plant comprising a vector comprising a heterologous nucleic acid molecule encoding an expansin protein, wherein said heterologous nucleic acid molecule encoding the expansin protein comprises a barley alpha amylase signal sequence and a localization sequence of SEQ ID NO:14, wherein said heterologous nucleic acid is operably linked to a regulatory region preferentially expressing said expansin protein in plant seed cells, and wherein said regulatory region is a globulin-1 promoter.

3. Seed of said plant of claim 2, wherein said seed contains said vector.

* * * * *

```
                          SEQUENCE LISTING

<160> NUMBER OF SEQ ID NOS: 14

<210> SEQ ID NO 1
<211> LENGTH: 723
<212> TYPE: DNA
<213> ORGANISM: Phyllostachys edulis

<400> SEQUENCE: 1
tctagagcgc cgcgagccct cgggcagtgg cagtccgggc acgccacgtt ctacggcggt     60
ggcgacgcct ccggcacaat gggaggcgcg tgcggttacg ggaacctgta cagccagggg    120
tacggcacga gcacggcggc gctgagcacg gcgctgttca acaacgggct gagctgcggg    180
tcgtgctacg agctgcggtg ctcgggcgac cccaagtggt gcctcccgg cgccatcacg     240 gtgacggcca ccaacttctg cccgcccaac tacgcgctcc caacaacga cggcggctgg     300 tgcaaccccc cgctccagca cttcgacctc gccgagcccg ccttcctcca catcgctcag    360
taccgcgccg gcatcgtccc cgtctccttc cgcagggtgg cgtgcgtgaa gaagggcggg    420
gtccggttca cggtgaacgg gcactcgtac ttcaacctgg tgctggtgac caacgtgggc    480
ggggcggggg acgtgcacgc ggtggcgatc aagggtcgc gcacggggtg gcagcccatg    540
gcgcgcaact ggggccagaa ctggcagagc aacgcctacc tcaacggcca ggcgctgtcc    600
ttccgcgtca ccgccagcga cggccgcgcg ctcacctccg ccaacgtcgc gcccgtgggg    660
tggcagttcg gccagacctt cgagggcgcc cagttccacc atcaccatca ccattaagag    720
ctc                                                                   723

<210> SEQ ID NO 2
<211> LENGTH: 702
<212> TYPE: DNA
<213> ORGANISM: Phyllostachys edulis

<400> SEQUENCE: 2
tctagagcgc cgcgagccct cgggcagtgg cagtccgggc acgccacgtt ctacggcggt     60
ggcgacgcct ccggcacaat gggaggcgcg tgcggttacg ggaacctgta cagccagggg    120
tacggcacga gcacggcggc gctgagcacg gcgctgttca acaacgggct gagctgcggg    180
tcgtgctacg agctgcggtg ctcgggcgac cccaagtggt gcctcccgg cgccatcacg     240 gtgacggcca ccaacttctg cccgcccaac tacgcgctcc caacaacga cggcggctgg     300 tgcaaccccc cgctccagca cttcgacctc gccgagcccg ccttcctcca catcgctcag    360
```

| | |
|---|---|
| taccgcgccg gcatcgtccc cgtctccttc cgcagggtgg cgtgcgtgaa gaagggcggg | 420 |
| gtccggttca cggtgaacgg gcactcgtac ttcaacctgg tgctggtgac caacgtgggc | 480 |
| ggggcggggg acgtgcacgc ggtggcgatc aaggggtcgc gcacggggtg gcagcccatg | 540 |
| gcgcgcaact ggggccagaa ctggcagagc aacgcctacc tcaacggcca ggcgctgtcc | 600 |
| ttccgcgtca ccgccagcga cggccgcgcg ctcacctccg ccaacgtcgc gcccgtgggg | 660 |
| tggcagttcg ccagaccctt cgagggcgcc cagttccacc at | 702 |

<210> SEQ ID NO 3
<211> LENGTH: 1029
<212> TYPE: DNA
<213> ORGANISM: Phyllostachys edulis

<400> SEQUENCE: 3

| | |
|---|---|
| atggcgtcct cctcttcctc catcctcctg ttcctcgctt ctcttctcct cgccgcgccg | 60 |
| cgagccctcg ggcagtggca gtccgggcac gccacgttct acggcggcgg cgacgcctcc | 120 |
| ggcacaatgg gtacgtgcac agaacatcaa ttttcattcc gttcttgaaa cttcaagtca | 180 |
| ctagtatacc ttgatggatt aattcgagcg tgcacgcgcg gcgtttgtgt gtgcgtacgt | 240 |
| gcaggaggcg cgtgcgggta cgggaacctg tacagccagg ggtacggccc gagcacggcg | 300 |
| gcgctgagca cggcgctgtt caacaacggg ctgagctgcg ggtcgtgcta cgagctgcgg | 360 |
| tgctcgggcg accccaagtg tgtgcttccc ggcgccatca cggtgacggc caccaacttc | 420 |
| tgcccgccca actacgcgct ccccaacaac gacggcggct ggtgcaaccc cccgctccag | 480 |
| cacttcgacc tcgccgagcc cgccttcctg cacatcgccc agtaccgcgc cggcatcgtc | 540 |
| cccgtctcgt tccgcaggca cgtcccctca ttcggtttct tttctttact ccaaccgtat | 600 |
| gtaactcgtt gttaccactg tgtcactgta gcgaaggcga cagtatacta ctagtaacta | 660 |
| ctcgtagaca gtaacgtcac atatagctac aatttcttca aatgctgcgt gttgctcgaa | 720 |
| tgcagggtgg cgtgcgtgaa gaagggcggg atccggttca cggtgaacgg gcactcgtac | 780 |
| ttcaacctgg tgctggtgac caacgtgggc ggcgccgggg acgtgcacgc ggtggcgatc | 840 |
| aggggtcgc gcacggggtg gcagcccatg tcgcgcaact ggggccagaa ctggcagagc | 900 |
| aacgcctacc tcaacggcca ggcgctctcc ttccgcgtca ccgccagcga cggccgcgcc | 960 |
| ctcacctgcg ccaacgtcgc gcccgcgggg tggcagttcg ccagaccctt cgagggcgcc | 1020 |
| cagttctaa | 1029 |

<210> SEQ ID NO 4
<211> LENGTH: 992
<212> TYPE: DNA
<213> ORGANISM: Cucumis sativus

<400> SEQUENCE: 4

| | |
|---|---|
| gaataattaa caaacattgc cactaattaa tctcatttat taaacacatt tcttttttcgc | 60 |
| taatctcccc tttcttcccc ctcttctctt ctaaacccac aaaacaaacc ccactttttct | 120 |
| tcacaaacta ttttcaaata taaacccatt cttatggctt tttcttactc acccttctcc | 180 |
| tctctctttc ttcttccttt cttctttgtc ttcaccttcg ctgactacgg tggctggcag | 240 |
| agcggccacg ccaccttta tggtggtggt gacgcatctg gcaccatggg tggagcttgt | 300 |
| gggtatggga atttatacag ccaagggtat ggcacgaaca cggtggcgct gagcactgcg | 360 |
| ctatttaaca atggattaag ttgtggtgct tgcttcgaaa tgacttgtac aaacgaccct | 420 |
| aaatggtgcc ttccgggaac tattagggtc actgccacca acttttgccc tcctaacttt | 480 |

-continued

```
gctctcccta caacaatgg tggatggtgc aaccctcctc tccaacactt cgacatggct    540
gagcctgcct tccttcaaat cgctcaatac cgagctggta tcgtcccgt ctcctttcgt    600 agggtaccat gtatgaagaa aggtggagtg aggtttacaa tcaatggcca ctcatacttc    660
aacctcgttt tgatcacaaa cgtcggtggc gcaggcgacg tccactctgt gtcgataaag    720
gggtctcgaa ctggatggca atccatgtct agaaattggg gccaaaactg gcaaagcaac    780
aactatctca atggccaagg cctttccttt caagtcactc ttagtgatgg tcgcactctc    840
actgcctata atctcgttcc ttccaattgg caatttggcc aaacctatga aggccctcaa    900 ttctaaaacca tatcagccac actgctatga ctactactac ttcacaaaac aaaacacaca    960
aaacaaacaa acaacaacaa aacgcgaacg ac                                  992
```

<210> SEQ ID NO 5
<211> LENGTH: 72
<212> TYPE: DNA
<213> ORGANISM: Artificial sequence
<220> FEATURE:
<223> OTHER INFORMATION: Synthetic

<400> SEQUENCE: 5

```
atggcgaaca agcacctgag ccttagcctc ttcctcgtgc tcctgggcct ctccgcctcc    60
ctcgcctccg gc                                                        72
```

<210> SEQ ID NO 6
<211> LENGTH: 129
<212> TYPE: DNA
<213> ORGANISM: Artificial Sequence
<220> FEATURE:
<223> OTHER INFORMATION: Synthetic

<400> SEQUENCE: 6

```
atggcccacg cccgcgtcct cctcctggcg ctcgccgtcc tggccacggc cgccgtcgcc    60
gtcgcctcct cctcctcctt cgccgactcc aacccgatcc ggccggtcac cgaccgcgcc   120
gcgtccacc                                                           129
```

<210> SEQ ID NO 7
<211> LENGTH: 20
<212> TYPE: DNA
<213> ORGANISM: Artificial sequence
<220> FEATURE:
<223> OTHER INFORMATION: Synthetic

<400> SEQUENCE: 7

```
accttctacg gcggtggtga                                                20
```

<210> SEQ ID NO 8
<211> LENGTH: 20
<212> TYPE: DNA
<213> ORGANISM: Artificial Sequence
<220> FEATURE:
<223> OTHER INFORMATION: Synthetic

<400> SEQUENCE: 8

```
catccagttc gagaccccctt                                               20
```

<210> SEQ ID NO 9
<211> LENGTH: 1138
<212> TYPE: DNA
<213> ORGANISM: Phyllostachys edulis

<400> SEQUENCE: 9

```
acattcgcgc ttctgtcaag taaaccgcct cagcacagag ctccaatggc gtcctcctct     60
tcctccatcc tcctgttcct cgcttctctt ctcctcgccg cgccgcgagc cctcgggcag    120
tggcagtccg ggcacgccac gttctacggc ggcggcgacg cctccggcac aatgggaggc    180
gcgtgcgggt acgggaacct gtacagccag gggtacggcc cgagcacggc ggcgctgagc    240
acggcgctgt tcaacaacgg gctgagctgc gggtcgtgct acgagctgcg gtgctcgggc    300
gaccccaagt ggtgcttccc cggcgccatc acggtgacgg ccaccaactt ctgcccgccc    360
aactacgcgc tccccaacaa cgacggcggc tggtgcaacc cccgctcca gcacttcgac    420
ctcgccgagc ccgccttcct gcacatcgcc cagtaccgcg ccggcatcgt ccccgtctcg    480
ttccgcaggg tggcgtgcgt gaagaagggc gggatccggt tcacggtgaa cgggcactcg    540
tacttcaacc tggtgctggt gaccaacgtg ggcggcgccg gggacgtgca cgcggtggcg    600
atcagggggt cgcgcacggg gtggcagccc atgtcgcgca actggggcca gaactggcag    660
agcaacgcct acctcaacgg ccaggcgctc tccttccgcg tcaccgccag cgacggccgc    720
gccctcacct cgccaacgt cgcgcccgcg gggtggcagt tcggccagac cttcgagggc    780
gcccagttct gatcacgacc cgaccgcag gattgacccg tccagctcct ttgattaatt    840
tagagcttta tgtttagcca agatgagatt cccttttta atctcgagtt tcatcggtgt    900
tgatttattc atctggtcca gccctgatgc tgaggttgct cctggaagaa acaaggatg    960
ggcacccgcg tgtcggaggc tgggacgtat ctgaatgttt gctgctcagt tctgttacct   1020
gagatttgta taggatatat aatactagta ctagagaagt gcggtagtgg tagagagtct   1080
cttgagagag aggcaaagag acttgtatgt atgaatgaaa ttgttcgttt gctttgtc    1138
```

<210> SEQ ID NO 10
<211> LENGTH: 1505
<212> TYPE: DNA
<213> ORGANISM: Zea mays

<400> SEQUENCE: 10

```
ggataatgtc gaatagatta ccaccctgtt tttctctaca tctccacaga agtctgatgc     60
tgaatctttt ttaatgctcc ctctaggctc tagcctatgt aacattggtc ccttaaattt    120
tattataatc aattgttttt gtgcaacttt ttaagtaaca gtaatcatgt gatattgctc    180
tttgagaatt ttcatatcca gaagtgtgag aatcctaaca acaatgaaat atttctgagc    240
aaatcttcat atatttcact gcattatgca tcctttgtca tgttggaaac ttatatggca    300
cccttttcaat gaataatact aaggcaagta tattttttaa ctaaatgatg cttagagtag    360
caaccaaata gattcctgat gatttttactt atttttgaaaa gattttttaac ccgttgcaac   420
gcacgggcac tcaactagta tatagataat aaagtataga ggcacagata gagatataga    480
gatagatata ttctcaccac aatcactaca gtacaacatt cacgagtgac cgcggatgca    540
ctcgagagga caaccgtacc acggcgcctt gcagaacact tcccaagccc aaagccatta    600
caccaaccac tctcgggctc tgctctattt atggaggagc agccagctac aggctacagc    660
cgtggcgaaa gcacacacgg atcaatcaca ctcactcgcg gccattgtcc tgcccgtgcg    720
tgctctgcct tttcaggcga tcgaccaacc aacttctcgt cactgccatg gctctgctct    780
ccgacctcat caacctcgac ctctcggggcc gcaccgggaa gatcatcgcc gagtacatct    840
ggtgcgaata gatagagatc tccccgtctc cgtctgatgc ccccccccc ccccttttt    900
cccgtggtgt cccttgggat gcttgctgtg ttccatcttg tgcatggatt ctcttttcct    960
```

-continued

| | |
|---|---|
| ccgtttcgtg tttatatttt actagtacat gggaagcgag tagaagagat cgctctctct | 1020 |
| ctctctctct ctctctctct ctctctctct ctcacacaca cacacacact agcagcaatt | 1080 |
| tcaaactgct ggcgttttaa ttccttctcc agttcctccc tcgatgacca cggcatgcca | 1140 |
| ttgccagcca cgtacaacgt actacaaggc acactaaccc actgccaagc acctcgtctg | 1200 |
| atctgatctg atgctgatgc agggttggcg gttccgggat ggacgtcagg agcaaagcca | 1260 |
| gggtcagtag tagtacacgc ttttgttcac cttcaatctt atccttatct tggcagtgta | 1320 |
| aaaattttt gtactttgt tggaagatag atagatagat atatgtgcct ttgcaagtgt | 1380 |
| gtctcttttc atgggcgtct tcttcacacg aagaaaaatg tcaaagtgca tgacatctca | 1440 |
| ccctgccttt tttttgggag ggtactcaga cgctgtccgg acctgttgat gaccccagca | 1500 |
| agctt | 1505 |

<210> SEQ ID NO 11
<211> LENGTH: 1401
<212> TYPE: DNA
<213> ORGANISM: Zea mays

<400> SEQUENCE: 11

| | |
|---|---|
| aagcttgccg agtgccatcc ttggacactc gataaagtat attttatttt tttattttg | 60 |
| ccaaccaaac tttttgtggt atgttcctac actatgtaga tctacatgta ccattttggc | 120 |
| acaattacat atttacaaaa atgttttcta taaatattag atttagttcg tttatttgaa | 180 |
| tttcttcgga aaattcacat ttaaactgca agtcactcga acatggaaa accgtgcatg | 240 |
| caaaataaat gatatgcatg ttatctagca caagttacga ccgatttcag aagcagacca | 300 |
| gaatcttcaa gcaccatgct cactaaacat gaccgtgaac ttgttatcta gttgtttaaa | 360 |
| aattgtataa aacacaaata aagtcagaaa ttaatgaaac ttgtccacat gtcatgatat | 420 |
| catatataga ggttgtgata aaaatttgat aatgtttcgg taaagttgtg acgtactatg | 480 |
| tgtagaaacc taagtgacct acacataaaa tcatagagtt tcaatgtagt tcactcgaca | 540 |
| aagactttgt caagtgtccg ataaaaagta ctcgacaaag aagccgttgt cgatgtactg | 600 |
| ttcgtcgaga tctctttgtc gagtgtcaca ctaggcaaag tctttacgga gtgttttca | 660 |
| ggctttgaca ctcggcaaag cgctcgattc cagtagtgac agtaatttgc atcaaaaata | 720 |
| gctgagagat ttaggccccg tttcaatctc acgggataaa gtttagcttc ctgctaaact | 780 |
| ttagctatat gaattgaagt gctaaagttt agtttcaatt accaccatta gctctcctgt | 840 |
| ttagattaca aatggctaaa agtagctaaa aaatagctgc taaagtttat ctcgcgagat | 900 |
| tgaaacaggg ccttaaaatg agtcaactaa tagaccaact aattattagc tattagtcgt | 960 |
| tagcttcttt aatctaagct aaaaccaact aatagcttat ttgttgaatt acaattagct | 1020 |
| caacggaatt ctctgttttt ctaaaaaaaa actgcccctc tcttacagca aattgtccgc | 1080 |
| tgcccgtcgt ccagatacaa tgaacgtacc tagtaggaac tcttttacac gctcggtcgc | 1140 |
| tcgccgcgga tcggagtccc cggaacacga caccactgtg gaacacgaca agtctgctc | 1200 |
| agaggcggcc acaccctggc gtgcaccgag ccggagcccg gataagcacg gtaaggagag | 1260 |
| tacggggga cgtggcgacc cgtgtgtctg ctgccacgca gccttcctcc acgtagccgc | 1320 |
| gcggccgcgc cacgtaccag ggcccggcgc tggtataaat gcgcgccacc tccgctttag | 1380 |
| ttctgcatac agccaaccca a | 1401 |

<210> SEQ ID NO 12
<211> LENGTH: 4145
<212> TYPE: DNA
<213> ORGANISM: Artificial sequence
<220> FEATURE:
<223> OTHER INFORMATION: Synthetic

<400> SEQUENCE: 12

| | | | | | | |
|---|---|---|---|---|---|---|
| ctgctccctg | cttgtgtgtt | ggaggtcgct | gagtagtgcg | cgagtaaaat | ttaagctaca | 60 |
| acaaggcaag | gcttgaccga | caattgcatg | aagaatctgc | ttagggttag | gcgttttgcg | 120 |
| ctgcttcgcg | atgtacgggc | cagatatacg | cgttgacatt | gattattgac | tagttattaa | 180 |
| tagtaatcaa | ttacggggtc | attagttcat | agcccatata | tggagttccg | cgttacataa | 240 |
| cttacggtaa | atggcccgcc | tggctgaccg | cccaacgacc | cccgcccatt | gacgtcaata | 300 |
| atgacgtatg | ttcccatagt | aacgccaata | gggactttcc | attgacgtca | atgggtggac | 360 |
| tatttacggt | aaactgccca | cttggcagta | catcaagtgt | atcatatgcc | aagtacgccc | 420 |
| cctattgacg | tcaatgacgg | taaatggccc | gcctggcatt | atgcccagta | catgacctta | 480 |
| tgggactttc | ctacttggca | gtacatctac | gtattagtca | tcgctattac | catggtgatg | 540 |
| cggttttggc | agtacatcaa | tgggcgtgga | tagcggtttg | actcacgggg | atttccaagt | 600 |
| ctccacccca | ttgacgtcaa | tgggagtttg | ttttggcacc | aaaatcaacg | ggactttcca | 660 |
| aaatgtcgta | acaactccgc | cccattgacg | caaatgggcg | gtaggcgtgt | acggtgggag | 720 |
| gtctatataa | gcagagctct | ctggctaact | agagaaccca | ctgcttaact | ggcttatcga | 780 |
| aattaatacg | actcactata | gggagaccgg | aagcttgccg | ccaccatggt | gagcaagggc | 840 |
| gaggagctgt | tcaccggggt | ggtgcccatc | ctggtcgagc | tggacggcga | cgtaaacggc | 900 |
| cacaagttca | gcgtgtccgg | cgagggcgag | ggcgatgcca | cctacggcaa | gctgaccctg | 960 |
| aagttcatct | gcaccaccgg | caagctgccc | gtgccctggc | ccaccctcgt | gaccaccttc | 1020 |
| acctacggcg | tgcagtgctt | cagccgctac | cccgaccaca | tgaagcagca | cgacttcttc | 1080 |
| aagtccgcca | tgcccgaagg | ctacgtccag | gagcgcacca | tcttcttcaa | ggacgacggc | 1140 |
| aactacaaga | cccgcgccga | ggtgaagttc | gagggcgaca | ccctggtgaa | ccgcatcgag | 1200 |
| ctgaagggca | tcgacttcaa | ggaggacggc | aacatcctgg | ggcacaagct | ggagtacaac | 1260 |
| tacaacagcc | acaacgtcta | tatcatggcc | gacaagcaga | agaacggcat | caaggtgaac | 1320 |
| ttcaagatcc | gccacaacat | cgaggacggc | agcgtgcagc | tcgccgacca | ctaccagcag | 1380 |
| aacacccca | tcggcgacgg | ccccgtgctg | ctgcccgaca | accactacct | gagcacccag | 1440 |
| tccgccctga | gcaaagaccc | caacgagaag | cgcgatcaca | tggtcctgct | ggagttcgtg | 1500 |
| accgccgccg | ggatcactct | cggcatggac | gagctgtaca | agtaaagcgg | ccgcgactct | 1560 |
| agaggatctt | tgtgaaggaa | ccttacttct | gtggtgtgac | ataattggac | aaactaccta | 1620 |
| cagagattta | aagctctaag | gtaaatataa | aatttttaag | tgtataatgt | gttaaactac | 1680 |
| tgattctaat | tgtttgtgta | ttttagattc | caacctatgg | aactgatgaa | tgggagcagt | 1740 |
| ggtggaatgc | ctttaatgag | gaaaacctgt | tttgctcaga | agaaatgcca | tctagtgatg | 1800 |
| atgaggctac | tgctgactct | caacattcta | ctcctccaaa | aagaagaga | aaggtagaag | 1860 |
| accccaagga | ctttccttca | gaattgctaa | gttttttgag | tcatgctgtg | tttagtaata | 1920 |
| gaactcttgc | ttgctttgct | atttacacca | caaaggaaaa | agctgcactg | ctatacaaga | 1980 |
| aaattatgga | aaaatattct | gtaacctta | taagtaggca | taacagttat | aatcataaca | 2040 |
| tactgttttt | tcttactcca | cacaggcata | gagtgtctgc | tattaataac | tatgctcaaa | 2100 |

```
aattgtgtac ctttagcttt ttaatttgta aaggggttaa taaggaatat ttgatgtata      2160
gtgccttgac tagagatcat aatcagccat accacatttg tagaggtttt acttgcttta      2220
aaaaacctcc cacacctccc cctgaacctg aaacataaaa tgaatgcaat tgttgttgtt      2280
aacttgttta ttgcagctta taatggttac aaataaagca atagcatcac aaatttcaca      2340
aataaagcat ttttttcact gcattctagt tgtggtttgt ccaaactcat caatgtatct      2400
tatcatgtct ggatcctgtg aatgtgtgt cagttagggt gtggaaagtc cccaggctcc       2460
ccagcaggca gaagtatgca aagcatgcat ctcaattagt cagcaaccag gtgtggaaag      2520
tccccaggct ccccagcagg cagaagtatg caaagcatgc atctcaatta gtcagcaacc      2580
atagtcccgc ccctaactcc gcccatcccg ccctaactc cgcccagttc cgcccattct       2640 ccgcccatg gctgactaat ttttttatt tatgcagagg ccgaggccgc ctcggcctct        2700
gagctattcc agaagtagtg aggaggcttt tttggaggcc taggcttttg caaaaagcta      2760
attcggcgta atctgctgct tgcaaacaaa aaaccaccg ctaccagcgg tggtttgttt       2820
gccggatcaa gagctaccaa ctcttttcc gaaggtaact ggcttcagca gagcgcagat       2880
accaaatact gtccttctag tgtagccgta gttaggccac cacttcaaga actctgtagc      2940
accgcctaca tacctcgctc tgctaatcct gttaccagtg ctgctgcca gtggcgataa       3000 gtcgtgtctt accgggttgg actcaagacg atagttaccg gataaggcgc agcggtcggg      3060
ctgaacgggg ggttcgtgca cacagcccag cttggagcga acgacctaca ccgaactgag      3120
atacctacag cgtgagctat gagaaagcgc cacgcttccc gaagggagaa aggcggacag      3180
gtatccggta agcggcaggg tcggaacagg agagcgcacg agggagcttc caggggggaaa     3240 cgcctggtat ctttatagtc ctgtcgggtt tcgccacctc tgacttgagc gtcgattttt      3300
gtgatgctcg tcagggggc ggagcctatg gaaaaacgcc agcaacgcaa gctagcttct       3360
agctagaaat tgtaaacgtt aatattttgt taaaattcgc gttaaatttt tgttaaatca      3420
gctcattttt taaccaatag gccgaaatcg gcaaaatccc ttataaatca aaagaatagc      3480
ccgagatagg gttgagtgtt gttccagttt ggaacaagag tccactatta agaacgtgg       3540 actccaacgt caaagggcga aaaccgtct atcaggcga tggccgccca ctacgtgaac        3600
catcacccaa atcaagtttt tggggtcga ggtgccgtaa agcactaaat cggaacccta      3660
aagggagccc ccgatttaga gcttgacggg gaaagccggc gaacgtggcg agaaaggaag      3720
ggaagaaagc gaaaggagcg gcgctaggg cgctggcaag tgtagcggtc acgctgcgcg       3780
taaccaccac acccgccgcg cttaatgcgc cgctacaggg cgcgtactat ggttgctttg      3840
acgagcacgt ataacgtgct ttcctcgttg gaatcagagc gggagctaaa caggaggccg      3900
attaaaggga ttttagacag gaacggtacg ccagctggac cgcggtcttt cggacttttg      3960
aaagtgatgg tggtgggga aggattcgaa ccttcgaagt cgatgacggc agatttagag       4020
tctgctccct ttggccgctc gggaaccca ccacgggtaa tgcttttact ggcctgctcc       4080
cttatcggga agcggggcgc atcatatcaa atgacgcgcc gctgtaaagt gttacgttga      4140
gaaag                                                                  4145
```

<210> SEQ ID NO 13
<211> LENGTH: 13
<212> TYPE: DNA
<213> ORGANISM: Artificial sequence
<220> FEATURE:
<223> OTHER INFORMATION: Synthetic

```
<220> FEATURE:
<221> NAME/KEY: misc_feature
<222> LOCATION: (7)..(7)
<223> OTHER INFORMATION: n= A or G

<400> SEQUENCE: 13
gccgccncca tgg                                                          13

<210> SEQ ID NO 14
<211> LENGTH: 4
<212> TYPE: PRT
<213> ORGANISM: Artificial sequence
<220> FEATURE:
<223> OTHER INFORMATION: Synthetic

<400> SEQUENCE: 14

Lys Asp Glu Leu
1
```